(12) United States Patent
Yu et al.

(10) Patent No.: US 10,301,299 B2
(45) Date of Patent: *May 28, 2019

(54) GLYCOSIDASE INHIBITORS

(71) Applicant: Merck Patent GmbH, Darmstadt (DE)

(72) Inventors: Henry Yu, Wellesley, MA (US); Lesley Liu-Bujalski, Bedford, MA (US); Theresa L. Johnson, Salem, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/830,675

(22) Filed: Dec. 4, 2017

(65) Prior Publication Data

US 2018/0093977 A1   Apr. 5, 2018

Related U.S. Application Data

(62) Division of application No. 14/775,134, filed as application No. PCT/US2014/022630 on Mar. 10, 2014, now Pat. No. 9,879,001.

(60) Provisional application No. 61/817,493, filed on Apr. 30, 2013, provisional application No. 61/782,353, filed on Mar. 14, 2013.

(51) Int. Cl.

| | | |
|---|---|---|
| *C07D 417/06* | (2006.01) |
| *C07D 413/06* | (2006.01) |
| *C07D 417/14* | (2006.01) |
| *C07D 277/46* | (2006.01) |
| *G01N 33/68* | (2006.01) |
| *A61K 31/426* | (2006.01) |
| *A61K 31/427* | (2006.01) |
| *A61K 31/454* | (2006.01) |
| *A61K 31/496* | (2006.01) |
| *A61K 31/498* | (2006.01) |

(52) U.S. Cl.
CPC .......... *C07D 417/06* (2013.01); *A61K 31/426* (2013.01); *A61K 31/427* (2013.01); *A61K 31/454* (2013.01); *A61K 31/496* (2013.01); *A61K 31/498* (2013.01); *C07D 277/46* (2013.01); *C07D 413/06* (2013.01); *C07D 417/14* (2013.01); *G01N 33/6893* (2013.01)

(58) Field of Classification Search
None
See application file for complete search history.

(56) References Cited

U.S. PATENT DOCUMENTS

| | | | |
|---|---|---|---|
| 4,600,025 A | 7/1986 | Grigg |
| 7,582,769 B2 | 9/2009 | Murray et al. |
| 2009/0012078 A1 | 1/2009 | Andrews et al. |
| 2009/0163545 A1 | 6/2009 | Goldfarb |
| 2011/0060019 A1 | 3/2011 | Murray et al. |

FOREIGN PATENT DOCUMENTS

| | | |
|---|---|---|
| CN | 103435606 A | 12/2013 |
| JP | 2010270034 A | 12/2010 |
| WO | 2004/002481 A1 | 1/2004 |
| WO | 2008/025170 A1 | 3/2008 |
| WO | 2009/131926 A1 | 10/2009 |
| WO | 2010/101949 A1 | 9/2010 |
| WO | 2010/108115 A1 | 9/2010 |

OTHER PUBLICATIONS

Veronika Skedelj; Eur. J. Medicinal Chem; 67, pp. 208-220, (2013).
Noel F. Albertson; J Amer Chem Society; 70(2); pp. 669-670 (1948).
Tony Lefebvre; Nature Chem Biol; 8(4); pp. 325-326 (2012).
Scott A. Yuzwa; Nature Chem Biol; 8(4); pp. 393-399 (2012).
Fahimeh Moradi-Afrapoli; Daru Journal of Pharmaceutical Sciences, 20(1); pp. 37 (2012).
Qiong Shen; J Med Chem; 53(23) pp. 8252-8259 (2010).
Danielle L. Graham; Neuropharmacology 79, pp. 307-313 (2014).
C. Wiessner; (XP009178995) Abstracts of the Annual Meetign of the Society for Neuroscience, Society for Neuroscience; Wash. DC; vol. 43 (2013).
Eun J. Kim; Molecules, 16, pp. 1987-2022 (2011).
CAS Registry (On-line) Nos. 948053-91-6; 697229-62-2; 540512-02-5; 346662-52-0; & 345992-64-5 (STN database summary sheets) Sep. 26, 2007.
Marotta NP, et al., Nature Chemistry, 7:913-920 (2015).
Nandi A, et al, Anal. Chem. 78:452-458 (2006).
Shan X, et al. Neuroscience Letters, 516:296-301 (2012).
Spillanti MG and Goedert M. Lancet Neurol. 12: 609-622 (2013).
Wang Z, et al. Mol. Cell Proteomics 9(1) 153-160 (2010).
Yuzwa SA, et al. Nature Chem. Biol., 8(4) 393-399 (2012).
S. Dassanayaka & S. Jones, Pharmacology & Therapeutics, 142; 62-71 (2014).
Baltzer, et al., Caplus 143:194249 2005.
Blom, et al. Caplus 148:55036 2007.
Grigg, et al. Caplus 96:104249 1982.
Jarry, et al. Caplus 101:151829 1984.
Kanai, et al. Caplus 107:217619 1987.
Murray, et al. Caplus 146:163100 2007.
Nayak, et al. Caplus 108:75273 1988.
Shiokawa, et al. Caplus 108:21897 1988.
Straley, et al. Caplus 62:67003 1965.
Yoshikawa, et al. Caplus 159:34194 2013.
Registry 941974-85-2, Chemcats p. 1 2007.
Bras, et al. Exp. Opin. Ther. Patents 24(8):857-874 2014.
Nakamura, et al. Bioorg. Med. Chem. Lett. 20, 4420-4423 2010.
Improper Markush, Fed. Reg. 76(27) 7162-7175, Training Slides 1, 64-67.

*Primary Examiner* — Heidi Reese
(74) *Attorney, Agent, or Firm* — Thomas W. Brown; EMD Serono Research Institute

(57) ABSTRACT

Compounds of formula (I)

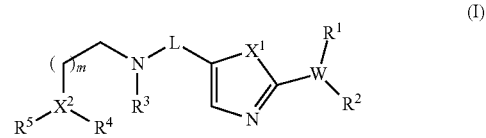

Figure 1:
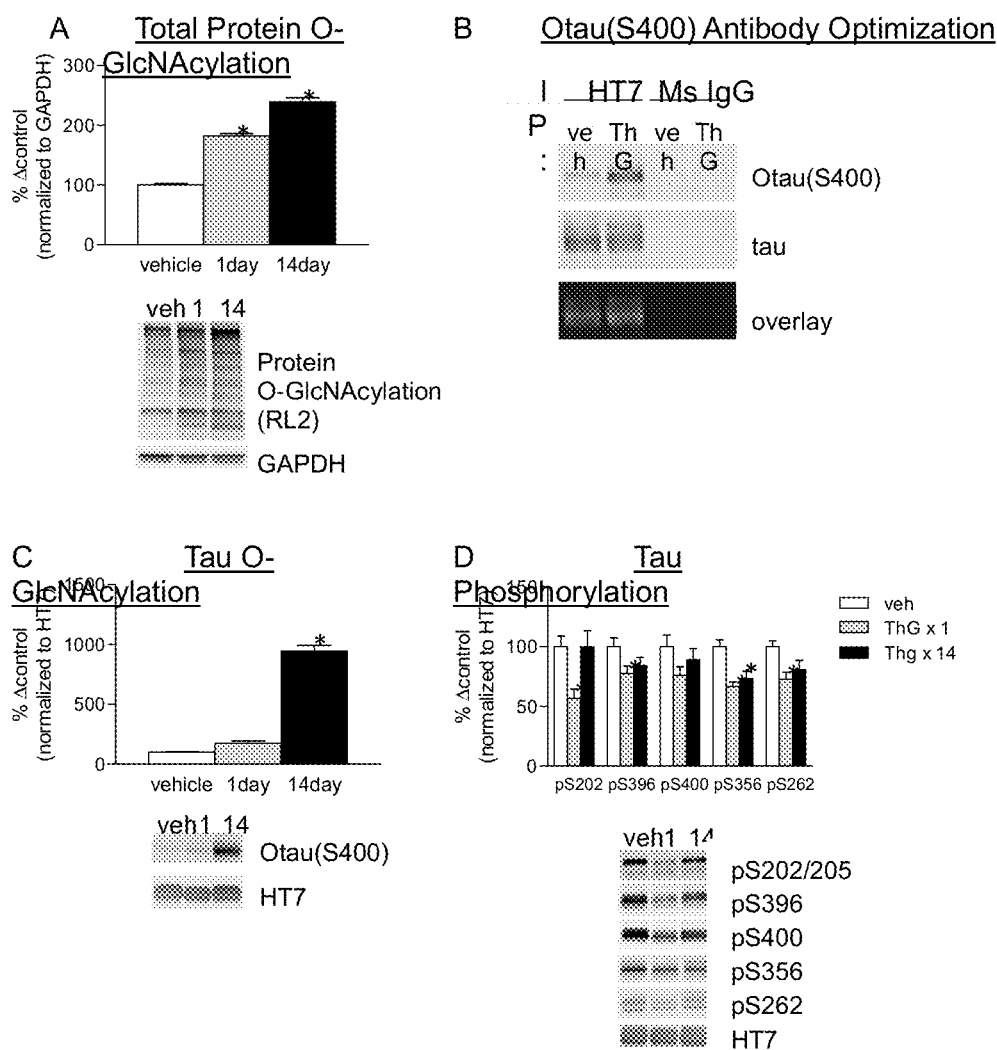

wherein $X^1$, $X^2$, W, $R^1$ to $R^5$, L and m have the meaning according to the claims, are glucosidase inhibitors, and can be employed, inter alia, for the treatment of Alzheimer's disease.

11 Claims, 3 Drawing Sheets

GLYCOSIDASE INHIBITORS

RELATED APPLICATION

This application is a Divisional application of U.S. application Ser. No. 14/775,134, filed on Sep. 11, 2015, which claims the benefit of U.S. Provisional Application No. 61/782,353, filed on Mar. 14, 2013, and U.S. Provisional Application No. 61/817,493, filed on Apr. 30, 2013. The entire contents of the aforementioned are hereby incorporated by reference.

The present invention relates to a medicament comprising a compound of formula (I)

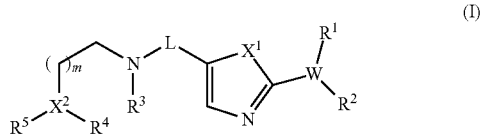

wherein $X^1$, $X^2$, W, $R^1$ to $R^5$, L and m have the meaning according to the claims, and/or physiologically acceptable salts thereof. The compounds of formula (I) can be used as glycosidase inhibitors. Objects of the invention are also pharmaceutical compositions comprising the compounds of formula (I), and the use of the compounds of formula (I) for the treatment of Alzheimer's disease.

A wide range of cellular proteins, both nuclear and cytoplasmic, are post-translationally modified by the addition of the monosaccharide 2-acetamido-2-deoxy-β-D-glucopyranoside (β-N-acetyl glucosamine) which is attached via an O-glycosidic linkage. This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase). A second enzyme, known as O-GlcNAcase, removes this post-translational modification to liberate proteins making the O-GlcNAc-modification a dynamic cycle occurring several times during the lifetime of a protein.

O-GlcNAc-modified proteins regulate a wide range of vital cellular functions including, for example, transcription, proteasomal degradation and cellular signaling. O-GlcNAc is also found on many structural proteins. For example, it has been found on a number of cytoskeletal proteins, including neurofilament proteins, synapsins, synapsin-specific clathrin assembly protein AP-3 and Ankyrin-G. O-GlcNAc modification has been found to be abundant in the brain. It has also been found on proteins clearly implicated in the etiology of several diseases including Alzheimer's disease (AD) and cancer.

For example, it is well established that AD and a number of related tauopathies including Downs' syndrome, Pick's disease, Niemann-Pick Type C disease and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally, tau stabilizes a key cellular network of microtubules that is essential for distributing proteins and nutrients within neurons. In AD patients, however, tau becomes hyperphosphorylated, disrupting its normal function, forming PHFs and ultimately aggregating to form NFTs. Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups. A clear parallel between NFT levels in the brains of AD patients and the severity of dementia strongly supports a key role for tau dysfunction in AD. The precise causes of this hyperphosphorylation of tau remain elusive. Accordingly, considerable effort has been dedicated toward: a) elucidating the molecular physiological basis of tau hyperphosphorylation; and b) identifying strategies that could limit tau hyperphosphorylation in the hope that these might halt, or even reverse, the progression of Alzheimer's disease. Several lines of evidence suggest that up-regulation of a number of kinases may be involved in hyperphosphorylation of tau, although very recently, an alternative basis for this hyperphosphorylation has been advanced.

In particular, it has recently emerged that phosphate levels of tau are regulated by the levels of O-GlcNAc on tau. The presence of O-GlcNAc on tau has stimulated studies that correlate O-GlcNAc levels with tau phosphorylation levels. The recent interest in this field stems from the observation that O-GlcNAc modification has been found to occur on many proteins at amino acid residues that are also known to be phosphorylated. Consistent with this observation, it has been found that increases in phosphorylation levels result in decreased O-GlcNAc levels and conversely, increased O-GlcNAc levels correlate with decreased phosphorylation levels. This reciprocal relationship between O-GlcNAc and phosphorylation has been termed the "Yin-Yang hypothesis" and has gained strong biochemical support by the recent discovery that the enzyme OGTase forms a functional complex with phosphatases that act to remove phosphate groups from proteins. Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD. Hyperphosphorylated tau in human AD brains has markedly lower levels of O-GlcNAc than are found in healthy human brains. Very recently, it has been shown that O-GlcNAc levels of soluble tau protein from human brains affected with AD are markedly lower than those from healthy brain. Furthermore, PHF from diseased brain was suggested to lack completely any O-GlcNAc modification whatsoever. The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosaminidase inhibitor was used to increase tau O-GlcNAc levels, whereupon it was observed that phosphorylation levels decreased. The implication of these collective results is that by maintaining healthy O-GlcNAc levels in AD patients, such as by inhibiting the action of O-GlcNAcase (OGA), one should be able to block hyperphosphorylation of tau and all of the associated effects of tau hyperphosphorylation, including the formation of NFTs and downstream effects. However, because the proper functioning of the lysosomal 1-hexosaminidases is critical, any potential therapeutic intervention for the treatment of AD that blocks the action of O-GlcNAcase would have to avoid the concomitant inhibition of both lysosomal hexosaminidases A and B.

Consistent with the known properties of the hexosamine biosynthetic pathway, the enzymatic properties of O-GlcNAc transferase (OGTase), and the reciprocal relationship between O-GlcNAc and phosphorylation, it has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase should compensate for the age-related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention comes from studies showing that when transgenic mice harboring human tau are treated with kinase inhibitors, they do not develop typical motor defects and, in another case, show a decreased level of insoluble tau. These studies provide a clear link between lowering tau phosphorylation levels and alleviating AD-like behavioral symptoms in a murine model of this disease.

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animal models of ischemia/reperfusion, trauma hemorrhage, hypervolemic shock and calcium paradox. Moreover, strong evidence indicates that these cardioprotective effects are mediated by elevated levels of protein O-GlcNAc modification. There is also evidence that the O-GlcNAc modification plays a role in a variety of neurodegenerative diseases, including Parkinson's disease and Huntington's disease.

Humans have three genes encoding enzymes that cleave terminal β-N-acetyl-glucosamine residues from glycoconjugates. The first of these encodes the enzyme O-glycoprotein-2-acetamido-2-deoxy-β-D-glucopyranosidase (O-GlcNAcase). O-GlcNAcase is a member of family 84 of glycoside hydrolases. O-GlcNAcase acts to hydrolyze O-GlcNAc off of serine and threonine residues of post-translationally modified proteins. Consistent with the presence of O-GlcNAc on many intracellular proteins, the enzyme O-GlcNAcase appears to have a role in the etiology of several diseases including type II diabetes, AD and cancer. Although O-GlcNAcase was likely isolated earlier on, about 20 years elapsed before its biochemical role in acting to cleave O-GlcNAc from serine and threonine residues of proteins was understood. More recently O-GlcNAcase has been cloned, partially characterized, and suggested to have additional activity as a histone acetyltransferase.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

US 2009/0163545 describes lifespan-altering compounds, such as (5-piperidin-1-ylmethyl-thiazol-2-yl)-carbamic acid methyl ester. WO 2010/108115 generically describes heterocyclic amide derivatives as allosteric Janus kinase inhibitors. WO 2010/101949 describes the preparation of 8-substituted quinolines as sirtuin modulators. N-[5-(4-Phenyl-piperidin-1-ylmethyl)-thiazol-2-yl]-acetamide is commercially available with undefined purpose. Low molecular weight OGA inhibitors are disclosed in the international application WO 2008/025170. There is a need for low molecular weight molecules that selectively inhibit OGA.

The invention had the object of finding novel compounds having valuable properties, in particular those which can be used for the preparation of medicaments.

It has been surprisingly found that the compounds according to the invention and salts thereof have very valuable pharmacological properties. In particular, they act as glycosidase inhibitors. The invention relates to compounds of formula (I) as medicament

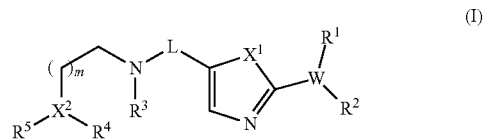

wherein
$X^1$ denotes S or O;
$X^2$, W denote independently from one another N or $CR^6$;
$R^1$, $R^3$, $R^4$ denote independently from one another Y;
$R^3$, $R^4$ together also denote —$(CY_2)_p$—;
$R^2$ denotes COY, Y, Alk, Cyc, $(CY_2)_n$Ar, COAlk, CO$(CY_2)_n$Ar, CONY$_2$, CONYAlk, CONY$(CY_2)_n$Ar, COOY, COOAlk, COO$(CY_2)_n$Ar, SO$_2$Y, SO$_2$Alk, SO$_2(CY_2)_n$Ar, CY$_2$OY or CY$_2$NY$_2$;
$R^1$, $R^2$ together also denote —$(CY_2)_p$— CONY$_2$—$(CY_2)_p$—;
$R^5$ denotes $(CY_2)_q$Ar, OAr, Cyc, Y or NY$_2$;
$R^6$ denotes Y, OY, Hal or CN;
L denotes —CY$_2$—, —CO— or —SO$_2$—;
Y denotes H or A;
A denotes unbranched or branched alkyl having 1-10 C atoms, in which 1-7 H atoms can be replaced independently from one another by Hal;
Alk denotes unbranched or branched alkenyl having 2-10 C atoms;
  in which 1-4 H atoms can be replaced independently from one another by Hal;
Cyc denotes cycloalkyl having 3-7 C atoms;
  in which 1-4 H atoms can be replaced independently from one another by Hal;
Ar denotes an unsaturated or aromatic mono- or bicyclic carbocycle having 3-12 C atoms,
  which can be substituted by at least one substituent selected from the group of Hal, A, $(CY_2)_n$—OY, $(CY_2)_n$—NY$_2$, COOY, SO$_2$Y and CN, or which can be fused to a saturated, an unsaturated or aromatic monocyclic heterocycle having 1-5 C atoms and 1-4 N, O and/or S atoms;
Hal denotes F, Cl, Br or I; and
m, n, p, q denote independently from one another 0, 1, 2 or 3;
and/or a physiologically acceptable salt thereof;
with the proviso that (5-piperidin-1-ylmethyl-thiazol-2-yl)-carbamic acid methyl ester is excluded.

The invention particularly relates to compounds of formula (I) as medicament

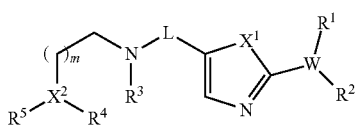

wherein
$X^1$ denotes S or O;
$X^2$, W denote independently from one another N or $CR^6$;
$R^1$, $R^3$, $R^4$ denote independently from one another Y;
$R^3$, $R^4$ together also denote —$(CY_2)_p$—;
$R^2$ denotes COY, Y, Alk, Cyc, $(CY_2)_n$Ar, COAlk, $CO(CY_2)_n$Ar, $CONY_2$, CONYAlk, $CONY(CY_2)_n$Ar, COOY, COOAlk, $COO(CY_2)_n$Ar, $SO_2Y$, $SO_2$Alk, $SO_2(CY_2)_n$Ar, $CY_2OY$ or $CY_2NY_2$;
$R^5$ denotes $(CY_2)_q$Ar, Cyc, Y or $NY_2$;
$R^6$ denotes Y, OY, Hal or CN;
L denotes —$CY_2$—, —CO— or —$SO_2$—;
Y denotes H or A;
A denotes unbranched or branched alkyl having 1-10 C atoms,
  in which 1-7 H atoms can be replaced independently from one another by Hal;
Alk denotes unbranched or branched alkenyl having 2-10 C atoms;
  in which 1-4 H atoms can be replaced independently from one another by Hal;
Cyc denotes cycloalkyl having 3-7 C atoms;
  in which 1-4 H atoms can be replaced independently from one another by Hal;
Ar denotes an unsaturated or aromatic mono- or bicyclic carbocycle having 3-12 C atoms,
  which can be substituted by at least one substituent selected from the group of Hal, A, $(CY_2)_n$—OY, $(CY_2)_n$—$NY_2$, COOY, $SO_2Y$ and CN;
Hal denotes F, Cl, Br or I; and
m, n, p, q denote independently from one another 0, 1, 2 or 3;
and/or a physiologically acceptable salt thereof;
with the proviso that (5-piperidin-1-ylmethyl-thiazol-2-yl)-carbamic acid methyl ester is excluded.

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention. It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by re-crystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. $Y_2$) the expression of such substituent may differ from each other (e.g. methyl and ethyl). It shall be understood accordingly that a multiple substitution by any radical of the invention may involve identical or different radicals. Hence, if individual radicals occur several times within a compound, the radicals adopt the meanings indicated, independently of one another.

The terms "alkyl" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In an embodiment of the invention, A denotes unbranched or branched alkyl having 1-10 C atoms, in which 1-7 H atoms may be replaced independently from one another by Hal. A preferred embodiment of A denotes unbranched or branched alkyl having 1-6 C atoms, in which 1-4 atoms may be replaced independently from one another by Hal. In a more preferred embodiment of the invention, A denotes unbranched or branched alkyl having 1-4 C atoms, in which 1-3 H atoms can be replaced independently from one another by Hal, particularly by F and/or Cl. It is most preferred that A denotes unbranched or branched alkyl having 1-6 C atoms. Highly preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of A is independently of one another in any radical of the invention.

The terms "alkenyl" or "Alk" refers to unbranched or branched alkenyl having 2, 3, 4, 5, 6, 7, 8, 9 or 10 C atoms, i.e. $C_2$-$C_{10}$-alkenyls. Alkenyls have at least one C—C double bond. Example of suitable alkenyls are allyl, vinyl, propenyl, —CH$_2$CH=CH$_2$, —CH=CH—CH$_3$, —C(=CH$_2$)—CH$_3$), 1-, 2- or 3-butenyl, isobutenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl and hexenyl.

In an embodiment of the invention, Alk denotes unbranched or branched alkenyl having 2-10 C atoms, in which 1-4 H atoms may be replaced independently from one another by Hal. A preferred embodiment of Alk denotes unbranched or branched alkenyl having 2-6 C atoms, in which 1-3 H atoms can be replaced independently from one another by Hal, particularly by F and/or Cl. In a more preferred embodiment of the invention, Alk denotes unbranched or branched alkenyl having 2-6 C atoms. In a most preferred embodiment of the invention, Alk denotes unbranched or branched alkenyl having 2-4 C atoms, highly preferably vinyl.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In an embodiment of the invention, Cyc denotes cycloalkyl having 3-7 C atoms, in which 1-4 H atoms may be replaced independently of one another by Hal. Preferred is $C_3$-$C_7$-cycloalkyl. More preferred is $C_4$-$C_7$-cycloalkyl. Most preferred is $C_5$-$C_7$-cycloalkyl, i.e. cyclopentyl, cyclohexyl or cycloheptyl, highly preferably cyclohexyl. It shall be understood that the respective denotation of Cyc is independently of one another in any radical of the invention.

The term "aryl" or "carboaryl" for the purposes of this invention refers to a mono- or polycyclic aromatic hydrocarbon systems having 3 to 14, preferably 3-12, more preferably 4 to 12, most preferably 5 to 10, highly preferably 6 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suited aryl radicals are phenyl, biphenyl, naphthyl, 1-naphthyl, 2-naphthyl and anthracenyl, but likewise in-danyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

In another embodiment of the invention, a carbocycle, including, but not limited to, carboaryl, is defined as "Ar". Examples of suitable Ar radicals are phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)-phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Ar preferably denotes an unsaturated or aromatic mono- or bicyclic carbocycle having 3-12 C atoms, which can be substituted by at least one substituent selected from the group of Hal, A, $(CY_2)_n$—OY, $(CY_2)_n$—NYY, COOY, SO$_2$Y and CN. In a more preferred embodiment of the invention, Ar denotes an unsaturated or aromatic mono- or bicyclic carbocycle having 4-12 C atoms, which can be substituted by at least one substituent selected from the group of Hal, A, OY, COOY and CN. It is most preferred that Ar denotes an aromatic mono- or bicyclic carbocycle having 5-10 C atoms, which can be mono- or disubstituted by at least one substituent selected from the group of Hal, A, OY, COOH and CN. In a highly preferred embodiment of the invention, Ar denotes an aromatic monocyclic carbocycle having 6-8 atoms, which can be monosubstituted by Hal, A or OY. It is particularly preferred that Ar denotes phenyl, which can be para- or metasubstituted by A or OY. It shall be understood that the respective denotation of Ar is independently of one another in any radical of the invention.

In an embodiment of the invention, Ar can be fused to a saturated, an unsaturated or aromatic monocyclic heterocycle having 1-5 C atoms and 1-4 N, O and/or S atoms. Ar can be preferably fused to a saturated or an aromatic monocyclic heterocycle having 2-4 C atoms and 1-3 O and/or N atoms. More preferably, Ar can be fused to a saturated or an aromatic monocyclic heterocycle having 3-4 C atoms and 2 O or N atoms.

The term "heterocycle" or "heterocyclyl" for the purposes of this invention refers to a monocyclic system of 3-9 ring atoms, preferably 3-7 ring atoms, more preferably 3-6 ring atoms, comprising carbon atoms and 1, 2, 3, 4 or 5 heteroatoms, which are identical or different, in particular nitrogen, oxygen and/or sulfur. The cyclic system may be saturated or mono- or poly-unsaturated, preferably unsaturated, more preferably an heteroaryl. In the case of a cyclic system consisting of at least two rings the rings may be fused or spiro or otherwise connected. Such heterocyclyl radicals can be linked via any ring member. The term "heterocyclyl" also includes systems in which the heterocycle is part of a bi- or polycyclic saturated, partially unsaturated and/or aromatic system, such as where the heterocycle is fused to an aryl, cycloalkyl, heteroaryl or heterocyclyl group as defined herein via any desired and possible ring member of the heterocyclyl radical. The bonding to the compounds of the general formula (I) can be effected via any possible ring member of the heterocyclyl radical. Examples of suitable heterocyclyl radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

The term "heteroaryl" for the purposes of this invention refers to 3-9, preferably 4-, 5- or 6-membered monocyclic aromatic hydrocarbon radical which comprises at least 1, where appropriate also 2, 3, 4 or 5 heteroatoms, preferably nitrogen, oxygen and/or sulfur, where the heteroatoms are identical or different. The number of heteroatoms is preferably 1 or 2, more preferably 2. The term "heteroaryl" also includes systems in which the aromatic cycle is part of a bicyclic saturated, partially unsaturated and/or aromatic system, such as where the aromatic cycle is fused to an aryl, cycloalkyl, heteroaryl or heterocyclyl group as defined herein via any desired and possible ring member of the heteroaryl radical. The bonding to the compounds of the general formula (I) can be effected via any possible ring member of the heteroaryl radical. Examples of suitable heteroaryl are pyrrolyl, thienyl, furyl, imidazolyl, thiazyl, isothiazyl, oxazyl, oxadiazyl, isoxazyl, pyrazyl, pyridyl, pyrimidyl, pyridazinyl, pyrazyl, indolyl, quinolyl, isoquinolinyl, imidazolyl, triazolyl, triazinyl, tetrazyl, phthalazinyl, indazolyl, indolizinyl, quinoxalinyl, quinazolinyl, pteridinyl, carbazolyl, phenazinyl, phenoxazinyl, phenothiazinyl and acridinyl.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, particularly when the halogens are substituted on an alkyl (haloalkyl) or alkoxy group (e.g. $CF_3$ and $CF_3O$). It shall be understood that the respective denotation of Hal is independently of one another in any radical of the invention.

It is an embodiment of the present invention that $X^1$ denotes S or O, preferably S.

It is another embodiment of the present invention that $X^2$ denotes $CR^6$ or N, preferably $CR^6$, more preferably CY, most preferably CH.

It is an embodiment of the present invention that W denotes N or $CR^6$, preferably N or CY, more preferably N or CH, most preferably N.

It is another preferred embodiment of the present invention that $X^2$ denotes CY and/or W denotes N or CH.

It is another preferred embodiment of the present invention that $R^1$ denotes H or A, more preferably H.

It is an embodiment of the present invention that $R^2$ denotes COY, Y, Alk, Cyc, $(CY_2)_n$Ar, COAlk, CO$(CY_2)_n$Ar, $CONY_2$, CONYAlk, CONY$(CY_2)_n$Ar, COOY, COOAlk, COO$(CY_2)_n$Ar, $SO_2Y$, $SO_2$Alk, $SO_2(CY_2)_n$Ar, $CY_2OY$ or $CY_2NY_2$; preferably COY, Y, Cyc, $(CY_2)_n$Ar, COAlk, CO$(CY_2)_n$Ar, $CONY_2$, CONY$(CY_2)_n$Ar, COOY, COO$(CY_2)_n$Ar, $SO_2Y$, $CY_2OY$ or $CY_2NY_2$; more preferably COY, Y, Cyc, $(CY_2)_n$Ar, COAlk, COAr, CONYY, CONYAr, COOY, COO$(CY_2)_n$Ar or $SO_2Y$; most preferably COY, COAlk, $CONY_2$ or COOY; highly preferably COA, COAlk, CONHA or COOA; particularly highly preferably COY; and very particularly highly preferably COA.

It is excluded in another preferred aspect of the present invention that $R^1$ and $R^2$ denote H at the same time.

It is another preferred embodiment of the present invention that $R^3$ denotes H or A, more preferably A.

It is another preferred embodiment of the present invention that $R^4$ denotes H or A, more preferably H.

It is a preferred embodiment of the present invention that $R^3$ and $R^4$ together denote —$(CY_2)_p$—, more preferably —$(CH_2)_p$—, and most preferably —$(CH_2)_2$—.

It is an embodiment of the present invention that $R^5$ denotes $(CY_2)_q$Ar, Cyc, Y or $NY_2$; preferably $(CY_2)_q$Ar, Cyc, H or A; more preferably $(CH_2)_q$Ar, Cyc or A; most preferably $(CH_2)_q$Ar or Cyc; highly preferably $(CH_2)_q$Ar; and particularly highly preferably Ar.

It is another embodiment of the present invention that $R^6$ denotes Y, OY, Hal or CN; preferably H, A, OY or Hal; more preferably H, A, OH or Hal; most preferably H, OH or Hal; and highly preferably H.

It is an embodiment of the present invention that L denotes —$CY_2$—, —CO— or —$SO_2$—; preferably $CY_2$; more preferably CHY; and most preferably $CH_2$.

It is another preferred embodiment of the present invention that W denotes N; $R^2$ denotes COY, COAlk, $CONY_2$ or COOY; and/or L denotes $CY_2$. It is more preferred embodiment of the present invention that W denotes N; $R^2$ denotes COY; and L denotes CHY.

In an aspect of the invention, Y denotes H or A. It shall be understood that the respective denotation of Y is independently of one another in any radical of the invention.

It is another embodiment of the present invention that the index m denotes 0, 1, 2 or 3; preferably 0, 1 or 2; more preferably 1 or 2; and most preferably 1.

It is an embodiment of the present invention that the index n denotes 0, 1, 2 or 3; preferably 0, 1 or 2; more preferably 0 or 1; and most preferably 0. It shall be understood that the respective denotation of the index n is independently of one another in any radical of the invention.

It is an embodiment of the present invention that the index p denotes 0, 1, 2 or 3; preferably 1, 2 or 3; more preferably 1 or 2; and most preferably 2.

It is an embodiment of the present invention that the index q denotes 0, 1, 2 or 3; preferably 0, 1 or 2; more preferably 0 or 1; and most preferably 0.

It is an embodiment of the present invention that the indices m and p denote independently from one another 1 or 2, and/or the indices n and q denote independently from one another 0 or 1.

Accordingly, the subject-matter of the invention relates to compounds of formula (I) as medicament, in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention.

That means that the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

In another more preferred embodiment of the present invention, compounds of sub-formula (IA) are provided as medicament

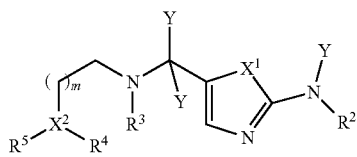

(IA)

wherein
$X^1$ denotes S or O;
$X^2$ denotes $CR^6$ or N;
$R^2$ denotes COY, COAlk, $CONY_2$ or COOY;
$R^3$, $R^4$ denote independently from one another Y;
$R^3$, $R^4$ together also denote —$(CY_2)_p$—;
$R^5$ denotes $(CY_2)_q$Ar, Cyc or Y;
$R^6$ denotes Y, OY or Hal;
Y denotes H or A;
A denotes unbranched or branched alkyl having 1-10 C atoms,
  in which 1-7 H atoms can be replaced independently from one another by Hal;
Alk denotes unbranched or branched alkenyl having 2-6 C atoms;
  in which 1-3 H atoms can be replaced independently from one another by Hal;
Cyc denotes cycloalkyl having 3-7 C atoms;
  in which 1-4 H atoms can be replaced independently from one another by Hal;
Ar denotes an unsaturated or aromatic mono- or bicyclic carbocycle having 4-12 C atoms,
  which can be substituted by at least one substituent selected from the group of
  Hal, A, OY, COOY and CN;
Hal denotes F, Cl, Br or I;
m, q denote independently from one another 0, 1 or 2; and
p denotes 1, 2 or 3;
and/or a physiologically acceptable salt thereof;
with the proviso that (5-piperidin-1-ylmethyl-thiazol-2-yl)-carbamic acid methyl ester is excluded.

In another most preferred embodiment of the present invention, compounds of sub-formula (IB) are provided as medicament

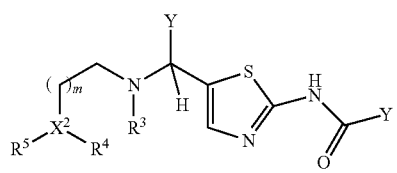

(IB)

wherein
$X^2$ denotes CY or N;
$R^3$, $R^4$ denote independently from one another Y;
$R^3$, $R^4$ together also denote —$(CH_2)_p$—;
$R^5$ denotes $(CH_2)_q$Ar, Cyc or A;
Y denotes H or A;
A denotes unbranched or branched alkyl having 1-6 C atoms,
  in which 1-4 H atoms can be replaced independently from one another by Hal;
Cyc denotes cycloalkyl having 4-7 C atoms;
Ar denotes an aromatic mono- or bicyclic carbocycle having 5-10 C atoms,
  which can be mono- or disubstituted by at least one substituent selected from the group of Hal, A, OY, COOH and CN;
Hal denotes F, Cl, Br or I;
m denotes 0, 1 or 2;
p denotes 1 or 2; and
q denotes 0 or 1;
and/or a physiologically acceptable salt thereof.

In another highly preferred embodiment of the present invention, compounds of sub-formula (IC) are provided as medicament

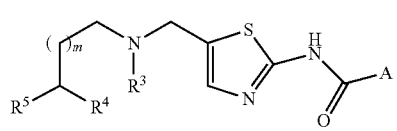

(IC)

wherein
$R^3$ denotes A;
$R^4$ denotes H;
$R^3$, $R^4$ together also denote —$(CH_2)_p$—;
$R^5$ denotes $(CH_2)_q$Ar, Cyc or A;
Y denotes H or A;
A denotes unbranched or branched alkyl having 1-4 C atoms,
  in which 1-3 H atoms can be replaced independently from one another by Hal;
Cyc denotes cycloalkyl having 5-7 C atoms;
Ar denotes an aromatic monocyclic carbocycle having 6-8 C atoms,
  which can be monosubstituted by Hal, A or OY;

Hal denotes F, Cl, Br or I;
m, p denote independently from one another 1 or 2; and
q denotes 0 or 1;
and/or a physiologically acceptable salt thereof.

In another aspect of the formulae (I) or (IA) to (IC), it is excluded that $R^3$ and $R^5$ denote A at the same time.

In still another highly preferred embodiment of the present invention, compounds of sub-formula (ID) are provided as medicament

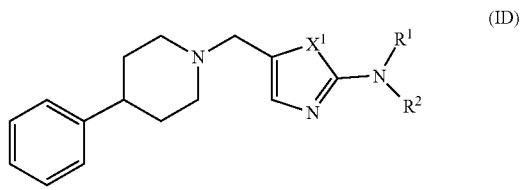

(ID)

wherein
$X^1$ denotes S or O;
$R^1$ denotes H or A;
$R^2$ denotes COA, COAlk, CONHA or COOA;
A denotes unbranched or branched alkyl having 1-6 C atoms; and
Alk denotes unbranched or branched alkenyl having 2-6 C atoms;
and/or a physiologically acceptable salt thereof.

The prior teaching of the present specification concerning the compounds of formula (I), including any radical definition and preferred embodiment thereof, is valid and applicable without restrictions to the compounds according to sub-formulae (IA) to (ID) and their salts, if expedient.

Particularly highly preferred embodiments are those compounds of formula (I) and sub-formulae (IA) to (ID) listed in Table 1 and/or physiologically acceptable salts thereof.

TABLE 1

Compounds of formulae (I) and sub-formulae (IA) to (ID). OGA enzyme inhibition assay: EXAMPLE 12. Cellular O-GlcNAcylation assay: EXAMPLE 13.

| No. | Structure | hOGA enzyme inhibition ($IC_{50}$)<br>+ ≥10 μM<br>++ 1 < 10 μM<br>+++ 0.2 < 1 μM<br>++++ <0.2 μM | B35 Cell ($EC_{50}$, ICC)<br>+ 10 μM<br>++ 1 < 10 μM<br>+++ 0.2 < 1 μM<br>++++ <0.2 μM | General synthetic route |
|---|---|---|---|---|
| 1 | [structure] | ++++ | +++ | scheme 5 |
| 2 | [structure] | ++ | + | scheme 7 |
| 3 | [structure] | +++ | | scheme 1 |
| 4 | [structure] | ++ | | scheme 5 |
| 5 | [structure] | + | | scheme 5 |

TABLE 1-continued

Compounds of formulae (I) and sub-formulae (IA) to (ID). OGA enzyme inhibition assay: EXAMPLE 12. Cellular O-GlcNAcylation assay: EXAMPLE 13.

| No. | Structure | hOGA enzyme inhibition (IC$_{50}$)<br>+ ≥10 μM<br>++ 1 < 10 μM<br>+++ 0.2 < 1 μM<br>++++ <0.2 μM | B35 Cell (EC$_{50}$, ICC)<br>+ 10 μM<br>++ 1 < 10 μM<br>+++ 0.2 < 1 μM<br>++++ <0.2 μM | General synthetic route |
|---|---|---|---|---|
| 6 | 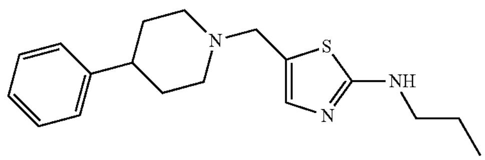 [SMILES: CCCNc1ncc(CN2CCC(c3ccccc3)CC2)s1] | | + | scheme 5 |
| 7 | 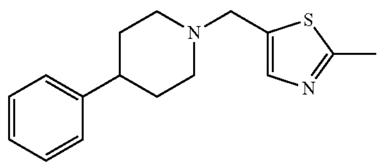 [SMILES: Cc1ncc(CN2CCC(c3ccccc3)CC2)s1] | | + | scheme 1 |
| 8 | 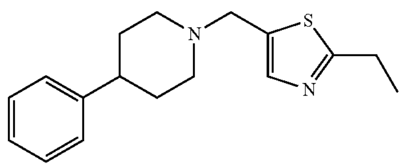 [SMILES: CCc1ncc(CN2CCC(c3ccccc3)CC2)s1] | | + | scheme 1 |
| 9 | 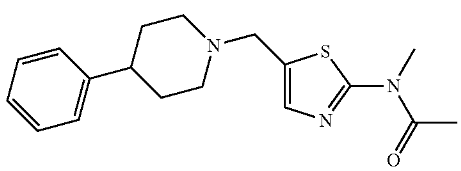 [SMILES: CC(=O)N(C)c1ncc(CN2CCC(c3ccccc3)CC2)s1] | | ++ | scheme 5 |
| 10 | 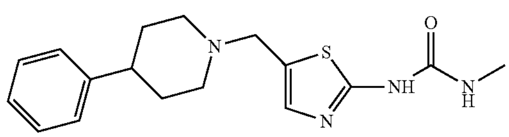 [SMILES: CNC(=O)Nc1ncc(CN2CCC(c3ccccc3)CC2)s1] | | ++ | scheme 1 modified scheme 5 |
| 11 | 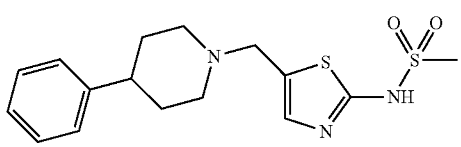 [SMILES: CS(=O)(=O)Nc1ncc(CN2CCC(c3ccccc3)CC2)s1] | | + | scheme 7 |
| 12 | 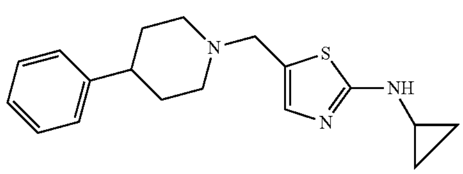 [SMILES: c1ccc(C2CCN(Cc3cnc(NC4CC4)s3)CC2)cc1] | | + | scheme 4 |
| 13 | 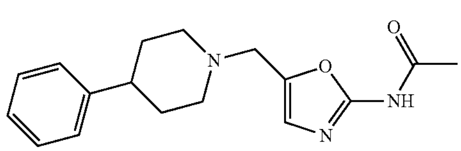 [SMILES: CC(=O)Nc1ncc(CN2CCC(c3ccccc3)CC2)o1] | | ++ | scheme 4 modified scheme 5 |

TABLE 1-continued

Compounds of formulae (I) and sub-formulae (IA) to (ID). OGA enzyme inhibition assay: EXAMPLE 12. Cellular O-GlcNAcylation assay: EXAMPLE 13.

| No. | Structure | hOGA enzyme inhibition (IC$_{50}$)<br>+ ≥10 μM<br>++ 1 < 10 μM<br>+++ 0.2 < 1 μM<br>++++ <0.2 μM | B35 Cell (EC$_{50}$, ICC)<br>+ 10 μM<br>++ 1 < 10 μM<br>+++ 0.2 < 1 μM<br>++++ <0.2 μM | General synthetic route |
|---|---|---|---|---|
| 14 | 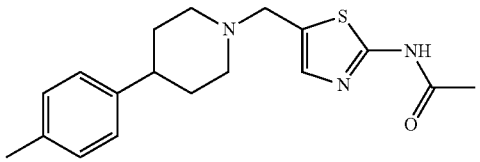 [SMILES: CC(=O)Nc1ncc(CN2CCC(c3ccc(C)cc3)CC2)s1] | ++++ | +++ | scheme 3 |
| 15 | 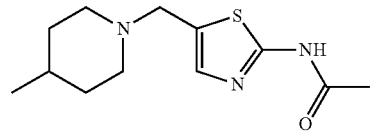 [SMILES: CC(=O)Nc1ncc(CN2CCC(C)CC2)s1] | ++ | | scheme 2 |
| 16 | 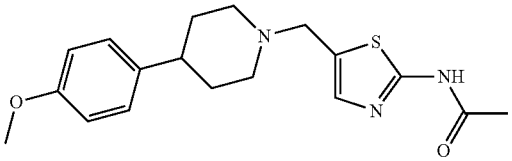 [SMILES: COc1ccc(C2CCN(Cc3cnc(NC(C)=O)s3)CC2)cc1] | ++++ | ++ | scheme 3 |
| 17 | 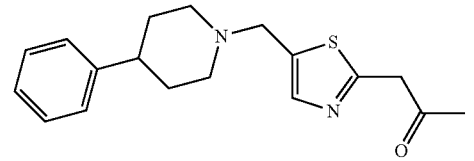 [SMILES: CC(=O)Cc1ncc(CN2CCC(c3ccccc3)CC2)s1] | + | | scheme 6 |
| 18 | 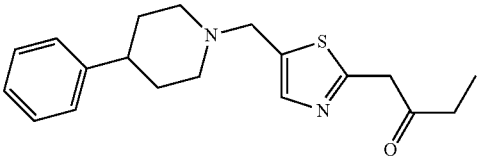 [SMILES: CCC(=O)Cc1ncc(CN2CCC(c3ccccc3)CC2)s1] | + | | scheme 6 |
| 19 | 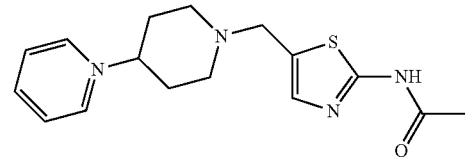 | +++ | ++ | scheme 2 |
| 20 | 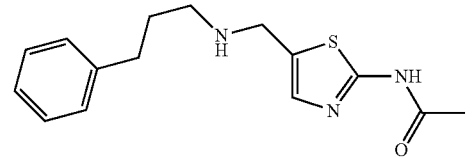 [SMILES: CC(=O)Nc1ncc(CNCCCc2ccccc2)s1] | +++ | ++ | scheme 2 |
| 21 | 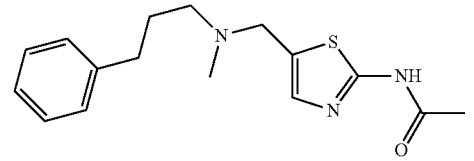 [SMILES: CC(=O)Nc1ncc(CN(C)CCCc2ccccc2)s1] | ++++ | ++ | scheme 2 |

TABLE 1-continued

Compounds of formulae (I) and sub-formulae (IA) to (ID). OGA enzyme inhibition assay: EXAMPLE 12. Cellular O-GlcNAcylation assay: EXAMPLE 13.

| No. | Structure | hOGA enzyme inhibition (IC$_{50}$)<br>+ ≥10 μM<br>++ 1 < 10 μM<br>+++ 0.2 < 1 μM<br>++++ <0.2 μM | B35 Cell (EC$_{50}$, ICC)<br>+ 10 μM<br>++ 1 < 10 μM<br>+++ 0.2 < 1 μM<br>++++ <0.2 μM | General synthetic route |
|---|---|---|---|---|
| 22 | 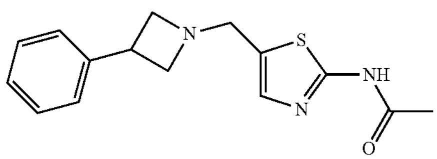 [SMILES: CC(=O)Nc1ncc(CN2CC(c3ccccc3)C2)s1] | +++ | ++ | scheme 2 |
| 23 | 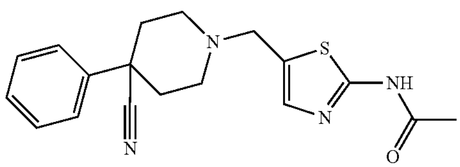 [SMILES: CC(=O)Nc1ncc(CN2CCC(C#N)(c3ccccc3)CC2)s1] | + | | scheme 2 |
| 24 | 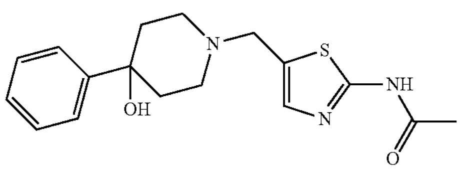 [SMILES: CC(=O)Nc1ncc(CN2CCC(O)(c3ccccc3)CC2)s1] | ++ | | scheme 2 |
| 25 | 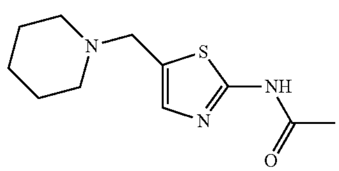 [SMILES: CC(=O)Nc1ncc(CN2CCCCC2)s1] | ++ | +++ | scheme 2 |
| 26 | 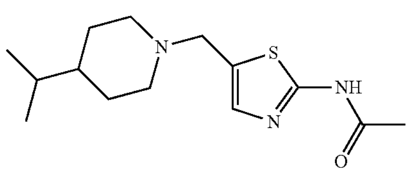 [SMILES: CC(=O)Nc1ncc(CN2CCC(C(C)C)CC2)s1] | ++++ | ++ | scheme 2 |
| 27 | 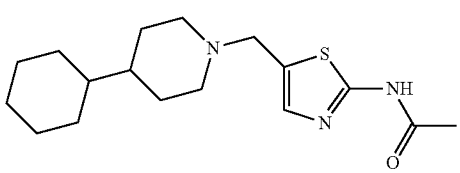 [SMILES: CC(=O)Nc1ncc(CN2CCC(C3CCCCC3)CC2)s1] | ++++ | ++++ | scheme 2 |
| 28 | 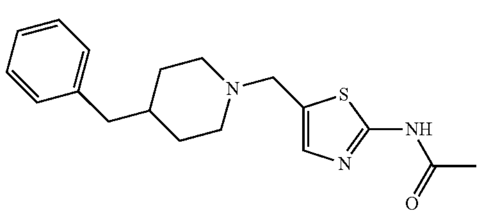 [SMILES: CC(=O)Nc1ncc(CN2CCC(Cc3ccccc3)CC2)s1] | ++++ | ++++ | scheme 2 |

TABLE 1-continued

Compounds of formulae (I) and sub-formulae (IA) to (ID). OGA enzyme inhibition assay: EXAMPLE 12. Cellular O-GlcNAcylation assay: EXAMPLE 13.

| No. | Structure | hOGA enzyme inhibition (IC$_{50}$) + ≥10 μM ++ 1 < 10 μM +++ 0.2 < 1 μM ++++ <0.2 μM | B35 Cell (EC$_{50}$, ICC) + 10 μM ++ 1 < 10 μM +++ 0.2 < 1 μM ++++ <0.2 μM | General synthetic route |
|---|---|---|---|---|
| 29 | 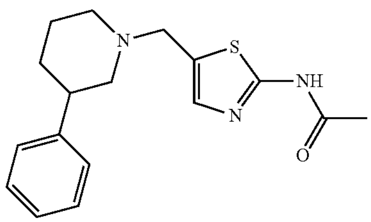 [SMILES: CC(=O)Nc1ncc(CN2CCCC(c3ccccc3)C2)s1] | ++++ | ++ | scheme 2 |
| 30 | 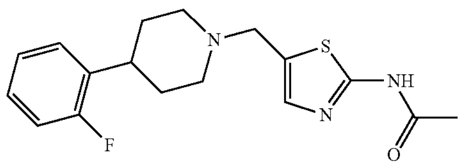 [SMILES: CC(=O)Nc1ncc(CN2CCC(c3ccccc3F)CC2)s1] | +++ | +++ | scheme 3 |
| 31 | 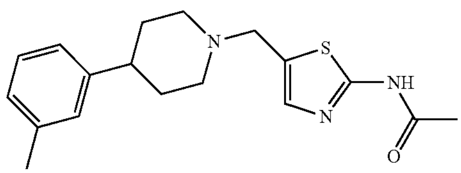 [SMILES: CC(=O)Nc1ncc(CN2CCC(c3cccc(C)c3)CC2)s1] | ++++ | ++++ | scheme 3 |
| 32 | 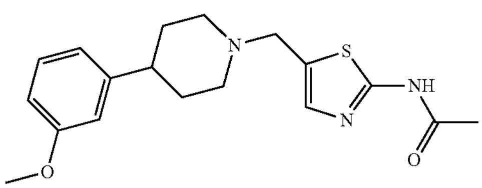 [SMILES: COc1cccc(C2CCN(Cc3cnc(NC(C)=O)s3)CC2)c1] | ++++ | +++ | scheme 3 |
| 33 | 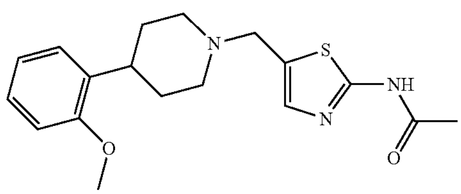 [SMILES: COc1ccccc1C1CCN(Cc2cnc(NC(C)=O)s2)CC1] | +++ | +++ | scheme 3 |
| 34 | 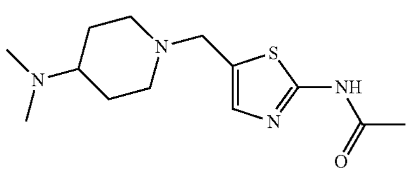 [SMILES: CC(=O)Nc1ncc(CN2CCC(N(C)C)CC2)s1] | + | | scheme 2 |
| 35 | 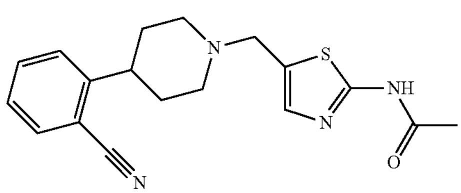 [SMILES: CC(=O)Nc1ncc(CN2CCC(c3ccccc3C#N)CC2)s1] | ++ | +++ | scheme 3 |

TABLE 1-continued

Compounds of formulae (I) and sub-formulae (IA) to (ID). OGA enzyme inhibition assay: EXAMPLE 12. Cellular O-GlcNAcylation assay: EXAMPLE 13.

| No. | Structure | hOGA enzyme inhibition (IC$_{50}$)<br>+ ≥10 μM<br>++ 1 < 10 μM<br>+++ 0.2 < 1 μM<br>++++ <0.2 μM | B35 Cell (EC$_{50}$, ICC)<br>+ 10 μM<br>++ 1 < 10 μM<br>+++ 0.2 < 1 μM<br>++++ <0.2 μM | General synthetic route |
|---|---|---|---|---|
| 36 | 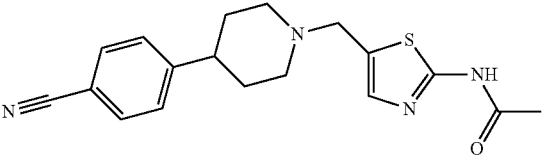 [SMILES: CC(=O)Nc1ncc(CN2CCC(c3ccc(C#N)cc3)CC2)s1] | +++ | +++ | scheme 3 |
| 37 | 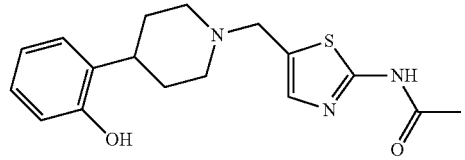 [SMILES: CC(=O)Nc1ncc(CN2CCC(c3ccccc3O)CC2)s1] | +++ | ++++ | scheme 3 |
| 38 | 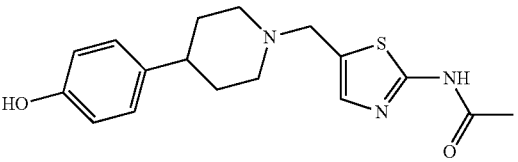 [SMILES: CC(=O)Nc1ncc(CN2CCC(c3ccc(O)cc3)CC2)s1] | ++++ | +++ | scheme 3 |
| 39 | 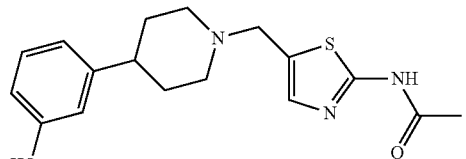 | +++ | +++ | scheme 3 |
| 40 | 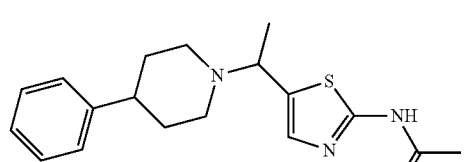 | +++ | +++ | scheme 8 |
| 41 | 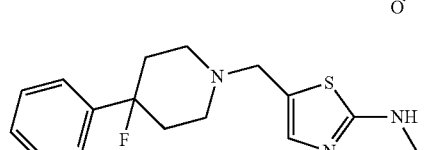 | ++ | ++ | scheme 2 |
| 42 | 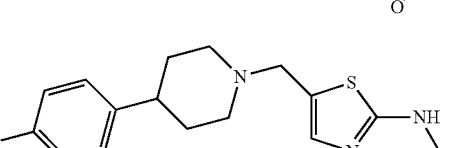 | +++ | +++ | scheme 3 |
| 43 | 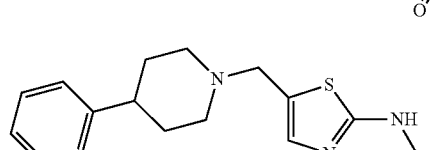 | ++ | +++ | scheme 3 |

TABLE 1-continued

Compounds of formulae (I) and sub-formulae (IA) to (ID). OGA enzyme inhibition assay: EXAMPLE 12. Cellular O-GlcNAcylation assay: EXAMPLE 13.

| No. | Structure | hOGA enzyme inhibition (IC$_{50}$) <br> + ≥10 μM <br> ++ 1 < 10 μM <br> +++ 0.2 < 1 μM <br> ++++ <0.2 μM | B35 Cell (EC$_{50}$, ICC) <br> + 10 μM <br> ++ 1 < 10 μM <br> +++ 0.2 < 1 μM <br> ++++ <0.2 μM | General synthetic route |
|---|---|---|---|---|
| 44 | 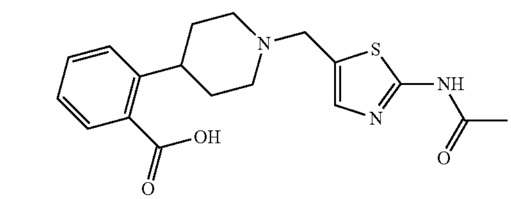 [SMILES: CC(=O)Nc1ncc(CN2CCC(c3ccccc3C(=O)O)CC2)s1] | + | | scheme 3 |
| 45 | 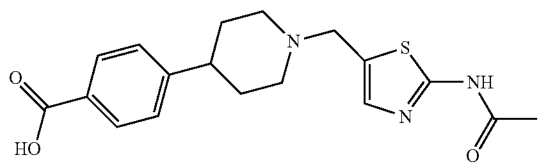 [SMILES: CC(=O)Nc1ncc(CN2CCC(c3ccc(C(=O)O)cc3)CC2)s1] | +++ | ++ | scheme 3 |
| 46 | 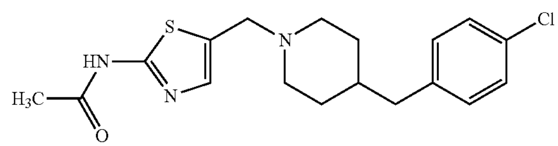 [SMILES: CC(=O)Nc1ncc(CN2CCC(Cc3ccc(Cl)cc3)CC2)s1] | ++++ | | scheme 9 |
| 47 | 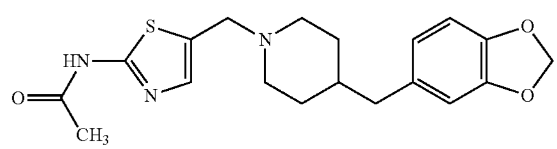 [SMILES: CC(=O)Nc1ncc(CN2CCC(Cc3ccc4c(c3)OCO4)CC2)s1] | ++++ | | scheme 10 |
| 48 | 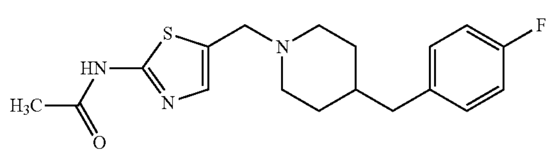 [SMILES: CC(=O)Nc1ncc(CN2CCC(Cc3ccc(F)cc3)CC2)s1] | ++++ | | scheme 9 |
| 49 | 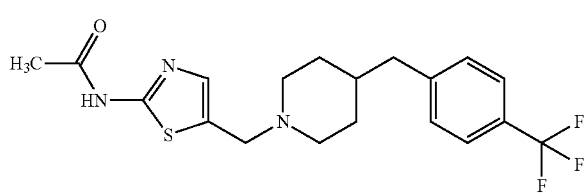 [SMILES: CC(=O)Nc1ncc(CN2CCC(Cc3ccc(C(F)(F)F)cc3)CC2)s1] | ++++ | | scheme 10 |
| 50 | 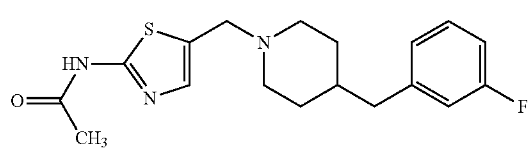 | ++++ | | scheme 10 |
| 51 | 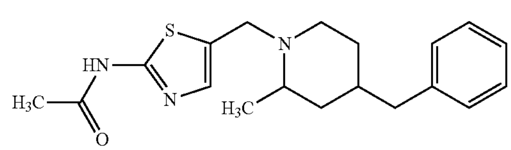 [SMILES: CC(=O)Nc1ncc(CN2CCC(Cc3ccccc3)CC2C)s1] | ++++ | | scheme 10 |

TABLE 1-continued

Compounds of formulae (I) and sub-formulae (IA) to (ID). OGA enzyme inhibition assay: EXAMPLE 12. Cellular O-GlcNAcylation assay: EXAMPLE 13.

| No. | Structure | hOGA enzyme inhibition (IC$_{50}$)<br>+ ≥10 μM<br>++ 1 < 10 μM<br>+++ 0.2 < 1 μM<br>++++ <0.2 μM | B35 Cell (EC$_{50}$, ICC)<br>+ 10 μM<br>++ 1 < 10 μM<br>+++ 0.2 < 1 μM<br>++++ <0.2 μM | General synthetic route |
|---|---|---|---|---|
| 52 | 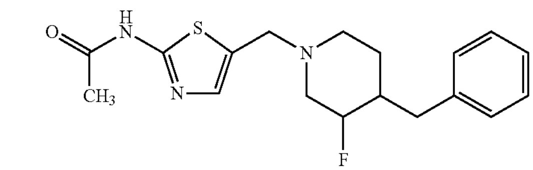 [SMILES: CC(=O)Nc1ncc(CN2CCC(Cc3ccccc3)C(F)C2)s1] | ++++ | | scheme 10 |
| 53 | 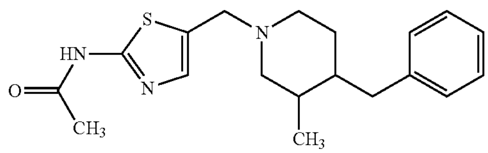 [SMILES: CC(=O)Nc1ncc(CN2CCC(Cc3ccccc3)C(C)C2)s1] | ++++ | | scheme 10 |
| 54 | 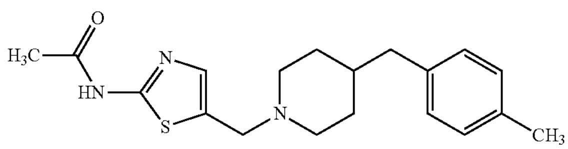 [SMILES: CC(=O)Nc1ncc(CN2CCC(Cc3ccc(C)cc3)CC2)s1] | ++++ | | scheme 10 |
| 55 | 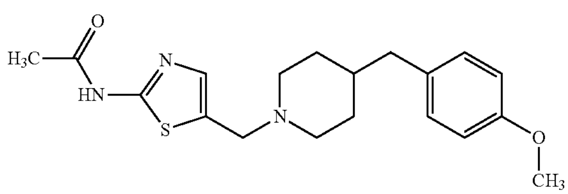 [SMILES: COc1ccc(CC2CCN(Cc3cnc(NC(C)=O)s3)CC2)cc1] | ++++ | | scheme 9 |
| 56 | 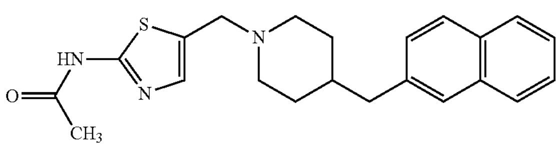 [SMILES: CC(=O)Nc1ncc(CN2CCC(Cc3ccc4ccccc4c3)CC2)s1] | ++++ | | scheme 10 |
| 58 | 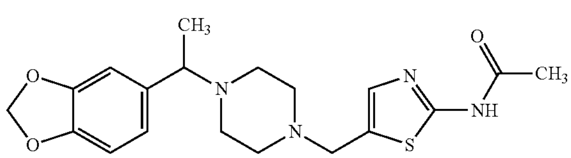 [SMILES: CC(=O)Nc1ncc(CN2CCN(C(C)c3ccc4c(c3)OCO4)CC2)s1] | ++ | | scheme 11 |
| 59 | 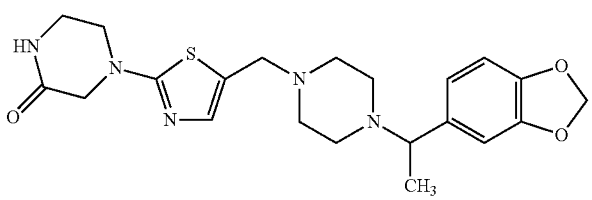 [SMILES: CC(c1ccc2c(c1)OCO2)N1CCN(Cc2cnc(N3CCNC(=O)C3)s2)CC1] | ++ | | scheme 9 |
| 61 | 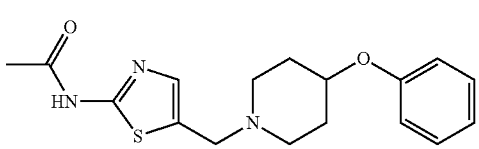 [SMILES: CC(=O)Nc1ncc(CN2CCC(Oc3ccccc3)CC2)s1] | +++ | | scheme 9 |

TABLE 1-continued

Compounds of formulae (I) and sub-formulae (IA) to (ID). OGA enzyme inhibition assay: EXAMPLE 12. Cellular O-GlcNAcylation assay: EXAMPLE 13.

| No. | Structure | hOGA enzyme inhibition (IC$_{50}$)<br>+ ≥10 μM<br>++ 1 < 10 μM<br>+++ 0.2 < 1 μM<br>++++ <0.2 μM | B35 Cell (EC$_{50}$, ICC)<br>+ 10 μM<br>++ 1 < 10 μM<br>+++ 0.2 < 1 μM<br>++++ <0.2 μM | General synthetic route |
|---|---|---|---|---|
| 62 | 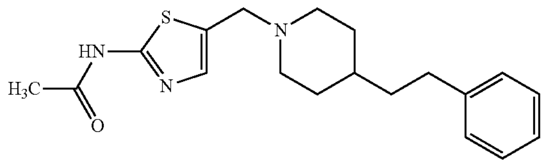 [SMILES: CC(=O)Nc1ncc(CN2CCC(CCc3ccccc3)CC2)s1] | ++++ | | scheme 9 |
| 63 | 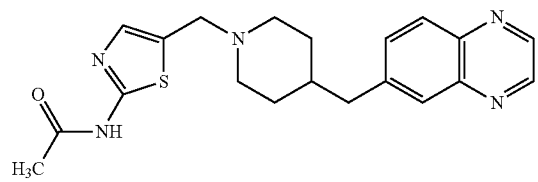 [SMILES: CC(=O)Nc1ncc(CN2CCC(Cc3ccc4nccnc4c3)CC2)s1] | ++++ | | scheme 10 |
| 64 | 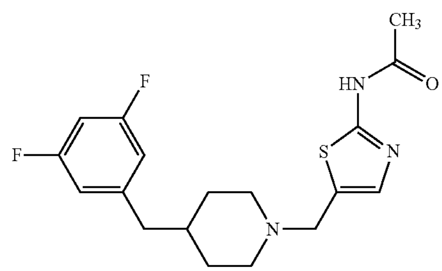 [SMILES: CC(=O)Nc1ncc(CN2CCC(Cc3cc(F)cc(F)c3)CC2)s1] | ++++ | | scheme 10 |
| 65 | 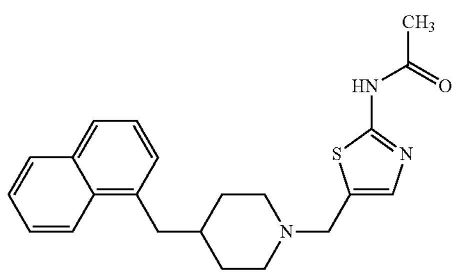 [SMILES: CC(=O)Nc1ncc(CN2CCC(Cc3cccc4ccccc34)CC2)s1] | ++++ | | scheme 10 |

The compounds according to formula (I) and the starting materials for its preparation, respectively, are produced by methods known per se, as described in the literature, i.e. under reaction conditions that are known and suitable for said reactions. Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reactions are preferably performed under basic conditions. Suitable bases are metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia), alkaline metal carbonates (e.g., sodium bicarbonate) and several organic bases (e.g., N,N-diisopropylethylamine, piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to TFA, DMF, dichloromethane, THF, H$_2$O, methanol, tert. butanol, tert. amylalcohol, triethylamine or dioxane.

Depending on the conditions used, the reaction time is between a few minutes and 14 days, the reaction temperature is between about −80° C. and 140° C., normally between −50° C. and 120° C., preferably between −20° C. and 100° C.

The present invention also relates to a process for manufacturing compounds of formula (I) comprising the steps of:

(a) reacting a compound of formula (II)

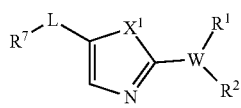
(II)

wherein $R^7$ denotes Hal, H or OH; and
$X^1$, W, $R^1$, $R^2$ and L have the meaning as defined above,
with a compound of formula (III)

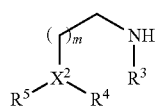
(III)

wherein $X^2$, $R^3$, $R^4$, $R^5$ and m have the meaning as defined above, to yield the compound of formula (I)

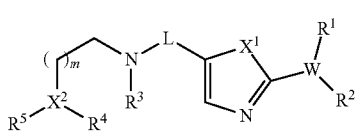
(I)

wherein $X^1$, $X^2$, W, $R^1$ to $R^5$, L and m have the meaning as defined above;

and optionally (b) converting the compound of formula (I), wherein $R^2$ is H, into another compound of formula (I), wherein $R^2$ has the meaning other than H as defined above;

(c) converting a base or an acid of the compound of formula (I) into a physiologically acceptable salt thereof; and/or (d) manifestly customizing the compound of formula (I) or the physiologically acceptable salt as medicament.

The following reactions, including without limitations schemes, conditions and compounds, are particularly preferred and included in the scope of the present invention. The radicals have the meaning as defined above.

Scheme 1: General sequence for modular coupling involving nucleophilic substitution step

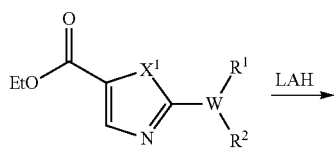

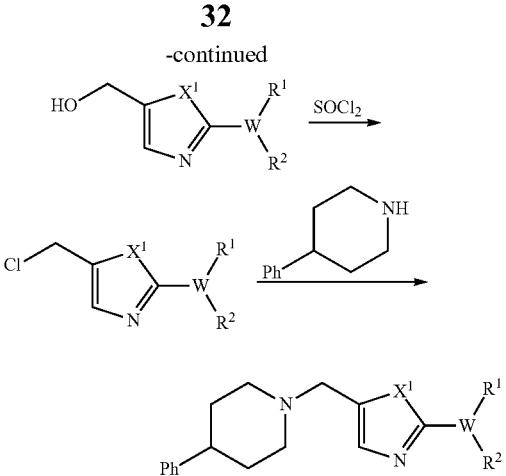

Scheme 2: General sequence for modular coupling involving reductive amination (Procedure A)

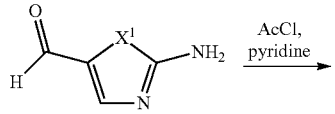

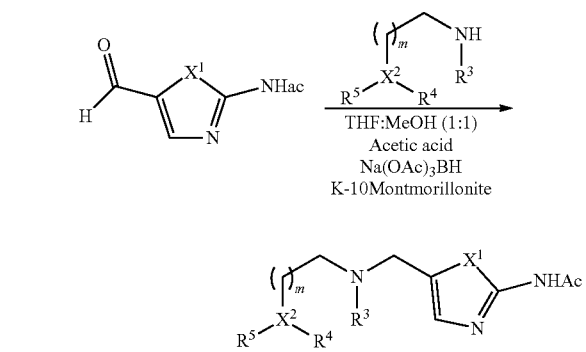

Scheme 3: General sequence for modular synthesis involving palladium-catalyzed coupling chemistry (Procedure B)

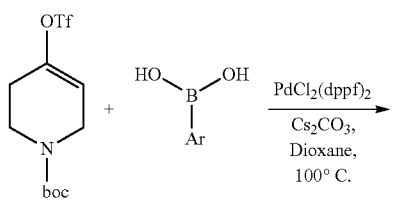

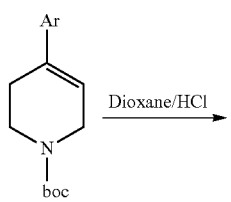

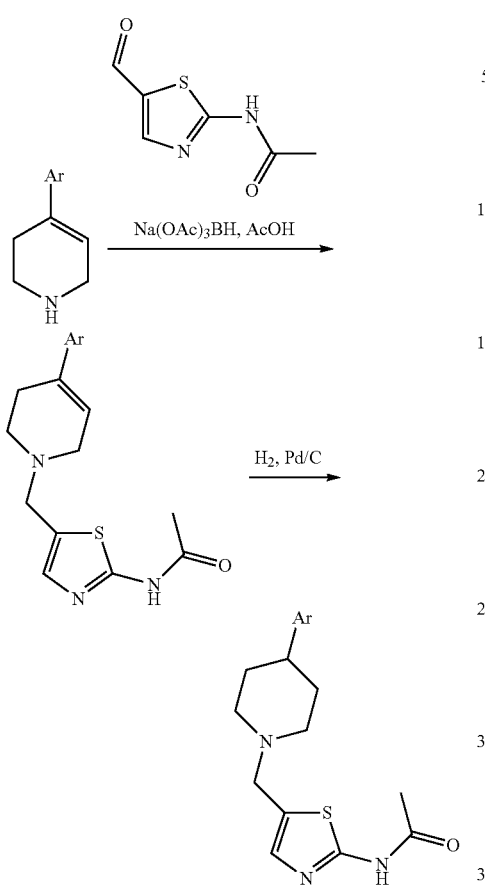
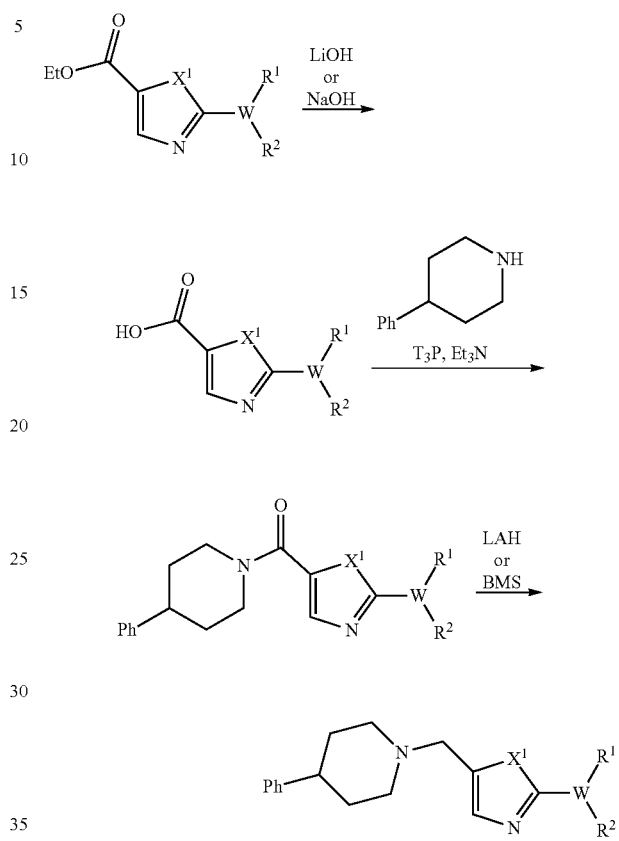
Scheme 4: General sequence for modular synthesis involving amide bond formation
Scheme 5: General routes for synthesis of heteroaryl-amides and heteroaryl-amines
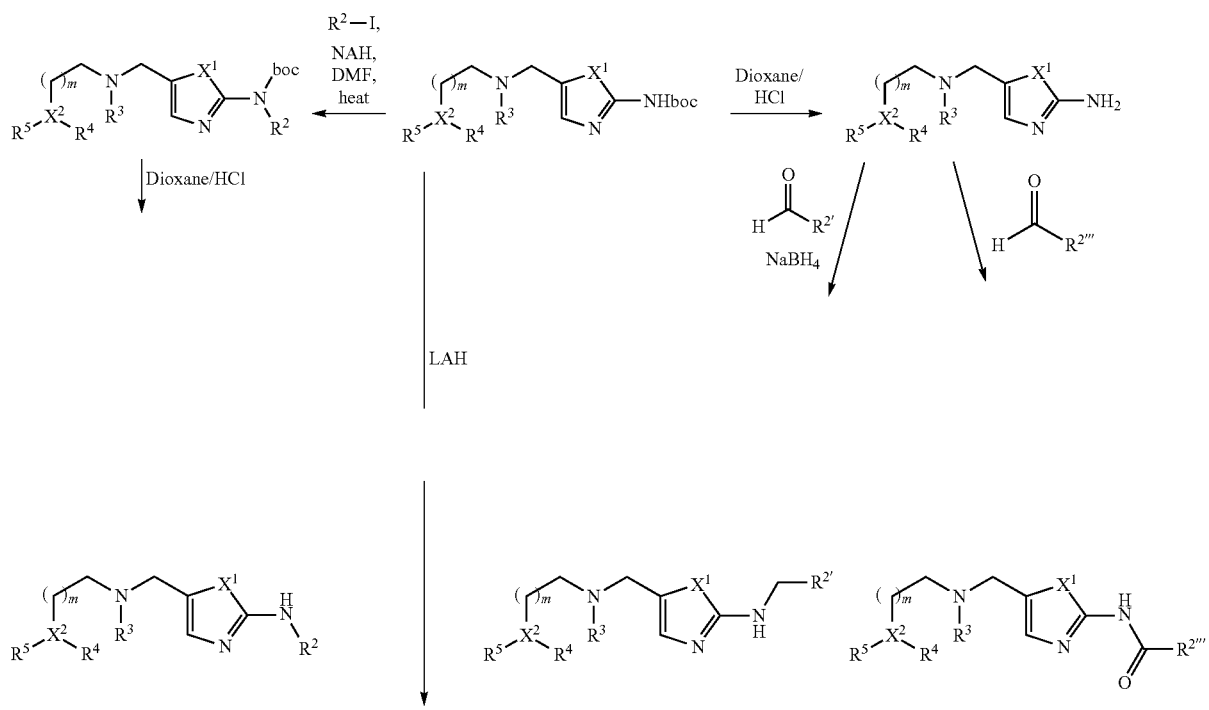

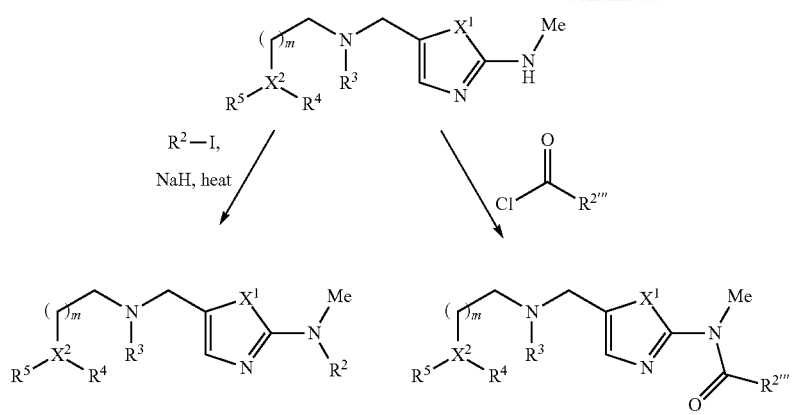
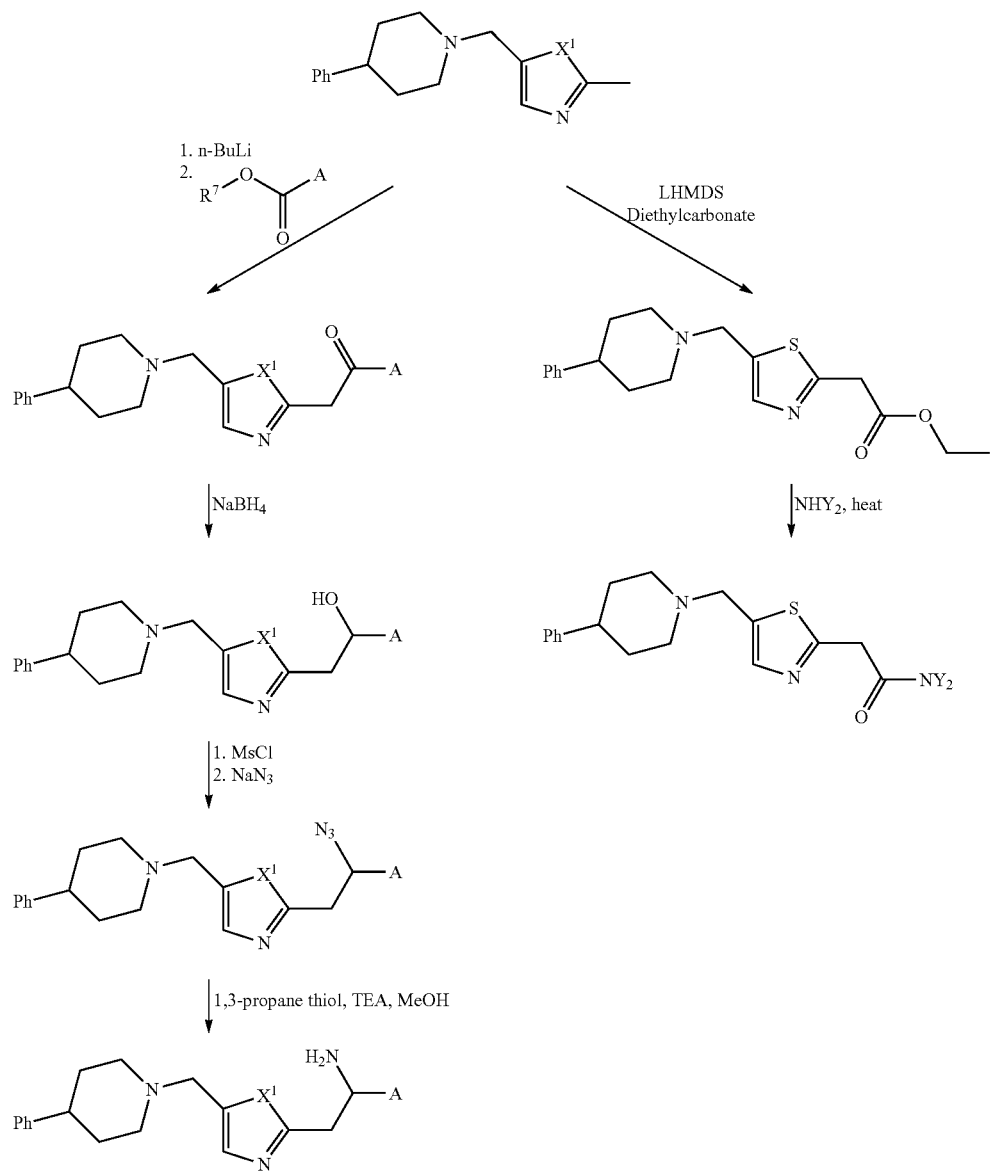
Scheme 6: General routes for synthesis of analogs containing functional groups (e.g., ketones, alcohols, and primary amines)

Scheme 7: General routes for synthesis of analogs containing functional groups (e.g., ureas, carbamates, and sulfonamides)
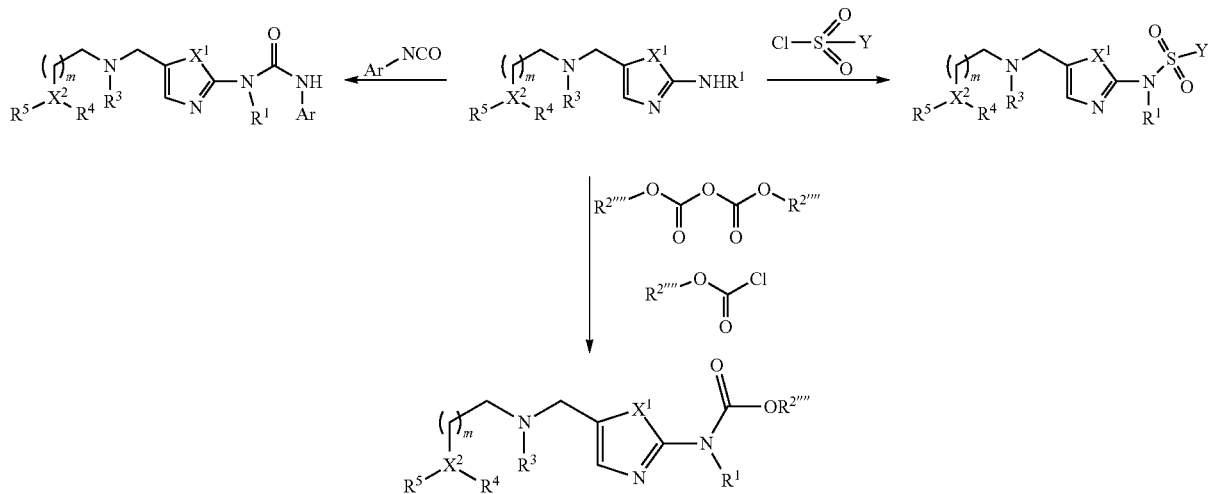
Scheme 8: Preparation of N-(5-(1-(4-phenylpiperidin-1-yl)ethyl)thiazol-2-yl)acetamide
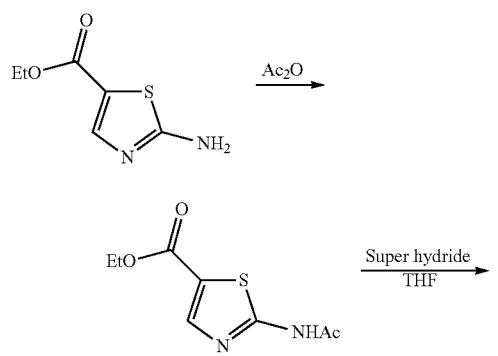
Scheme 9: General sequence for modular coupling involving nucleophilic substitution step
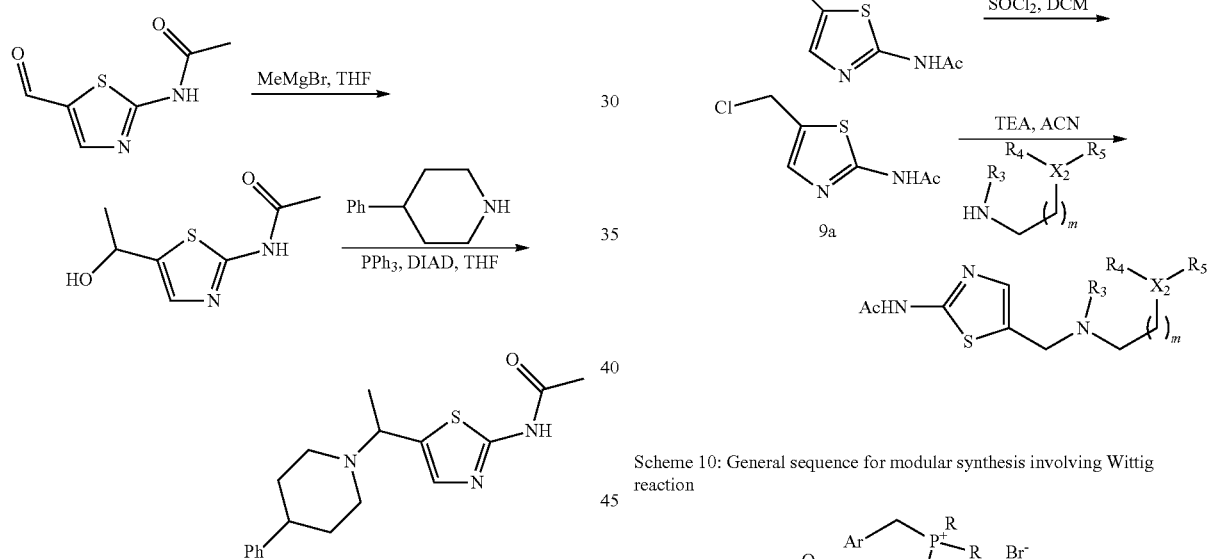
Scheme 10: General sequence for modular synthesis involving Wittig reaction
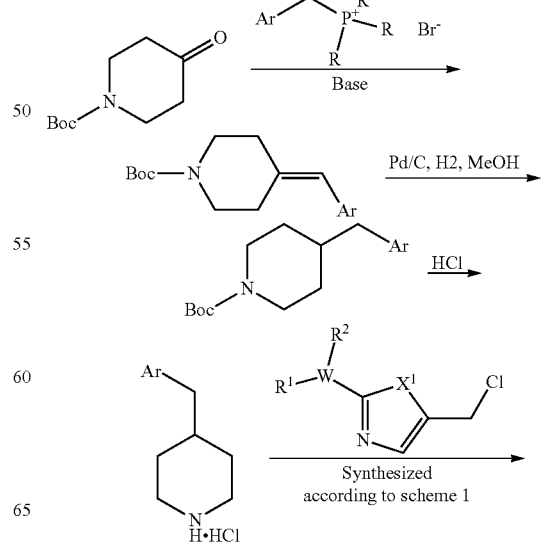

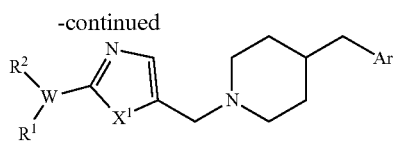

Scheme 11: General sequence for modular synthesis of benzylic substituted piperazine

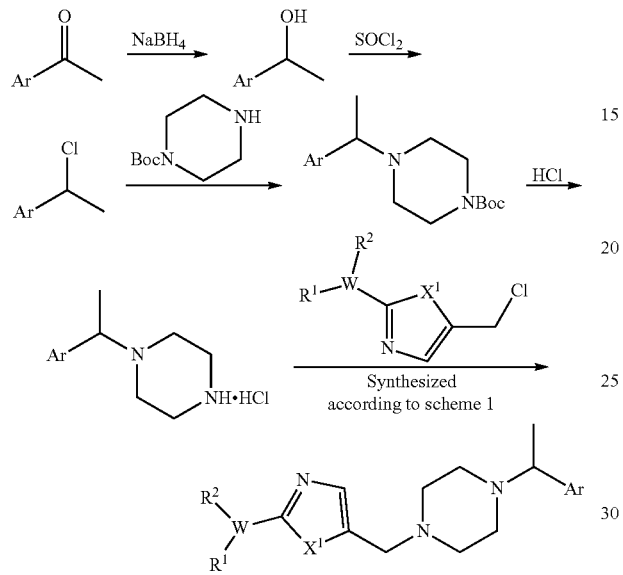

It is another object of the present invention to provide intermediate compounds of sub-formula (IE)

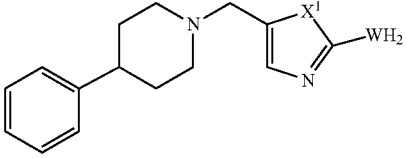

wherein $X^1$, $X^2$, W, $R^1$, $R^3$ to $R^5$, L and m have the meaning as defined above, with the proviso that the 5-pyrrolidin-1-ylmethyl-thiazol-2-ylamine is excluded. They can be preferably used as intermediates for the preparation of other compounds of formula (I) according to the invention.

It is a preferred aspect of the intermediate compounds of formula (IE) that W denotes N or CH; and $X^1$ has the meaning as defined above. Irrespective of the glucosidase inhibiting activity, particularly preferred intermediates are given in the examples below that can be used for the preparation of other compounds according to schemes 5 to 7.

More preferred intermediates are compounds of sub-formula (IE1)

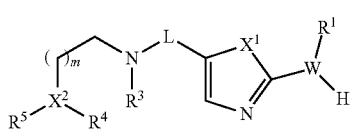

wherein W denotes N or CH; and $X^1$ and $R^1$ have the meaning as defined above.

The present invention also relates to a process for manufacturing compounds of sub-formula (IF) comprising the steps of:

(a) reacting a compound of formula (IV)

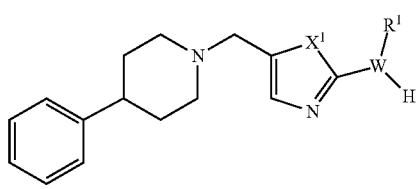

wherein W and $X^1$ have the meaning as defined above, with a compound of formula (V), (VI), (VII) or (VIII)

$$\text{(V)} \quad H\underset{O}{\overset{\|}{-}}C-R^{2'},$$

$$\text{(VI)} \quad Hal\underset{O}{\overset{\|}{-}}C-R^{2''},$$

$$\text{(VII)} \quad Hal-\underset{O}{\overset{O}{\overset{\|}{S}}}-R^{2'''} \quad \text{or}$$

$$\text{(VIII)} \quad O=C=N-R^{2''''}$$

wherein
$R^{2'}$ denotes Y, Alk, Cyc or $(CY_2)_n Ar$;
$R^{2''}$ denotes $R^{2'''}$ or $R^{2''''}$;
$R^{2'''}$ denotes Y, Alk or $(CY_2)_n Ar$;
$R^{2''''}$ denotes OY, OAlk or $O(CY_2)_n Ar$; and
Y, Alk, Cyc, Ar, Hal and n have the meaning as defined above, to yield the compound of sub-formula (IF)

$$\text{(IF)}$$

wherein
$R^1$ denotes H;
$R^2$ denotes Y, Alk, Cyc, $(CY_2)_n Ar$, COY, COAlk, $CO(CY_2)_n Ar$, CONHY, CONHAlk, $CONH(CY_2)_n Ar$, COOY, COOAlk, $COO(CY_2)_n Ar$, $SO_2Y$, $SO_2Alk$ or $SO_2(CY_2)_n Ar$; and
W and $X^1$ have the meaning as defined above;
and optionally (b) reacting the compound of sub-formula (IF) obtained in step (a) with an alkyl halide to yield another compound of formula (IF), wherein $R^1$ has the meaning other than H as defined above;
and/or (c) converting a base or an acid of the compound of sub-formula (IF) into a physiologically acceptable salt thereof.

The compounds of formula (I) and sub-formulae thereof are accessible via the routes above. The starting materials, including the compounds of formulae (II) to (VIII), are usually known to the skilled artisan, or they can be easily prepared by known methods. Accordingly, any compound of formulae (II) to (VIII) can be purified, provided as intermediate product and used as starting material for the preparation of compounds of formula (I).

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of $POCl_3$, or $SOCl_2$, $PCl_5$, $SO_2Cl_2$. In some instances oxalyl chloride is also useful. Temperatures can vary from 0° C. to reflux depending on the task to halogenate a pyridone structure or a carboxylic acid or a sulfonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like $Et_3N$, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd $(PPh_3)_4$, or $Pd(OAc)_2$, $PdCl_2$ type precursors of PdO catalysts have advanced to more complex ones with more efficient ligands. In C—C arylations, instead of boronic acids and esters, aryl-trifluoroborate potassium salts (Suzuki-Miyaura coupling), organo silanes (Hiyama coupling), Grignard reagents (Kumada), organozinc compounds (Negishi coupling) and stannanes (Stille coupling) may be useful. This experience can be transferred to N- and O-arylations. Numerous papers and methods are available and useful for the one skilled in the art in respect of N-arylation and even of electron deficient anilines, and with aryl chlorides and anilines as well as for O-arylation by using Cu and Pd catalysis.

In the final step of the processes above, a salt of the compounds, preferably those of formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by the reaction of the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

It is furthermore intended that a compound of the formula (I) includes isotope-labeled forms thereof. An isotope-labeled form of a compound of the formula (I) is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula (I) by well-known methods include isotopes of hydrogen, carbon, nitrogen, oxygen, phosphorus, fluorine and chlorine, for example $^2H$, $^3H$, $^{13}O$, $^{14}O$, $^{15}N$, $^{18}O$, $^{17}O$, $^{31}P$, $^{32}P$, $^{35}S$, $^{18}F$ and $^{36}Cl$, respectively. A compound of the formula (I), a prodrug, thereof or a pharmaceutically acceptable salt of either which contains one or more of the above-mentioned isotopes and/or other isotopes of other atoms is intended to be part of the present invention. An isotope-labeled compound of the formula (I) can be used in a number of beneficial ways. For example, an isotope-labeled compound of the formula (I) into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula (I) has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula (I) can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2H$) can also be incorporated into a compound of the formula (I) for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a compound of the formula (I) that is susceptible to oxidation, the profile of this compound in vivo can be drastically modified and result in improved pharmacokinetic properties.

When discovering and developing therapeutic agents, the person skilled in the art attempts to optimize pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula (I) with improved stability through resistance to such oxidative metabolism. Significant improvements in the pharmacokinetic profiles of compounds of the formula (I) are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula (I) which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improve-ment in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula (I) can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step.

Object of the present invention is also the use of compounds according to formula (I) and/or physiologically acceptable salts thereof for inhibiting a glycosidase. The term "inhibition" denotes any reduction in glycosidase activity, which is based on the action of the specific inventive compounds capable to interact with the target glycosidase in such a manner that makes recognition, binding and blocking possible. It shall be understood that the compounds of the invention finally interact with the target to unfold the effect. The compounds are characterized by such an appreciable affinity to at least one glycoside hydrolase which ensures a reliable binding and preferably a complete blocking of glycosidase activity. More preferably, the substances are mono-specific in order to guarantee an exclusive and directed recognition with the chosen single glycosidase target. In the context of the present invention, the term "recognition"—without being limited thereto— relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is preferably characterized by high affinity, high selectivity and minimal or even lacking cross-reactivity to other target molecules to exclude unhealthy and harmful impacts to the treated subject.

In a preferred embodiment of the present invention, the glycosidase comprises glycoside hydrolases, more preferably family 84 glycoside hydrolases, most preferably O-glycoprotein-2-acetamido-2deoxy-β-D-glucopyranosidase (OGA), highly preferably a mammalian O-GlcNAcase. It is particularly preferred that the compounds of formula (I) according to the invention selectively bind an O-GlcNAcase, e.g. thereby selectively inhibiting the cleavage of 2-acetamido-2-deoxy-β-D-glucopyranoside (O-GlcNAc) while they do not substantially inhibit a lysosomal p-hexosaminidase.

The compounds according to the invention preferably exhibit an advantageous biological activity, which is easily demonstrated in enzyme activity assays as described herein or known from prior art. In such in-vitro assays, the compounds preferably exhibit and cause an inhibitory effect. $IC_{50}$ is the concentration of a compound that produces 50% of the maximal inhibition for that compound. The glycosidase target is especially half inhibited by the compounds described herein if the concentration of the compounds amounts to less than 100 μM, preferably less than 10 μM, more preferably less than 1 μM, most preferably less than 0.2 μM.

The advantageous biological activity of the compounds according to the invention can also be demonstrated in cell-culture based assays, e.g., assays as described in WO 2008/025170. When testing compounds described herein in a cellular assay, an increase in O-GlcNAcylation (due to the inhibition of OGA) is measured. $EC_{50}$ is the effective concentration of a compound that produces 50% of the maximum possible response for that compound. The compounds of the invention exhibit $EC_{50}$ values in the range of 0.1 µM to 100 µM. It is preferred that the compounds of the invention have an activity, as expressed by an $EC_{50}$ standard, of less than 100 µM, more preferably less than 10 µM, most preferably less than 1 µM, highly preferably less than 0.2 µM.

A preferred object of the present invention relates to a method for inhibiting a glycosidase, wherein a system capable of expressing the glycosidase, particularly expressing said glycosidase, is contacted with at least one compound of formula (I) according to the invention and/or physiologically acceptable salts thereof, under conditions such that said glycosidase is inhibited. In a preferred aspect of the method, the glycosidase is contacted with a compound selectively inhibiting O-GlcNAcase and more preferably having an $IC_{50}$ of less than 0.2 µM. It is also preferred that the method is performed in-vitro and/or that the method is not practiced on the human body. A cellular system is preferred in the scope of the method. The cellular system is defined to be any subject provided that the subject comprises cells. The cell refers to any type of primary cells or genetically engineered cells, whether in the isolated status, in culture, as cell line, assembled in tissue, organs or intact laboratory mammals, provided that they are capable of expressing the glycosidase. It shall also be understood that the cell expresses the glycosidase as inherent pre-condition to put the methods of inhibition into practice. Although it is particularly preferred that the cells are capable of expressing or do express the glycosidase, it shall not be excluded that glycosidase-deficient cells can be used and the glycosidase is artificially added to the cellular system. The assay of the invention can be even completely performed in-vitro such that the cell is waived but a glycosidase is contacted with at least one compound of formula (I) according to the invention and/or physiologically acceptable salts thereof. Hence, an amount of isolated glycosidase is provided in crude or purified form for this purpose. The prior teaching of the present specification concerning the compounds of formula (I), including any preferred embodiment thereof, is valid and applicable without restrictions to the compounds according to formula (I) and their salts when used in the method for inhibiting the glycosidase.

As discussed herein, the glycosidase-signaling pathways are relevant for various diseases, preferably neurodegenerative diseases, diabetes, cancer and stress. Accordingly, the compounds according to the invention are useful in the prophylaxis and/or treatment of diseases that are dependent on the said signaling pathways by interaction with one or more of them. The present invention therefore relates to compounds according to the invention as inhibitors of the signaling pathways described herein, preferably of the OGA-mediated signaling.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate glycosidase activity, usually between about one hour and one week. In-vitro treatment can be carried out using cultivated cells from any sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing OGA-dependent signal transduction pathways in animals and/or cell culture models or in the clinical diseases mentioned in this application.

The use according to the previous paragraphs of the specification may be either performed in-vitro or in-vivo models. The inhibition can be monitored by the techniques described in the course of the present specification. The in-vitro use is preferably applied to samples of humans suffering from neurodegenerative diseases, diabetes, cancer and stress. Testing of several specific compounds and/or derivatives thereof makes the selection of that active ingredient possible that is best suited for the treatment of the human subject. The in-vivo dose rate of the chosen derivative is advantageously pre-adjusted to the glycosidase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of glycosidase activity, preferably OGA activity, if expedient.

The invention relates to a medicament comprising at least one compound according to the invention and/or pharmaceutically usable derivatives, salts, solvates and stereoisomers thereof, including mixtures thereof in all ratios. A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with OGA activity, in such a way that a pathogenic modification of their overall condition or of the condition of particular regions of the organism could establish at least temporarily.

Consequently, the invention also relates to a pharmaceutical composition comprising as active ingredient an effective amount of at least one compound of formula (I) according to the invention and/or physiologically acceptable salts thereof together with pharmaceutically tolerable adjuvants and/or excipients.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The present compounds are suitable for combination with agents known to those of skill in the art (e.g., WO 2008/025170) and are useful with the compounds of the invention.

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intra-muscular, intravenous or intradermal) methods. Such formulations can be prepared using processes known in the pharmaceutical art by, e.g., combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Accordingly, the invention also relates to a pharmaceutical composition comprising as active ingredient an effective amount of at least one compound of formula (I) according to the invention and/or physiologically acceptable salts thereof together with pharmaceutically tolerable adjuvants for oral administration, optionally in combination with at least another active pharmaceutical ingredient. The prior teaching of the present specification concerning administration route and combination product, respectively, is valid and applicable without restrictions to the combination of both features if expedient.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neurodegenerative diseases, for example Alzheimer's disease, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by OGA activity. It is particularly preferred that the diseases are neurodegenerative diseases, diabetes, cancer and stress, more preferably neurodegenerative diseases, most preferably tauopathies, highly preferably Alzheimer's disease. It shall be understood that the host of the compound is included in the present scope of protection according to the present invention.

The neurodegenerative disease or condition is more preferably selected from the group of Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supracortical gliosis, Progressive supranuclear palsy (PSP), Richardson's syndrome, Subacute sclerosing panencephalitis, Tangle-only dementia, Huntington's disease and Parkinson's disease. Most preferred is Alzheimer's disease.

The invention also relates to the use of compounds according to formula (I) and/or physiologically acceptable salts thereof for the prophylactic or therapeutic treatment and/or monitoring of diseases that are caused, mediated and/or propagated by OGA activity.

Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by OGA activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) according to the invention and/or physiologically acceptable salts thereof for use in the prophylactic or therapeutic treatment and/or monitoring of diseases that are caused, mediated and/or propagated by OGA activity. Another preferred object of the invention concerns compounds of formula (I) according to the invention and/or physiologically acceptable salts thereof for use in the prophylactic or therapeutic treatment and/or monitoring of neurodegenerative diseases, diabetes, cancer and stress. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of neurodegenerative diseases, diabetes, cancer and stress.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with OGA activity in advance or to treat the arising and continuing symptoms. The disorders as concerned by the invention are preferably neurodegenerative diseases, diabetes, cancer and stress.

In the meaning of the invention, prophylactic treatment is advisable if the subject possesses any preconditions for the aforementioned physiological or pathological conditions, such as a familial disposition, a genetic defect, or a previously passed disease.

It is another object of the invention to provide a method for treating diseases that are caused, mediated and/or propagated by OGA activity, wherein an effective amount of at least one compound of formula (I) according to the invention and/or physiologically acceptable salts thereof is administered to a mammal in need of such treatment. It is another preferred object of the invention to provide a method for treating neurodegenerative diseases, diabetes, cancer and stress, preferably a tauopathy, wherein an effective amount of at least one compound of formula (I) according to the invention and/or physiologically acceptable salts thereof is administered to a mammal in need of such treatment. The preferred treatment is an oral administration. The prior teaching of the invention and its embodiments is valid and applicable without restrictions to the methods of treatment if expedient.

In the scope of the present invention, compounds of formula (I) are provided for the first time. The low molecular weight compounds of the invention are strong and selective glycosidase inhibitors with improved passive permeability. The compounds of formula (I) have been shown to be competitive with PUGNAc, a known OGA inhibitor that binds in the substrate pocket. The endogenous substrate is an O-GlcNAcylated protein. O-GlcNAcylation of nuclear and cytoplasmic proteins is one of the most common post-translational modifications in animals and plants. O-GlcNAc cycling modulates a number of cellular processes, and evidence is mounting that dysregulation of O-GlcNAcylation plays a role in the etiology of several diseases, including Alzheimer's disease. O-GlcNAc transferase (OGT) and O-GlcNAcase (OGA) are the two enzymes that regulate O-GlcNAc cycling. Emerging data suggest that inhibitors that block OGA may help maintain healthy O-GlcNAc levels in Alzheimer's disease patients and thereby inhibit the formation of neurofibrillary tangles. Hence, the current invention comprises the use of compounds of formula (I) in the regulation, modulation and/or inhibition of the glycosidase signal cascade, which can be advantageously applied as research tool, for diagnosis and/or in treatment of any disorders that are responsive to OGA signaling and inhibition.

The low molecular weight inhibitors can be applied either themselves and/or in combination with physical measurements for diagnostics of treatment effectiveness. Medicaments and pharmaceutical compositions containing said compounds and the use of said compounds to treat glycosidase-mediated conditions is a promising, novel approach for a broad spectrum of therapies causing a direct and immediate improvement in the state of health, whether in man and animal. The impact is of special benefit to efficiently combat Alzheimer's disease, either alone or in combination with other neurodegenerative treatments.

Due to the surprisingly appreciable inhibitory activity on OGA, along with passive permeability, the compounds of the invention can be advantageously administered at lower doses compared to other less potent or selective inhibitors of prior art while still achieving equivalent or even superior desired biological effects. In addition, such a dose reduction advantageously leads to less or even no medicinal adverse effects.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All references cited herein are incorporated by reference in the disclosure of the invention.

It is to be understood that this invention is not limited to the particular compounds, pharmaceutical compositions, uses and methods described herein, as such matter can, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again provided that the technical problem of the invention is solved. Similarly, the features of any claim can be combined with the features of one or more other claims.

LIST OF ABBREVIATIONS

| | |
|---|---|
| Ac | acetyl |
| ACN | acetonitrile |
| AcOH | Acetic acid |

-continued

| | |
|---|---|
| Aq. | aqueous |
| br | broad |
| BOC | tert-butyloxycarbonyl |
| BMS | Borane dimethyl sulfide complex |
| BSA | Bovine serum albumin |
| Bu | butyl |
| Cat. | catalytic |
| δ | Chemical shift |
| d | Doublet or deuterated |
| D | deuterium |
| DCM | dichloromethane |
| dd | doublet of doublets |
| DIAD | diisopropyl azodicarboxylate |
| DIEA | N,N-Diethylamine |
| DIPEA | N,N-diisopropylethylamine |
| DMA | dimethylacetamide |
| DMAP | 4-dimethylaminopyridine |
| DMF | N,N-dimethylformamide |
| DMSO | dimethylsulfoxide |
| dppf | 1,1'-Bis(diphenylphosphino)ferrocene |
| eq. | equivalents |
| Et | ethyl |
| EtOAc | ethyl acetate |
| EtOH | ethanol |
| $^1$H | proton |
| h | hour |
| HPLC | High pressure/performance liquid chromatography |
| $IC_{50}$ | Half-maximal inhibitory concentration |
| LAH | Lithium aluminium hydride |
| LC | Liquid chromatography |
| LC/MS | Liquid chromatography coupled to mass spectrometry |
| LiHMDS | Lithium hexamethyldisilazide |
| m | multiplet |
| M | Molecular ion or mole/liter |
| Max | Lambda max |
| min | minute |
| m/z | Mass-to-charge ratio |
| MHz | megahertz |
| Me | methyl |
| min | minutes |
| MeOH | methanol |
| MS | Mass spectrometry/spectrum |
| N | Normal (unit of concentration) |
| NMO | 4-methylmorpholine N-oxide |
| NMP | N-methyl-2-pyrrolidone |
| NMR | Nuclear Magnetic Resonance |
| No. | number |
| Pet. | petroleum |
| O/N | overnight |
| PBS | Phosphate buffered saline |
| PG | Protecting group |
| Ph | phenyl |
| ppm | Parts per million |
| psi | Pounds per square inch |
| q | quartet |
| Rf | Retention factor |
| RT/rt | Room temperature |
| Rt./RT. | Retention time |
| s | Singlet |
| t | triplet |
| Tert/tert | Tertiary |
| TEA | Triethylamine |
| TFA | Trifluoroacetic acid |
| THF | Tetrahydrofuran |
| TLC | Thin layer chromatography |
| T3P | 1-Propanephosphonic Acid Cyclic Anhydride |
| UV | Ultraviolet |

Nuclear Magnetic Resonance: $^1$H NMR was recorded on a Bruker 400 MHz spectrometer, using residual signal of deuterated solvent as internal reference. Chemical shifts (δ) are reported in ppm relative to tetramethylsilane. $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

General Analytical LC Program

| Time (min) | % of mobile phase A | % of mobile phase B |
|---|---|---|
| 0 | 95 | 5 |
| 8 | 0 | 100 |
| 8.1 | 0 | 100 |
| 8.5 | 95 | 5 |
| 10 | 95 | 5 |

LC/MS Method A: This method followed the general analytical LC program, where mobile phase A was 0.1% TFA in $H_2O$ and mobile phase B was 0.1% TFA in ACN. The flow rate was 2.0 mL/min. The column was XBridge C8 (50×4.6 mm, 3.5 μm). The MS detector was used in positive mode.

LC/MS Method B: This method followed the general analytical LC program, where mobile phase A was 10 mM $NH_4HCO_3$ in $H_2O$, and mobile phase B was ACN. The flow rate was 0.8 mL/min. The column was XBridge C8 (150×4.6 mm, 3.5 μm). The MS detector was used in negative mode.

LC/MS Method C: This method followed the general analytical LC program, where mobile phase A was 0.1% TFA in $H_2O$ and mobile phase B was 0.1% TFA in ACN. The flow rate was 2.0 mL/min. The column was XBridge C8 (50×4.6 mm, 3.5 μm). The MS detector was used in positive mode.

LC/MS Method D: This method followed the general analytical LC program, where mobile phase A was 10 mM $NH_4HCO_3$ in $H_2O$, and mobile phase B was ACN. The flow rate was 1.0 mL/min. The column was XBridge C8 (50×4.6 mm, 3.5 μm). The MS detector was used in positive mode.

HPLC Method A: This method followed the general analytical LC program, where mobile phase A was 0.1% TFA in $H_2O$, and mobile phase B was 0.1% TFA in ACN. The flow rate was 2.0 mL/min. The column was XBridge C8 (50×4.6 mm, 3.5 μm). A UV detector was used.

HPLC Method B: This method followed the general analytical LC program, where mobile phase A was 10 mM $NH_4HCO_3$ in $H_2O$, and mobile phase B was ACN. The flow rate was 0.8 mL/min. The column was XBridge C8 (150×4.6 mm, 3.5 μm). A UV detector was used.

HPLC Method C: This method followed the general analytical LC program, where mobile phase A was 0.1% TFA in $H_2O$, and mobile phase B was 0.1% TFA in ACN. The flow rate was 2.0 mL/min. The column was XBridge C8 (50×4.6 mm, 3.5 μm). A UV detector was used.

HPLC Method D: This method followed the general analytical LC program, where mobile phase A was 10 mM $NH_4HCO_3$ in $H_2O$, and mobile phase B was ACN. The flow rate was 1.0 mL/min. The column was XBridge C8 (50×4.6 mm, 3.5 μm). A UV detector was used.

Chiral HPLC Method A: This method followed the general analytical LC program, where mobile phase A was 0.1% DEA in n-HEXANE: IPA 60:40. The flow rate was 1.0 mL/min. The column was CHIRALPAK AD-H (250×4.6 mm, 5 μm). A UV detector was used.

MD Auto-Prep Method B: This method followed the general analytical LC program, where mobile phase A was 0.1% TFA in $H_2O$, B-MeOH or ACN Column: Symmetry C8 (300×19 mm, 7 μm). PDA and UV detector were used.

General Preparative HPLC Methods: Preparative HPLC was performed using either a Symmetry C8 preparative column (19×300 mm, 7 μm) or a Sunfire C8 column (19×250 mm, 5 μm). Mobile phase A was either 10 mM ammonium acetate in water, or 0.1% TFA in water. Mobile phase B was either methanol or acetonitrile.

For Polar Compounds:

| Time (min) | % of mobile phase A | % of mobile phase B |
| --- | --- | --- |
| 0 | 80 | 20 |
| 20 | 20 | 80 |
| 22 | 0 | 100 |
| 25 | 0 | 100 |
| 27 | 80 | 20 |
| 30 | 80 | 20 |

For Non-Polar Compounds:

| Time (min) | % of mobile phase A | % of mobile phase B |
| --- | --- | --- |
| 0 | 80 | 20 |
| 15 | 20 | 80 |
| 20 | 0 | 100 |
| 23 | 0 | 100 |
| 25 | 80 | 20 |
| 30 | 80 | 20 |

Preparative HPLC Method C: This method followed the general analytical LC program, where mobile phase A was 0.1% TFA in $H_2O$, and mobile phase B MeOH or ACN. Column: Sunfire C8 (19×250 mm, 5 µm) or Sunfire C18 (30×250 mm, 10 µm). A UV detector was used.

Preparative HPLC Method B: This method followed the general analytical LC program, where mobile phase A was 10 mM $NH_4HCO_3$ in $H_2O$, and mobile phase B MeOH or ACN. Column: Sunfire C8 (19×250 mm, 5 µm) or Sunfire C18 (30×250 mm, 10 µm) or Sunfire C18 (30×250 mm, 10 µm). A UV detector was used.

EXAMPLE 1: PREPARATION OF 5-((4-PHENYLPIPERIDIN-1-YL)METHYL)THIAZOL-2-AMINE (INTERMEDIATE)

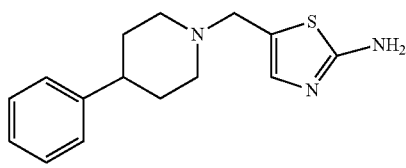 [SMILES: Nc1ncc(CN2CCC(c3ccccc3)CC2)s1]

Step 1: To a stirred solution of ethyl 2-((tert-butoxycarbonyl)amino)thiazole-5-carboxylate (5 g, 0.0183 mol) in dry THF (80 mL) at 0° C. was added $LiAlH_4$ (15 mL, 0.0309 mol, 2.0 M solution in THF) under $N_2$ dropwise. The reaction mixture was then stirred at RT for 1 h. After the completion of reaction, the reaction mixture was cooled to −10° C. to 0° C. The reaction was quenched by the dropwise addition of 10% NaOH (5 mL). After 10 min, the mixture was filtered through a pad of Celite and the filtrate was concentrated under reduced pressure to afford crude tert-butyl (5-(hydroxymethyl)thiazol-2-yl)carbamate (6 g) as a pale yellow solid. The crude product was used in the next reaction without purification. LC/MS: (Method A) 231.0 (M+H).

$^1$H NMR (DMSO-$d_6$, 400 MHz): δ 6.78 (s, 1H), 4.38 (s, 2H), 1.38 (s, 9H).

Step 2: To a solution of tert-butyl (5-(hydroxymethyl)thiazol-2-yl)carbamate (6 g, 0.026 mol) in DCM (60 mL) at 0° C. was added thionyl chloride (6.3 mL, 0.103 mol) under $N_2$, dropwise. The reaction mixture was then stirred at 0° C. for 2 h. The reaction mixture was monitored by TLC. After the completion of reaction, the reaction mixture was concentrated under reduced pressure to afford crude tert-butyl (5-(chloromethyl)thiazol-2-yl)carbamate (7 g) as brown liquid. The crude product was used in the next reaction without purification.

Step 3: A solution of tert-butyl (5-(chloromethyl)thiazol-2-yl)carbamate (7 g, 0.028 mol) in DCM (70 mL) was added to mixture of 4-phenylpiperidine (4.5 g, 0.028 mol) and $Et_3N$ (12 mL, 0.0704 mol) in DCM (50 mL). The reaction mixture was stirred at RT for 30 min. After completion of the reaction, the reaction mixture was diluted with DCM (200 mL), and washed with first water and then brine. The organic phase was dried over sodium sulfate and concentrated under reduced pressure. The crude product was re-crystallized with acetonitrile, then dried under vacuum to afford tert-butyl (5-((4-phenylpiperidin-1-yl)methyl)thiazol-2-yl)carbamate ((3.8 g) as a white solid. LC/MS: (Method A) 374.3 (M+H).

$^1$H NMR (DMSO-$d_6$, 400 MHz) δ 11.09 (bs, 1H), 7.28-7.21 (m, 4H), 7.18-7.14 (m, 2H), 3.61 (s, 2H), 2.94-2.91 (m, 2H), 2.50-2.42 (m, 1H), 2.06-2.0 (m, 2H), 1.73-1.67 (m, 4H), 1.45 (s, 9H).

Step 4: To a solution of tert-butyl (5-((4-phenylpiperidin-1-yl)methyl)thiazol-2-yl)carbamate (3.8 g) in dry dioxane (60 mL) was added HCl in dioxane (200 mL). The reaction mixture was stirred at room temperature for 12 h. After completion of the reaction, the reaction mixture was concentrated under reduced pressure to afford the hydrochloride salt of 5-((4-phenylpiperidin-1-yl)methyl)thiazol-2-amine as a white solid. Yield: (2.9 g, 92%).

$^1$H NMR (DMSO-$d_6$, 400 MHz) δ 9.46 (bs, 2H), 7.50-7.45 (d, J=19.2 Hz, 1H), 7.34-7.30 (t, J=15 Hz, 2H), 7.23-7.20 (m, 3H), 4.39 (s, 2H), 3.55-3.45 (m, 2H), 3.04-2.99 (m, 2H), 2.83-2.77 (m, 1H), 2.12-2.06 (m, 2H), 2.03-1.94 (m, 2H).

EXAMPLE 1-3: PREPARATION OF N-(5-((4-PHENYLPIPERIDIN-1-YL)METHYL)THIAZOL-2-YL)PROPIONAMIDE

To a stirred solution of 5-((4-phenylpiperidin-1-yl)methyl)thiazol-2-amine hydrochloride (100 mg, 1 eq.) in dichloromethane (5 mL) at 0° C. was added propionyl chloride (29 mg, 1 eq.), and $Et_3N$ (96 mg, 3 eq.). The reaction mixture was allowed to stir at RT for 2 h. After completion of the reaction, the reaction mixture was concentrated under reduced pressure, water was added, and the product extracted with dichloromethane. The organic phase was separated, dried over sodium sulfate, filtered and concentrated under reduced pressure. The residue was subjected to preparative HPLC to afford the trifluoroacetate salt of N-(5-((4-phenylpiperidin-1-yl)methyl)thiazol-2-yl)propionamide as an off-white solid. Yield: 35% (41 mg). LC/MS: (Method A) 330.2 (M+H). HPLC: (Method A) RT.: 3.03 min, 98.9%, (Max), 96.9% (254 nm).

$^1$H NMR (400 MHz, DMSO-$d_6$): δ 11.9 (s, 1H), 7.29-7.14 (m, 6H), 3.6 (s, 2H), 3.1 (t, J=4.0 Hz, 1H), 2.9 (d, J=8.0 Hz, 2H), 2.43-2.37 (m, 2H), 2.06-2.01 (m, 2H), 1.78-1.56 (m, 4H), 1.25-1.02 (m, 3H).

EXAMPLE 1-7: PREPARATION OF 2-METHYL-5-((4-PHENYLPIPERIDIN-1-YL)METHYL)THIAZOLE

Step 1: To a stirred solution of ethyl 2-methylthiazole-5-carboxylate (1 eq) in dry THF (5 mL) at 0° C.) under $N_2$ was added LiAlH₄ (1.1 eq., 2.0 M solution in THF) dropwise. The reaction mixture was stirred at RT for 1 h. The reaction progress was monitored by TLC. After completion of the reaction, the reaction mixture was cooled to −10° C. to 00 and then quenched by the dropwise addition of 10% NaOH aqueous solution (5 mL). After 10 min of stirring, the mixture was filtered through a pad of Celite and the filtrate was concentrated under reduced pressure to afford (2-methylthiazol-5-yl)methanol (6 g) as a pale yellow solid. The crude product used in the next step without purification. LC/MS: (Method A) 130.0 (M+H).

¹H NMR (DMSO-d₆, 400 MHz): δ 7.4 (s, 1H), 5.5 (s, 1H), 4.6 (d, J=4.0 Hz, 2H), 2.6 (s, 3H).

Step 2: To a solution of (2-methylthiazol-5-yl)methanol (1 eq) in DCM (10 mL) at 0° C. under N₂ was added thionyl chloride (3 eq), dropwise. The reaction mixture was stirred at 0° C. for 2 h. The reaction progress was monitored by TLC. After completion of the reaction, the reaction mixture was concentrated under reduced pressure to afford 5-(chloromethyl)-2-methylthiazole as a brown liquid.

Step 3: A solution of 5-(chloromethyl)-2-methylthiazole (400 mg, 1 eq.) in DCM (5 mL) was added to mixture of 4-phenylpiperidine (480 mg, 1.1 eq.) and DIPEA (1.2 eq.) in DCM (2.5 mL). The reaction mixture was stirred at RT for 1 h. After completion of the reaction, the reaction mixture was diluted with dichloromethane, and then washed consecutively with water and brine. The organic phase was dried over sodium sulfate and concentrated under reduced pressure. The residue was subjected to preparative HPLC to afford 2-methyl-5-((4-phenylpiperidin-1-yl)methyl)thiazole as a pale yellow, gummy solid. Yield: 16% (140 mg). LC/MS: (Method A) 273.0 (M+H). HPLC: (Method A) RT.: 2.71 min, 97.8%, (Max), 99.4% (254 nm).

¹H NMR (400 MHz, DMSO-d₆): δ 8.1 (s, 1H), 7.5 (s, 1H), 7.29-7.14 (m, 5H), 3.7 (s, 2H), 2.94-2.91 (m, 2H), 2.5 (s, 3H), 2.09-2.04 (m, 2H), 1.73-1.70 (m, 2H), 1.66-1.57 (m, 2H).

EXAMPLE 1-8: PREPARATION OF 2-ETHYL-5-((4-PHENYLPIPERIDIN-1-YL)METHYL)THIAZOLE

Step 1: To a solution of 2-bromo-thiazole-5-carboxylic acid ethyl ester (1 eq.) in 1,4-dioxane (5 mL) was added tributyl(vinyl)tin (1.1 eq.), followed by PdCl₂(PPh₃)₂ (10 mol %). The reaction mixture was heated to 100° C. for 14 h. After completion of the reaction, reaction mixture was filtered through a pad of Celite and the filtrate was concentrated under reduced pressure. The residue was subjected to flash chromatography to afford ethyl 2-vinylthiazole-5-carboxylate as a pale yellow, gummy solid. Yield: 65%. LC/MS: (Method A) 184.3 (M+H).

Step 2: To a solution of ethyl 2-vinylthiazole-5-carboxylate (1 eq.) in methanol: ethyl acetate (5 mL 1:1) was added 10% Pd/C. The reaction mixture was then treated with hydrogen (14 psi) at RT for 1 h. After completion of the reaction, the reaction mixture was filtered through a pad of Celite, and the filtrate was concentrated under reduced pressure. The residue was subjected to flash chromatography to afford ethyl 2-ethylthiazole-5-carboxylate as a pale yellow, gummy liquid. Yield: 60%. LC/MS: (Method A) 186.0 (M+H).

Step 3: To a stirred solution of ethyl 2-ethylthiazole-5-carboxylate (1 eq.) in dry THF (5 mL) at 0° C. under N₂ was added LiAlH₄ (1.1 eq., 2.0 M solution in THF), dropwise. The reaction mixture was then stirred at RT for 1 h. After completion of the reaction (as monitored by TLC), the reaction mixture was cooled to −10° C.-0° C. The reaction was quenched by the dropwise addition of 10% NaOH (5 mL). After 10 min, the mixture was filtered through a pad of Celite, and the filtrate was concentrated under reduced pressure to afford (2-ethylthiazol-5-yl)methanol (6 g) as a pale yellow solid. To the crude product (1 eq.) in DCM (5 mL) at 0° C. under N₂ was added thionyl chloride (3 eq.) dropwise. The reaction mixture was then stirred at 0° C. for 2 h. After the completion of reaction, as monitored by TLC, the reaction mixture was concentrated under reduced pressure to afford 5-(chloromethyl)-2-ethylthiazole as a brown liquid. The crude product was used in the next reaction without purification. Yield: 40%. LC/MS: (Method A) 148.0 (M+H).

Step 4: A solution of 5-(chloromethyl)-2-ethylthiazole (300 mg, 1 eq.) in DCM (5 mL) was added to mixture of 4-phenypiperdine (328 mg, 1.1 eq.) and DIPEA (526 mg, 2 eq.) in DCM (5 mL). The reaction mixture was stirred at RT for 1 h. After completion of the reaction, the reaction mixture was diluted with DCM, and then washed consecutively with water and brine. The organic phase was dried over sodium sulfate and concentrated under reduced pres-

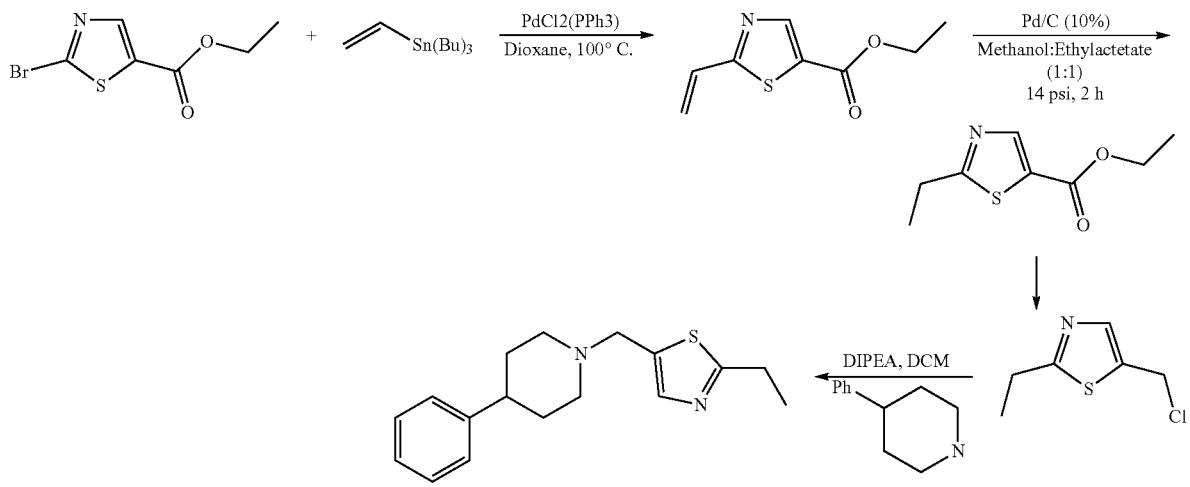

sure. The residue was subjected to preparative HPLC to afford 2-ethyl-5-((4-phenylpiperidin-1-yl)methyl)thiazole as a pale yellow gummy solid. Yield: 27% (145 mg). LC/MS: (Method A) 287.0 (M+H). HPLC: (Method A) RT.: 3.02 min, 99.8%, (Max), 99.5% (254 nm).

$^1$H NMR (400 MHz, DMSO-d$_6$): δ 7.5 (s, 1H), 7.29-7.14 (m, 5H), 3.7 (s, 1H), 2.95-2.80 (m, 4H), 2.50-2.43 (m, 1H), 2.08-2.02 (m, 2H), 1.73-1.59 (m, 4H), 1.3 (t, J=8.0 Hz, 3H).

EXAMPLE 2: SCHEME 2 (PROCEDURE A)

Step 1: To a stirred solution of 2-formyl-5-amino thiazole (1 eq.) in dry pyridine at 0° C. was added CH$_3$COCl (1.2 eq.) dropwise for 10 min. After the addition, the reaction was allowed to stir at RT for 12 h. After completion of the reaction, the reaction mixture was evaporated under reduced pressure and H$_2$O was added to get a precipitate which was filtered and air dried to afford the product.

Step 2: To a stirred solution of N-(5-formyl-thiazol-2-yl)-acetamide (1 eq.) in THF/methanol (1:1) at RT, was added catalytic CH$_3$COOH, substituted amine (1.1 eq.), K-10 Montmorillonite and Na(OAc)$_3$BH (1 eq.). The reaction mixture was then heated to 90° C. for 12 h. After completion of the reaction, the reaction mixture was filtered through a Celite bed and the filtrate was concentrated to afford the crude product which was purified by column chromatography to afford the desired product.

EXAMPLE 2-15: PREPARATION OF N-[5-(4-METHYL-PIPERIDIN-1-YLMETHYL)-THIAZOL-2-YL]-ACETAMIDE

Following Procedure A, N-(5-formyl-thiazol-2-yl)-acetamide (0.1 g, 0.58 mmol) and 4-methylpiperidine (172 mg, 1.76 mmol) were used to afford N-[5-(4-methyl-piperidin-1-ylmethyl)-thiazol-2-yl]-acetamide. Purification of the product by preparative HPLC afforded the trifluoroacetate salt of N-[5-(4-methyl-piperidin-1-ylmethyl)-thiazol-2-yl]-acetamide as a white solid. Yield: 20% (46 mg). LC/MS: (Method A) 254.2 (M+H). HPLC: (Method A) RT.: 1.72 min, 99.8%, (Max), 99.4% (254 nm).

$^1$H NMR (400 MHz, DMSO-d$_6$): δ 12.30 (s, 1H), 9.50 (s, 1H), 7.58 (d, J=5.8 Hz, 1H), 4.58-4.47 (m, 2H), 3.48-3.35 (m, 2H), 2.90-2.82 (m, 2H), 2.15 (s, 3H), 1.81-1.78 (m, 2H), 1.56-1.55 (m, 1H), 1.36-1.32 (m, 2H), 0.97-0.94 (m, 3H).

EXAMPLE 2-19: PREPARATION OF N-[5-(4-PHENYL-PIPERAZIN-1-YLMETHYL)-THIAZOL-2-YL]-ACETAMIDE

Following Procedure A, N-(5-formyl-thiazol-2-yl)-acetamide (0.1 g, 0.58 mmol) and 4-phenylpiperazine (234 mg, 1.76 mmol) were used to afford N-[5-(4-phenyl-piperazin-1-ylmethyl)-thiazol-2-yl]-acetamide as a white solid. Yield: 7% (10 mg). LC/MS: (Method A) 317.3 (M+H). HPLC: (Method A) RT.: 2.41 min, 98.5%, (Max), 97.4% (254 nm).

$^1$H NMR (400 MHz, DMSO-d$_6$): δ 11.96 (s, 1H), 7.27 (s, 1H), 7.20-7.16 (m, 2H), 6.90 (d, J=8.0 Hz, 2H), 6.76-6.73 (m, 1H), 3.66 (s, 2H), 3.10 (d, J=8.0 Hz, 4H), 2.50-2.48 (m, 4H), 2.10 (s, 3H).

EXAMPLE 2-20: PREPARATION OF N-{5-[(3-PHENYL-PROPYLAMINO)-METHYL]-THIAZOL-2-YL}-ACETAMIDE

Following Procedure A, N-(5-formyl-thiazol-2-yl)-acetamide (0.1 g, 0.58 mmol) and 3-phenyl-propyl-amine (234 mg, 1.76 mmol) were used to afford N-{5-[(3-phenyl-propylamino)-methyl]-thiazol-2-yl}-acetamide. Purification of the product by preparative HPLC gave the trifluoroacetate salt of N-{5-[(3-phenyl-propylamino)-methyl]-thiazol-2-yl}-acetamide as an off-white solid. Yield: 13% (16 mg). LC/MS: (Method A) 290.2 (M+H). HPLC: (Method A) RT.: 2.41 min, 98.2%, (Max), 94.8% (254 nm).

$^1$H NMR (400 MHz, DMSO-d$_6$): δ 12.22 (s, 1H), 8.78 (s, 2H), 7.51 (s, 1H), 7.31-7.18 (m, 5H), 4.35 (s, 2H), 2.89-2.86 (m, 2H), 2.65-2.61 (m, 2H), 2.15 (s, 3H), 1.90-1.86 (m, 2H).

EXAMPLE 2-21: PREPARATION OF N-(5-{[METHYL-(3-PHENYL-PROPYL)-AMINO]-METHYL}-THIAZOL-2-YL)-ACETAMIDE

Following the Procedure A, N-(5-formyl-thiazol-2-yl)-acetamide (0.1 g, 0.58 mmol) and methyl-(3-phenyl-propyl)-amine (261 mg, 1.76 mmol) were used to afford N-(5-{[methyl-(3-phenyl-propyl)-amino]-methyl}-thiazol-2-yl)-acetamide. Purification of the product by preparative HPLC afforded the trifluoroacetate salt of N-(5-{[methyl-(3-phenyl-propyl)-amino]-methyl}-thiazol-2-yl)-acetamide as a white solid. Yield: 13% (29 mg). LC/MS: (Method A) 304.3 (M+H). HPLC: (Method A) RT.: 2.62 min, 99.2%, (Max), 97.4% (254 nm).

$^1$H NMR (400 MHz, DMSO-d$_6$): δ 11.94 (s, 1H), 7.26-7.12 (m, 6H), 3.60-3.58 (m, 2H), 2.58-2.48 (m, 2H), 2.32-2.28 (m, 2H), 2.13-2.10 (m, 6H), 1.73-1.70 (m, 2H).

EXAMPLE 2-22: PREPARATION OF N-[5-(3-PHENYL-AZETIDIN-1-YLMETHYL)-THIAZOL-2-YL]-ACETAMIDE

Following Procedure A, N-(5-formyl-thiazol-2-yl)-acetamide (0.1 g, 0.58 mmol) and 3-phenylazetidine (231 mg, 1.76 mmol) were used to afford the N-[5-(3-phenyl-azetidin-1-ylmethyl)-thiazol-2-yl]-acetamide as a pale yellow solid. Yield: 31% (48 mg). LC/MS: (Method A) 288.0 (M+H). HPLC: (Method A) RT.: 2.26 min, 97.7%, (Max), 98.9% (254 nm).

$^1$H NMR (400 MHz, DMSO-d$_6$): δ 11.74 (s, 1H), 7.35-7.23 (m, 6H), 3.83-3.76 (m, 5H), 3.26-3.23 (m, 2H), 2.32 (s, 3H).

EXAMPLE 2-23: PREPARATION OF N-[5-(4-CYANO-4-PHENYL-PIPERIDIN-1-YLMETHYL)-THIAZOL-2-YL]-ACETAMIDE

Following Procedure A, N-(5-formyl-thiazol-2-yl)-acetamide (0.1 g, 0.58 mmol) and 4-phenyl-piperidin-4-carbonitrile (323 mg, 1.76 mmol) were used to afford N-[5-(4-cyano-4-phenyl-piperidin-1-ylmethyl)-thiazol-2-yl]-acetamide as an off-white solid. Yield: 27% (48 mg). LC/MS: (Method A) 341.2 (M+H). HPLC: (Method A) RT.: 2.66 min, 99.6%, (Max), 99.8% (254 nm).

$^1$H NMR (400 MHz, DMSO-d$_6$): δ 11.98 (s, 1H), 7.54-7.51 (m, 2H), 7.44-7.40 (m, 2H), 7.37-7.30 (m, 2H), 3.73 (s, 2H), 2.98 (d, J=12.0 Hz, 2H), 2.36-2.30 (m, 2H), 2.12-2.10 (m, 5H), 2.09-2.02 (m, 2H).

EXAMPLE 2-24: PREPARATION OF N-[5-(4-HYDROXY-4-PHENYL-PIPERIDIN-1-YLMETHYL)-THIAZOL-2-YL]-ACETAMIDE

Following Procedure A, N-(5-formyl-thiazol-2-yl)-acetamide (0.1 g, 0.58 mmol) and 4-phenyl-piperidin-4-ol (307 mg, 1.76 mmol) were used to afford N-[5-(4-hydroxy-4- phenyl-piperidin-1-ylmethyl)-thiazol-2-yl]-acetamide as a pale brown solid. Yield: 31% (16 mg). LC/MS: (Method A) 332.2 (M+H). HPLC: (Method A) RT.: 2.11 min, 96.2%, (Max), 96.6% (254 nm).

$^1$H NMR (400 MHz, DMSO-d$_6$): δ 11.95 (s, 1H), 7.47 (d, J=7.4 Hz, 2H), 7.31-7.17 (m, 3H), 4.77 (s, 1H), 3.66 (s, 2H), 2.66-2.62 (m, 2H), 2.49-2.40 (m, 2H), 2.10 (s, 3H), 1.92-1.87 (m, 2H), 1.58-1.55 (m, 2H).

EXAMPLE 2-25: PREPARATION OF N-(5-PIPERIDIN-1-YLMETHYL-THIAZOL-2-YL)-ACETAMIDE

Following Procedure A, N-(5-formyl-thiazol-2-yl)-acetamide (0.1 g, 0.58 mmol) and piperidine (370 mg, 1.76 mmol) were used to afford N-(5-piperidin-1-ylmethyl-thiazol-2-yl)-acetamide as a pale brown solid. Yield: 14% (18 mg). LC/MS: (Method A) 240.2 (M+H). HPLC: (Method A) RT.: 2.31 min, 97.7%, (Max), 98.6% (254 nm).

$^1$H NMR (400 MHz, DMSO-d$_6$): δ 11.94 (s, 1H), 7.22 (s, 1H), 3.57-3.52 (m, 2H), 2.32-2.31 (m, 4H), 2.11 (s, 3H), 1.90-1.36 (m, 6H).

EXAMPLE 2-26: PREPARATION OF N-[5-(4-ISOPROPYLPIPERIDIN-1-YLMETHYL)THIAZOL-2-YL]-ACETAMIDE

Following Procedure A, N-(5-formyl-thiazol-2-yl)-acetamide (0.1 g, 0.58 mmol) and 4-isopropylpiperidine (220 mg, 1.76 mmol) were used to afford N-[5-(4-isopropylpiperidin-1-ylmethyl)thiazol-2-yl]-acetamide as an off-white solid. Yield: 23% (33 mg). LC/MS: (Method A) 282.2 (M+H). HPLC: (Method A) RT.: 2.57 min, 98.8%, (Max), 96.6% (254 nm).

$^1$H NMR (400 MHz, DMSO-d$_6$): δ 11.93 (s, 1H), 7.22 (s, 1H), 3.56 (s, 2H), 2.85-2.83 (m, 2H), 2.09 (s, 3H), 1.87-1.81 (m, 2H), 1.58-1.55 (m, 2H), 1.40-1.33 (m, 1H), 1.24-1.23 (m, 2H), 0.96-0.85 (m, 7H).

EXAMPLE 2-27: PREPARATION OF N-(5-((4-CYCLOHEXYLPIPERIDIN-1-YL)METHYL)THIAZOL-2-YL)ACETAMIDE

Following Procedure A, N-(5-formyl-thiazol-2-yl)-acetamide (0.1 g, 0.58 mmol) and 4-cyclohexylpiperdine (290 mg, 1.76 mmol) were used to afford N-(5-((4-cyclohexylpiperidin-1-yl)methyl)thiazol-2-yl)acetamide. The product was subjected to preparative HPLC to afford the trifluoroacetate salt of N-(5-((4-cyclohexylpiperidin-1-yl)methyl)thiazol-2-yl) as an off-white solid. Yield: 10% (19 mg). LC/MS: (Method A) 322.3 (M+H). HPLC: (Method A) RT.: 3.34 min, 98.2%, (Max), 95.2% (254 nm).

$^1$H NMR (400 MHz, DMSO-d$_6$): δ 12.30 (s, 1H), 9.44 (s, 1H), 7.60-7.55 (m, 1H), 4.47 (d, J=4.0 Hz, 2H), 3.40-3.37 (m, 2H), 2.88-2.50 (m, 2H), 2.15 (s, 3H), 1.84-1.81 (m, 2H), 1.74-1.61 (m, 6H), 1.39-1.32 (m, 8H), 0.98-0.96 (m, 2H).

EXAMPLE 2-28: PREPARATION OF N-(5-((4-BENZYLPIPERIDIN-1-YL)METHYL)THIAZOL-2-YL)ACETAMIDE

Following Procedure A, N-(5-formyl-thiazol-2-yl)-acetamide (0.1 g, 0.58 mmol) and 4-benzylpiperdine (304 mg, 1.76 mmol) to afford N-(5-((4-benzylpiperidin-1-yl)methyl) thiazol-2-yl)acetamide as a white solid. Yield: 18% (31 mg). LC/MS: (Method A) 330.2 (M+H). HPLC: (Method A) RT.: 3.00 min, 98.9%, (Max), 98.1% (254 nm).

$^1$H NMR (400 MHz, DMSO-d$_6$): δ 11.92 (s, 1H), 7.26-7.12 (m, 6H), 3.55 (s, 2H), 2.79-2.76 (m, 2H), 1.97 (s, 3H), 1.86-1.81 (m, 2H), 1.52-1.42 (m, 3H), 1.32-1.22 (m, 2H).

EXAMPLE 2-29: PREPARATION OF N-(5-((3-PHENYLPIPERIDIN-1-YL)METHYL)THIAZOL-2-YL)ACETAMIDE

Following Procedure A, N-(5-formyl-thiazol-2-yl)-acetamide (0.1 g, 0.58 mmol) and 3-phenylpiperdine (280 mg, 1.76 mmol) were used to afford N-(5-((3-phenylpiperidin-1-yl)methyl)thiazol-2-yl)acetamide as a brown solid. Yield: 13% (22 mg). LC/MS: (Method A) 316.2 (M+H). HPLC: (Method A) RT. 2.68 min, 99.3%, (Max), 98.2% (254 nm).

$^1$H NMR (400 MHz, DMSO-d$_6$): δ 11.94 (s, 1H), 7.28-7.17 (m, 6H), 3.64 (s, 2H), 2.85-2.83 (m, 2H), 2.74-2.71 (m, 1H), 2.09 (s, 3H), 2.00-1.95 (m, 2H), 1.77-1.68 (m, 2H), 1.54-1.42 (m, 2H).

EXAMPLE 2-34: PREPARATION OF N-(5-((4-(DIMETHYLAMINO)PIPERIDIN-1-YL)METHYL)THIAZOL-2-YL)ACETAMIDE

Following Procedure A, N-(5-((4-(dimethylamino)piperidin-1-yl)methyl)thiazol-2-yl)acetamide was synthesized from N-(5-formyl-thiazol-2-yl)-acetamide (0.1 g, 0.58 mmol) and N,N-dimethylpiperidin-4-amine (222 mg, 1.76 mmol) as a white gummy solid. Yield: 15% (20 mg, White Gummy Solid). LC/MS: (Method A) 283.3 (M+H). HPLC: (Method A) RT.: 3.20 min, 98.4%, (Max), 97.9% (254 nm).

$^1$H NMR (400 MHz, DMSO-d$_6$): δ 11.96 (s, 1H), 7.24 (s, 1H), 3.61 (s, 2H), 2.89 (d, J=8.0 Hz, 2H), 2.31 (s, 3H), 2.10-1.81 (m, 4H), 1.47-1.42 (m, 2H), 0.56-0.10 (m, 6H).

EXAMPLE 2-41: PREPARATION OF N-[5-(4-FLUORO-4-PHENYL-PIPERIDIN-1-YLMETHYL)-THIAZOL-2-YL]-ACETAMIDE

Following Procedure A, N-(5-formyl-thiazol-2-yl)-acetamide (0.1 g, 0.58 mmol) and 4-fluoro-4-phenyl-piperidine (311 mg, 1.76 mmol) were used to afford N-[5-(4-fluoro-4-phenyl-piperidin-1-ylmethyl)-thiazol-2-yl]-acetamide as a white solid. Yield: 25% (10 mg). LC/MS: (Method A) 334.0 (M+H). HPLC: (Method A) RT.: 2.80 min, 99.8%, (Max), 99.6% (254 nm).

$^1$H NMR (400 MHz, DMSO-d$_6$): δ 11.97 (s, 1H), 7.43-7.29 (m, 6H), 3.70 (s, 2H), 2.79 (d, J=8.0 Hz, 2H), 2.35-2.30 (m, 2H), 2.10-2.09 (m, 5H), 1.87-1.86 (m, 2H).

EXAMPLE 3: SCHEME 3 (PROCEDURE B)

Step 1: To a stirred solution of 4-trifluoromethanesulfonyloxy-3, 6-dihydro-2H-pyridine-1-carboxylic acid tert-butyl ester (1 eq.) in dry degassed dioxane was added substituted boronic acid (1.2 eq.), Cs$_2$CO$_3$ (1.5 eq) and finally PdCl$_2$(dppf)$_2$ (6 mol %). The reaction mixture was heated to 100° C. for 14 h. After completion of the reaction, the reaction mixture was filtered through a Celite bed and the filtrate was evaporated under reduced pressure and purified by column chromatography to afford the product.

Steps 2 and 3: To a stirred solution of 4-substituted phenyl-3,6-dihydro-2H-pyridine-1-carboxylic acid tert-butyl ester (1 eq.) in dioxane at 0° C. was added Dioxane/HCl (2 mL) and allowed to stir at RT for 4 h. After completion of reaction, the reaction mixture was concentrated to afford the product which was used as such for the next step without further purification. The crude reaction mixture was (1 eq.) dissolved in THF: MeOH (1:1), catalytic CH$_3$COOH, crude 4-substituted phenyl-1,2,3,6-tetra hydro-pyridine (1.1 eq.), K-10 Montmorillonite (1 eq.) and Na(OAc)$_3$BH (1.2 eq.) was added and heated to 90° C. for 12 h. After completion of reaction, the reaction mixture was filtered through a Celite bed and the filtrate was concentrated to afford the crude product.

Step 4: The product from Procedure B Step 3 was dissolved in methanol (10 mL) and subjected to hydrogenation using 10% Pd/C and H$_2$ (14 psi) for 4 h to 12 h. After completion of the reaction, the reaction mixture was filtered through a Celite bed; the filtrate was evaporated and concentrated. The crude product was purified both by Column Chromatography and preparative HPLC to afford the product.

EXAMPLE 3A: PREPARATION OF TERT-BUTYL 4-(2-FLUOROPHENYL)-5,6-DIHYDRO-PYRIDINE-1(2H)-CARBOXYLATE (INTERMEDIATE)

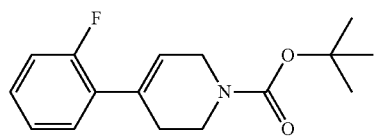 [SMILES: CC(C)(C)OC(=O)N1CC=C(c2ccccc2F)CC1]

Tert-butyl 4-(2-fluorophenyl)-5,6-dihydropyridine-1 (2H)-carboxylate was prepared using 2-fluorophenylboronic acid (300 mg, 1 mmol) and 4-trifluoromethanesulfonyloxy-3,6-dihydro-2H-pyridine-1-carboxylic acid tert-butyl ester (704 mg, 1.1 mmol) as a brown gummy solid (369 mg, 62%) following Procedure B Step 1. LC/MS: (Method A) 278.2 (M+H).

EXAMPLE 3B: PREPARATION OF 4-(4-FLUORO-PHENYL)-3,6-DIHYDRO-2H-PYRIDINE-1-CARBOXYLIC ACID TERT-BUTYL ESTER (INTERMEDIATE)

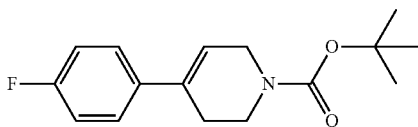 [SMILES: CC(C)(C)OC(=O)N1CC=C(c2ccc(F)cc2)CC1]

(4-(4-Fluoro-phenyl)-3,6-dihydro-2H-pyridine-1-carboxylic acid tert-butyl ester was prepared using 4-fluorophenylboronic acid (300 mg, 1 mmol) and 4-trifluoromethanesulfonyloxy-3,6-dihydro-2H-pyridine-1-carboxylic acid tert-butyl ester (704 mg, 1.1 mmol) as a brown solid (405 mg, 68%) following Procedure B Step 1. LC/MS: (Method A) 278.2 (M+H).

EXAMPLE 3C: PREPARATION OF 4-P-TOLYL-3,6-DIHYDRO-2H-PYRIDINE-1-CARBOXYLIC ACID TERT-BUTYL ESTER (INTERMEDIATE)

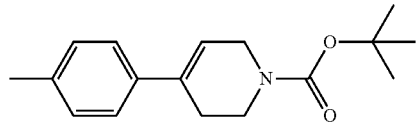 [SMILES: Cc1ccc(C2=CCN(C(=O)OC(C)(C)C)CC2)cc1]

4-p-Tolyl-3,6-dihydro-2H-pyridine-1-carboxylic acid tert-butyl ester was prepared using 4-methyl phenylboronic acid (400 mg, 1 mmol) and 4-trifluoro methanesulfonyloxy-3,6-dihydro-2H-pyridine-1-carboxylic acid tert-butyl ester (1 g, 1.1 mmol) as a gummy liquid (312 mg, 52%) following Procedure B Step 1. LC/MS: (Method A) 274.2 (M+H).

EXAMPLE 3D: PREPARATION OF TERT-BUTYL 4-(M-TOLYL)-5,6-DIHYDROPYRIDINE-1 (2H)-CARBOXYLATE (INTERMEDIATE)

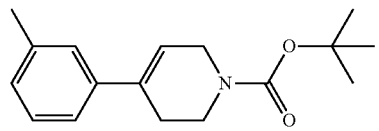

4-m-Tolyl-3,6-dihydro-2H-pyridine-1-carboxylic acid tert-butyl ester was prepared using 3-methylphenylboronic acid (400 mg, 1 mmol) and 4-trifluoromethane sulfonyloxy-3,6-dihydro-2H-pyridine-1-carboxylic acid tert-butyl ester (1 g, 1.1 mmol) as a gummy yellow solid (606 mg, 74%) following the Procedure B-Step 1. LC/MS: (Method A) 274.2 (M+H).

EXAMPLE 3E: PREPARATION OF 4-O-TOLYL-3,6-DIHYDRO-2H-PYRIDINE-1-CARBOXYLIC ACID TERT-BUTYL ESTER (INTERMEDIATE)

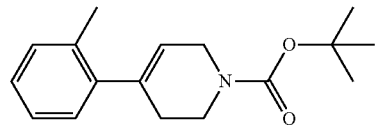

4-o-Tolyl-3,6-dihydro-2H-pyridine-1-carboxylic acid tert-butyl ester was prepared using 2-methylphenylboronic acid (300 mg, 1 mmol) and 4-trifluoro methanesulfonyloxy-3,6-dihydro-2H-pyridine-1-carboxylic acid tert-butyl ester (800 mg, 1.1 mmol) as a pale yellow liquid (363 mg, 60%) following Procedure B Step 1. LC/MS: (Method A) 274.2 (M+H).

EXAMPLE 3F: PREPARATION OF 4-(4-METHOXY-PHENYL)-3,6-DIHYDRO-2H-PYRIDINE-1-CARBOXYLIC ACID TERT-BUTYL ESTER (INTERMEDIATE)

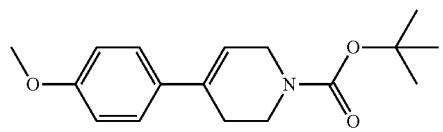

(4-(4-Methoxy-phenyl)-3,6-dihydro-2H-pyridine-1-carboxylic acid tert-butyl ester was prepared using 4-methoxyphenylboronic acid (400 mg, 1 mmol) and 4-trifluoromethanesulfonyloxy-3,6-dihydro-2H-pyridine-1-carboxylic acid tert-butyl ester (871 mg, 1.1 mmol) as a colorless liquid (410 mg, 54%) following Procedure B Step 1. LC/MS: (Method A) 290.2 (M+H).

EXAMPLE 3G: PREPARATION OF 4-(3-METHOXY-PHENYL)-3,6-DIHYDRO-2H-PYRIDINE-1-CARBOXYLIC ACID TERT-BUTYL ESTER (INTERMEDIATE)

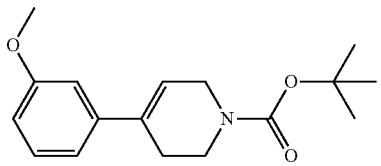 [SMILES: COc1cccc(C2=CCN(C(=O)OC(C)(C)C)CC2)c1]

(4-(3-Methoxy-phenyl)-3,6-dihydro-2H-pyridine-1-carboxylic acid tert-butyl ester was prepared using 3-methoxyphenylboronic acid (400 mg, 1 mmol) and 4-trifluoromethanesulfonyloxy-3,6-dihydro-2H-pyridine-1-carboxylic acid tert-butyl ester (871 mg, 1.1 mmol) as a yellow liquid (319 mg, 42%) following Procedure B Step 1. LC/MS: (Method A) 290.2 (M+H).

EXAMPLE 3H: PREPARATION OF 4-(2-METHOXY-PHENYL)-3,6-DIHYDRO-2H-PYRIDINE-1-CARBOXYLIC ACID TERT-BUTYL ESTER (INTERMEDIATE)

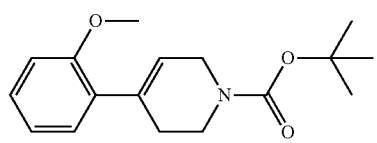 [SMILES: COc1ccccc1C1=CCN(C(=O)OC(C)(C)C)CC1]

(4-(2-Methoxy-phenyl)-3,6-dihydro-2H-pyridine-1-carboxylic acid tert-butyl ester was prepared using 2-methoxyphenylboronic acid (400 mg, 1 mmol) and 4-trifluoromethanesulfonyloxy-3,6-dihydro-2H-pyridine-1-carboxylic acid tert-butyl ester (871 mg, 1.1 mmol) as a pale yellow liquid (547 mg, 72%) following Procedure B Step 1. LC/MS: (Method A) 290.2 (M+H).

EXAMPLE 3I: PREPARATION OF 4-(2-CYANO-PHENYL)-3,6-DIHYDRO-2H-PYRIDINE-1-CARBOXYLIC ACID TERT-BUTYL ESTER (INTERMEDIATE)

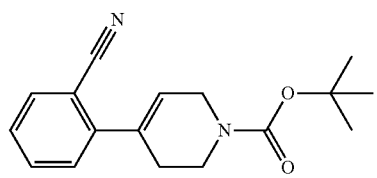 [SMILES: CC(C)(C)OC(=O)N1CC=C(c2ccccc2C#N)CC1]

(4-(2-cyano-phenyl)-3,6-dihydro-2H-pyridine-1-carboxylic acid tert-butyl ester was prepared using 2-cyanophenylboronic acid (400 mg, 1 mmol) and 4-trifluoromethanesulfonyloxy-3,6-dihydro-2H-pyridine-1-carboxylic acid tert-butyl ester (990 mg, 1.1 mmol) as a white solid (448 mg, 58%) following Procedure B Step 1. LC/MS: (Method A) 285.2 (M+H).

EXAMPLE 3J: PREPARATION OF 4-(4-CYANO-PHENYL)-3,6-DIHYDRO-2H-PYRIDINE-1-CARBOXYLIC ACID TERT-BUTYL ESTER (INTERMEDIATE)

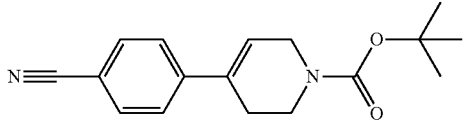

(4-(4-Cyano-phenyl)-3,6-dihydro-2H-pyridine-1-carboxylic acid tert-butyl ester was prepared using 4-cyanophenylboronic acid (400 mg, 1 mmol) and 4-trifluoromethanesulfonyloxy-3,6-dihydro-2H-pyridine-1-carboxylic acid tert-butyl ester (990 mg, 1.1 mmol) as a colorless liquid (770 mg, 62%) following Procedure B Step 1. LC/MS: (Method A) 285.1 (M+H).

EXAMPLE 3K: PREPARATION OF 4-(2-ETHOXYCARBONYL-PHENYL)-3,6-DIHYDRO-2H-PYRIDINE-1-CARBOXYLIC ACID TERT-BUTYL ESTER (INTERMEDIATE)

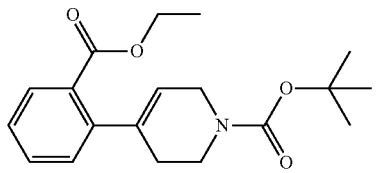 [SMILES: CCOC(=O)c1ccccc1C1=CCN(C(=O)OC(C)(C)C)CC1]

4-(2-Ethoxycarbonyl-phenyl)-3,6-dihydro-2H-pyridine-1-carboxylic acid tert-butyl ester was prepared using 2-ethoxycarbonyl-phenylboronic acid (300 mg, 1 mmol) and 4-trifluoromethanesulfonyloxy-3,6-dihydro-2H-pyridine-1-carboxylic acid tert-butyl ester (682 mg, 1.1 mmol) as a pale colorless liquid (328 mg, 64%) following Procedure B Step 1. LC/MS: (Method A) 332.1 (M+H).

EXAMPLE 3L: PREPARATION OF 4-(4-ETHOXYCARBONYL-PHENYL)-3,6-DIHYDRO-2H-PYRIDINE-1-CARBOXYLIC ACID TERT-BUTYL ESTER (INTERMEDIATE)

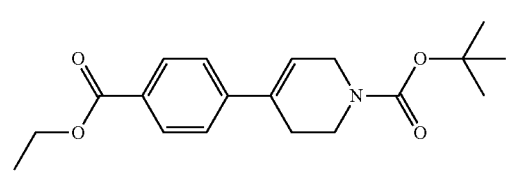 [SMILES: CCOC(=O)c1ccc(C2=CCN(C(=O)OC(C)(C)C)CC2)cc1]

4-(4-Ethoxycarbonyl-phenyl)-3,6-dihydro-2H-pyridine-1-carboxylic acid tert-butyl ester was prepared using 4-ethoxycarbonyl-phenylboronic acid (400 mg, 1 mmol) and 4-trifluoromethanesulfonyloxy-3,6-dihydro-2H-pyridine-1-carboxylic acid tert-butyl ester (682 mg, 1.1 mmol) as a colorless liquid (465 mg, 68%) following Procedure B Step 1. LC/MS: (Method A) 332.1 (M+H).

EXAMPLE 3M: PREPARATION OF 4-(2-HYDROXY-PHENYL)-3,6-DIHYDRO-2H-PYRIDINE-1-CARBOXYLIC ACID TERT-BUTYL ESTER (INTERMEDIATE)

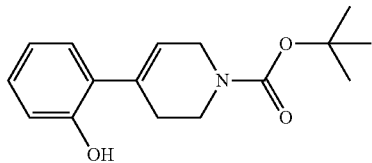 [SMILES: CC(C)(C)OC(=O)N1CC=C(c2ccccc2O)CC1]

(4-(2-hydroxy-phenyl)-3,6-dihydro-2H-pyridine-1-carboxylic acid tert-butyl ester was prepared using 2-hydroxyphenylboronic acid (300 mg, 1 mmol) and 4-trifluoromethanesulfonyloxy-3,6-dihydro-2H-pyridine-1-carboxylic acid tert-butyl ester (798 mg, 1.1 mmol) as a colorless liquid (420 mg, 72%) following Procedure B Step 1. LC/MS: (Method A) 276.2 (M+H).

EXAMPLE 3N: PREPARATION OF 4-(4-HYDROXY-PHENYL)-3,6-DIHYDRO-2H-PYRIDINE-1-CARBOXYLIC ACID TERT-BUTYL ESTER (INTERMEDIATE)

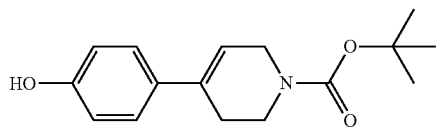

4-(4-Hydroxy-phenyl)-3,6-dihydro-2H-pyridine-1-carboxylic acid tert-butyl ester was prepared using 4-hydroxyphenylboronic acid (300 mg, 1 mmol) and 4-trifluoromethanesulfonyloxy-3,6-dihydro-2H-pyridine-1-carboxylic acid tert-butyl ester (800 mg, 1.1 mmol) as a colorless liquid (380 mg, 65%) following Procedure B Step 1. LC/MS: (Method A) 276.2 (M+H).

EXAMPLE 3O: PREPARATION OF 4-(3-HYDROXY-PHENYL)-3,6-DIHYDRO-2H-PYRIDINE-1-CARBOXYLIC ACID TERT-BUTYL ESTER (INTERMEDIATE)

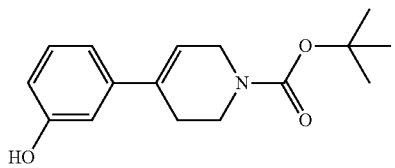 [SMILES: CC(C)(C)OC(=O)N1CC=C(c2cccc(O)c2)CC1]

4-(3-Hydroxy-phenyl)-3,6-dihydro-2H-pyridine-1-carboxylic acid tert-butyl ester was prepared using 3-hydroxyphenylboronic acid (300 mg, 1 mmol) and 4-trifluoromethanesulfonyloxy-3,6-dihydro-2H-pyridine-1-carboxylic acid tert-butyl ester (790 mg, 1.1 mmol) as a colorless liquid (420 mg, 72%) following Procedure B Step 1. LC/MS: (Method A) 276.2 (M+H).

EXAMPLE 3-14: PREPARATION OF N-(5-((4-(P-TOLYL)PIPERIDIN-1-YL)METHYL)THIAZOL-2-YL)ACETAMIDE

Following Procedure B, N-(5-((4-(p-tolyl)piperidin-1-yl)methyl)thiazol-2-yl)acetamide was synthesized from 4-p-tolyl-3,6-dihydro-2H-pyridine-1-carboxylic acid tert-butyl ester and N-(5-formyl-thiazol-2-yl)-acetamide as a white solid. Yield: 26% (34 mg). LC/MS: (Method A) 330.2 (M+H). HPLC: (Method A) RT.: 3.20 min, 98.7%, (Max), 96.6% (254 nm).
$^1$H NMR (400 MHz, DMSO-$d_6$): δ 11.94 (s, 1H), 7.25 (s, 1H), 7.11-7.05 (m, 4H), 3.63 (s, 2H), 2.92 (d, J=12.0 Hz, 2H), 2.49-2.48 (m, 1H), 2.23 (s, 3H), 2.05 (s, 3H), 2.02-1.97 (m, 2H), 1.67-1.58 (m, 4H).

EXAMPLE 3-16: PREPARATION OF N-(5-((4-(4-METHOXYPHENYL)PIPERIDIN-1-YL)METHYL)THIAZOL-2-YL)ACETAMIDE

Following Procedure B, N-(5-((4-(4-methoxyphenyl)piperidin-1-yl)methyl)thiazol-2-yl)acetamide was synthesized from 4-(4-methoxy-phenyl)-3,6-dihydro-2H-pyridine-1-carboxylic acid tert-butyl ester and N-(5-formyl-thiazol-2-yl)-acetamide. Purification by preparative HPLC afforded the trifluoroacetate salt of the title compound as a white sold. Yield: 25% (67 mg). LC/MS: (Method A) 346.2 (M+H). HPLC: (Method A) RT.: 2.83 min, 97.1%, (Max), 95.7% (254 nm).
$^1$H NMR (400 MHz, DMSO-$d_6$): δ 12.32 (s, 1H), 9.51 (s, 1H), 7.65-7.60 (m, 1H), 7.13-7.10 (m, 2H), 6.91-6.86 (m, 2H), 4.56 (d, J=4.0 Hz, 2H), 3.73 (s, 3H), 3.53-3.52 (m, 2H), 3.03-2.97 (m, 2H), 2.75-2.72 (m, 1H), 2.15 (s, 3H), 1.99-1.95 (m, 2H), 1.78-1.72 (m, 2H).

EXAMPLE 3-30: PREPARATION OF N-(5-((4-(2-FLUOROPHENYL)PIPERIDIN-1-YL)METHYL)THIAZOL-2-YL)ACETAMIDE

Following Procedure B, N-(5-((4-(2-fluorophenyl)piperidin-1-yl)methyl)thiazol-2-yl)acetamide was synthesized from tert-butyl 4-(2-fluorophenyl)-5,6-dihydropyridine-1(2H)-carboxylate and N-(5-formyl-thiazol-2-yl)-acetamide as a pale yellow solid. Yield: 5% (3 mg). LC/MS: (Method A) 334.2 (M+H). HPLC: (Method A) RT.: 2.80 min, 97.4%, (Max), 97.4% (254 nm).
$^1$H NMR (400 MHz, DMSO-$d_6$): δ 11.95 (s, 1H), 7.36-7.32 (m, 1H), 7.26-7.20 (m, 2H), 7.15-7.09 (m, 2H), 3.64 (s, 2H), 2.96-2.88 (m, 2H), 2.77-2.72 (m, 1H), 2.09-1.98 (m, 5H), 1.84-1.75 (m, 4H).

EXAMPLE 3-31: PREPARATION OF N-(5-((4-(M-TOLYL)PIPERIDIN-1-YL)METHYL)THIAZOL-2-YL)ACETAMIDE

Following Procedure B, N-(5-((4-(m-tolyl)piperidin-1-yl)methyl)thiazol-2-yl)acetamide was synthesized from tert-butyl 4-(m-tolyl)-5,6-dihydropyridine-1 (2H)-carboxylate and N-(5-formyl-thiazol-2-yl)-acetamide as a white solid. Yield: 17% (32 mg). LC/MS: (Method A) 330.2 (M+H). HPLC: (Method A) RT.: 3.07 min, 98.7%, (Max), 98.9% (254 nm).
$^1$H NMR (400 MHz, DMSO-$d_6$): δ 11.95 (s, 1H), 7.25 (s, 1H), 7.13 (d, J=8.0 Hz, 1H), 7.04-6.98 (m, 3H), 3.63 (s, 2H), 2.94-2.91 (m, 2H), 2.49-2.48 (m, 1H), 2.2 (s, 3H), 2.10 (s, 3H), 2.02-2.01 (m, 2H), 1.78-1.64 (m, 4H).

EXAMPLE 3-32: PREPARATION OF N-(5-((4-(3-METHOXYPHENYL)PIPERIDIN-1-YL)METHYL)THIAZOL-2-YL)ACETAMIDE

Following Procedure B, N-(5-((4-(3-methoxyphenyl)piperidin-1-yl)methyl)thiazol-2-yl)acetamide was synthesized from 4-(3-methoxy-phenyl)-3,6-dihydro-2H-pyridine-1-carboxylic acid tert-butyl ester and N-(5-formyl-thiazol-2-yl)-acetamide as a white solid. Yield: 14% (29 mg). LC/MS: (Method A) 346.2 (M+H). HPLC: (Method A) RT.: 2.73 min, 98.9%, (Max), 98.6% (254 nm).

$^1$H NMR (400 MHz, DMSO-$d_6$): δ 11.95 (s, 1H), 7.25-7.15 (m, 2H), 6.81-6.71 (m, 2H), 3.71 (s, 3H), 3.63 (s, 2H), 2.94-2.91 (m, 2H), 2.49-2.43 (m, 1H), 2.10 (s, 3H), 2.05-1.97 (m, 2H), 1.72-1.65 (m, 4H).

EXAMPLE 3-33: PREPARATION OF N-(5-((4-(2-METHOXYPHENYL)PIPERIDIN-1-YL)METHYL)THIAZOL-2-YL)ACETAMIDE

Following Procedure B, N-(5-((4-(2-methoxyphenyl)piperidin-1-yl)methyl)thiazol-2-yl)acetamide was synthesized from 4-(2-methoxy-phenyl)-3,6-dihydro-2H-pyridine-1-carboxylic acid tert-butyl ester and N-(5-formyl-thiazol-2-yl)-acetamide as an off-white solid. Yield: 30% (62 mg). LC/MS: (Method A) 346.0 (M+H). HPLC: (Method A) RT.: 2.89 min, 97.9%, (Max), 97.6% (254 nm).

$^1$H NMR (400 MHz, DMSO-$d_6$): δ 11.95 (s, 1H), 7.25 (s, 1H), 7.18-7.12 (m, 2H), 6.93-6.85 (m, 2H), 3.75 (s, 3H), 3.63 (s, 2H), 2.93-2.80 (m, 3H), 2.05 (s, 3H), 2.03-1.97 (m, 2H), 1.67-1.54 (m, 4H).

EXAMPLE 3-35: PREPARATION OF N-(5-((4-(2-CYANOPHENYL)PIPERIDIN-1-YL)METHYL)THIAZOL-2-YL)ACETAMIDE

Following Procedure B, N-(5-((4-(2-cyanophenyl)piperidin-1-yl)methyl)thiazol-2-yl)acetamide was synthesized from 4-(2-cyano-phenyl)-3,6-dihydro-2H-pyridine-1-carboxylic acid tert-butyl ester and N-(5-formyl-thiazol-2-yl)-acetamide as a pale yellow solid. Yield: 29% (54 mg). LC/MS: (Method A) 341.2 (M+H). HPLC: (Method A) RT.: 2.45 min, 93.8%, (Max), 95.3% (254 nm).

$^1$H NMR (400 MHz, DMSO-$d_6$): δ 11.97 (s, 1H), 7.76 (d, J=8.0 Hz, 1H), 7.67-7.63 (m, 1H), 7.55 (d, J=8.0 Hz, 1H), 7.41 (d, J=4.0 Hz, 1H), 7.27-7.26 (m, 1H), 3.68 (s, 2H), 2.99-2.97 (m, 2H), 2.81 (s, 1H), 2.10-2.08 (m, 5H), 1.74-1.72 (m, 4H).

EXAMPLE 3-36: PREPARATION OF N-(5-((4-(4-CYANOPHENYL)PIPERIDIN-1-YL)METHYL)THIAZOL-2-YL)ACETAMIDE

Following Procedure B, N-(5-((4-(4-cyanophenyl)piperidin-1-yl)methyl)thiazol-2-yl)acetamide was synthesized from 4-(4-cyano-phenyl)-3,6-dihydro-2H-pyridine-1-carboxylic acid tert-butyl ester and N-(5-formyl-thiazol-2-yl)-acetamide as an off-white solid. Yield: 2% (3 mg). LC/MS: (Method A) 341.2 (M+H). HPLC: (Method A) RT.: 2.59 min, 94.6%, (Max), 89.0% (254 nm).

$^1$H NMR (400 MHz, DMSO-$d_6$): δ 11.95 (s, 1H), 7.73 (d, J=8.0 Hz, 2H), 7.46 (d, J=8.0 Hz, 2H), 7.26 (s, 1H), 3.65 (s, 2H), 2.95-2.88 (m, 2H), 2.58 (s, 1H), 2.10-2.02 (m, 5H), 1.74-1.62 (m, 4H).

EXAMPLE 3-37: PREPARATION OF N-(5-((4-(2-HYDROXYPHENYL)PIPERIDIN-1-YL)METHYL)THIAZOL-2-YL)ACETAMIDE

Following Procedure B, N-(5-((4-(2-hydroxyphenyl)piperidin-1-yl)methyl)thiazol-2-yl)acetamide was synthesized from 4-(2-hydroxy-phenyl)-3,6-dihydro-2H-pyridine-1-carboxylic acid tert-butyl ester and N-(5-formyl-thiazol-2-yl)-acetamide. Purification by preparative HPLC afforded the trifluoroacetate salt of the title compound as an off-white solid. Yield: 7% (19 mg). LC/MS: (Method A) 332.2 (M+H). HPLC: (Method A) RT.: 2.28 min, 98.9%, (Max), 98.6% (254 nm).

$^1$H NMR (400 MHz, DMSO-$d_6$): δ 12.29 (s, 1H), 9.56-9.51 (m, 1H), 7.59 (s, 1H), 7.05-7.01 (m, 2H), 6.82-6.74 (m, 2H), 4.54 (m, 2H), 3.49-3.47 (m, 2H), 3.09-3.00 (m, 3H), 2.15 (s, 3H), 1.96-1.85 (m, 4H).

EXAMPLE 3-38: PREPARATION OF N-(5-((4-(4-HYDROXYPHENYL)PIPERIDIN-1-YL)METHYL)THIAZOL-2-YL)ACETAMIDE

Following Procedure B, N-(5-((4-(4-hydroxyphenyl)piperidin-1-yl)methyl)thiazol-2-yl)acetamide was synthesized from 4-(4-hydroxy-phenyl)-3,6-dihydro-2H-pyridine-1-carboxylic acid tert-butyl ester and N-(5-formyl-thiazol-2-yl)-acetamide as a white solid. Yield: 6% (5 mg). LC/MS: (Method A) 332.2 (M+H). HPLC: (Method A) RT.: 1.90 min, 96.5%, (Max), 97.9% (254 nm).

$^1$H NMR (400 MHz, DMSO-$d_6$): δ 11.95 (s, 1H), 9.14 (s, 1H), 7.24 (s, 1H), 7.01 (d, J=8.2 Hz, 2H), 6.65 (d, J=8.2 Hz, 2H), 3.62 (s, 2H), 2.92-2.89 (m, 2H), 2.32-2.31 (m, 1H), 2.10 (s, 3H), 2.03-1.98 (m, 2H), 1.68-1.53 (m, 4H).

EXAMPLE 3-39: PREPARATION OF N-(5-((4-(3-HYDROXYPHENYL)PIPERIDIN-1-YL)METHYL)THIAZOL-2-YL)ACETAMIDE

Following Procedure B, N-(5-((4-(3-hydroxyphenyl)piperidin-1-yl)methyl)thiazol-2-yl)acetamide was synthesized from 4-(3-hydroxy-phenyl)-3,6-dihydro-2H-pyridine-1-carboxylic acid tert-butyl ester and N-(5-formyl-thiazol-2-yl)-acetamide. Purification by preparative HPLC afforded the trifluoroacetate salt of N-(5-((4-(3-hydroxyphenyl)piperidin-1-yl)methyl)thiazol-2-yl)acetamide as a white solid. Yield: 9% (24 mg). LC/MS: (Method A) 332.2 (M+H). HPLC: (Method A) RT.: 2.11 min, 98.9%, (Max), 98.8% (254 nm).

$^1$H NMR (400 MHz, DMSO-$d_6$): δ 12.32 (s, 1H), 9.55-9.37 (m, 1H), 7.60 (s, 1H), 7.12-7.08 (m, 1H), 6.62-6.58 (m, 3H), 4.55 (d, J=4.2 Hz, 2H), 3.50-3.47 (m, 2H), 3.03-2.97 (m, 2H), 2.72-2.66 (m, 1H), 2.16 (s, 3H), 1.98-1.82 (m, 2H), 1.79-1.74 (m, 2H).

EXAMPLE 3-42: PREPARATION OF N-(5-((4-(4-FLUOROPHENYL)PIPERIDIN-1-YL)METHYL)THIAZOL-2-YL)ACETAMIDE

Following Procedure B, N-(5-((4-(4-fluorophenyl)piperidin-1-yl)methyl)thiazol-2-yl)acetamide was synthesized from 4-(4-fluoro-phenyl)-3,6-dihydro-2H-pyridine-1-carboxylic acid tert-butyl ester and N-(5-formyl-thiazol-2-yl)-acetamide as a pale brown solid. Yield: 35% (41 mg). LC/MS: (Method A) 334.0 (M+H). HPLC: (Method A) RT.: 2.98 min, 98.2%, (Max), 96.6% (254 nm).

$^1$H NMR (400 MHz, DMSO-d$_6$): δ 11.95 (s, 1H), 7.29-7.26 (m, 3H), 7.10-7.06 (m, 2H), 3.64 (s, 2H), 2.94-2.91 (m, 2H), 2.49-2.48 (m, 1H), 2.10 (s, 3H), 2.05-2.00 (m, 2H), 1.72-1.63 (m, 4H).

EXAMPLE 3-43: PREPARATION OF N-(5-((4-(O-TOLYL)PIPERIDIN-1-YL)METHYL)THIAZOL-2-YL)ACETAMIDE

Following Procedure B, N-(5-((4-(o-tolyl)piperidin-1-yl)methyl)thiazol-2-yl)acetamide was synthesized from 4-o-tolyl-3,6-dihydro-2H-pyridine-1-carboxylic acid tert-butyl ester and N-(5-formyl-thiazol-2-yl)-acetamide. Purification by preparative HPLC afforded the trifluoroacetate salt of the title compound as a white sold. Yield: 40% (76 mg). LC/MS: (Method A) 330.2 (M+H). HPLC: (Method A) RT.: 3.01 min, 99.4%, (Max), 98.8% (254 nm).

$^1$H NMR (400 MHz, DMSO-d$_6$): δ 11.96 (s, 1H), 8.18 (s, 1H), 7.26-7.03 (m, 5H), 3.66 (s, 2H), 2.96-2.93 (m, 2H), 2.67-2.61 (m, 1H), 2.26 (s, 3H), 2.11-2.06 (m, 5H), 1.65-1.62 (m, 4H).

EXAMPLE 3-44: PREPARATION OF 2-(1-((2-ACETAMIDOTHIAZOL-5-YL)METHYL)PIPERIDIN-4-YL)BENZOIC ACID

Following Procedure B, ethyl 2-(1-((2-acetamidothiazol-5-yl)methyl)piperidin-4-yl)benzoate was synthesized from N-(5-formyl-thiazol-2-yl)-acetamide and 4-(2-ethoxycarbonyl-phenyl)-3,6-dihydro-2H-pyridine-1-carboxylic acid tert-butyl ester. To a stirred solution of ethyl 2-(1-((2-acetamidothiazol-5-yl)methyl)piperidin-4-yl)benzoate (1 eq.) in THF/MeOH/H$_2$O (1:1:1) (3 mL) was added LiOH.H$_2$O (1 eq.). The reaction mixture was stirred at RT for 3 h. After the completion of the reaction, the reaction mixture was neutralized with citric acid and then extracted with DCM. The organic layer was dried over Na$_2$SO$_4$, filtered and concentrated under reduced pressure. The crude product was purified by preparative HPLC to afford the hydrochloride salt of 2-(1-((2-acetamidothiazol-5-yl)methyl)piperidin-4-yl)benzoic acid as a pale brown solid. Yield: 10% (9 mg). LC/MS: (Method A) 360.2 (M+H). HPLC: (Method A) RT.: 2.35 min, 99.0%, (Max), 98.6% (254 nm).

$^1$H NMR (400 MHz, DMSO-d$_6$): δ 13.05 (s, 1H), 12.32 (s, 1H), 9.63 (s, 1H), 7.76-7.70 (m, 1H), 7.60-7.53 (m, 1H), 7.35-7.31 (m, 3H), 4.56 (s, 2H), 3.60-3.49 (m, 3H), 3.11-3.05 (m, 2H), 2.15 (s, 3H), 2.00-1.86 (m, 4H).

EXAMPLE 3-45: PREPARATION OF 4-(1-((2-ACETAMIDOTHIAZOL-5-YL)METHYL)PIPERIDIN-4-YL)BENZOIC ACID

Following Procedure B, ethyl 4-(1-((2-acetamidothiazol-5-yl)methyl)piperidin-4-yl)benzoate was synthesized from 4-(4-ethoxycarbonyl-phenyl)-3,6-dihydro-2H-pyridine-1-carboxylic acid tert-butyl ester and N-(5-formyl-thiazol-2-yl)-acetamide. To a stirred solution of ethyl 4-(1-((2-acetamidothiazol-5-yl)methyl)piperidin-4-yl)benzoate (1 eq./) in THF/MeOH/H$_2$O (1:1:1) (3 mL), LiOH.H$_2$O (1 eq.) was added and the reaction mixture was allowed to stir at RT for 3 h. After the completion of the reaction, the reaction mixture was neutralized with citric acid and extracted with DCM. The organic layer was dried over Na$_2$SO$_4$, filtered, and concentrated under reduced pressure. The crude product was purified by preparative HPLC to afford the hydrochloride salt of 4-(1-((2-acetamidothiazol-5-yl)methyl)piperidin-4-yl)benzoic acid as a brown solid. Yield: 26% (37 mg). LC/MS: (Method A) 360.2 (M+H). HPLC: (Method A) RT.: 1.96 min, 99.0%, (Max), 97.8% (254 nm).

$^1$H NMR (400 MHz, DMSO-d$_6$): δ 12.89 (s, 1H), 12.31 (s, 1H), 10.54 (s, 1H), 7.90 (d, J=8.2 Hz, 2H), 7.65 (s, 1H), 7.34 (d, J=8.3 Hz, 2H), 4.53 (s, 1H), 3.49-3.47 (m, 2H), 3.01-2.88 (m, 3H), 2.88 (s, 3H), 1.99-1.96 (m, 4H).

EXAMPLE 4-12: PREPARATION OF N-CYCLOPROPYL-5-((4-PHENYLPIPERIDIN-1-YL)METHYL)THIAZOL-2-AMINE

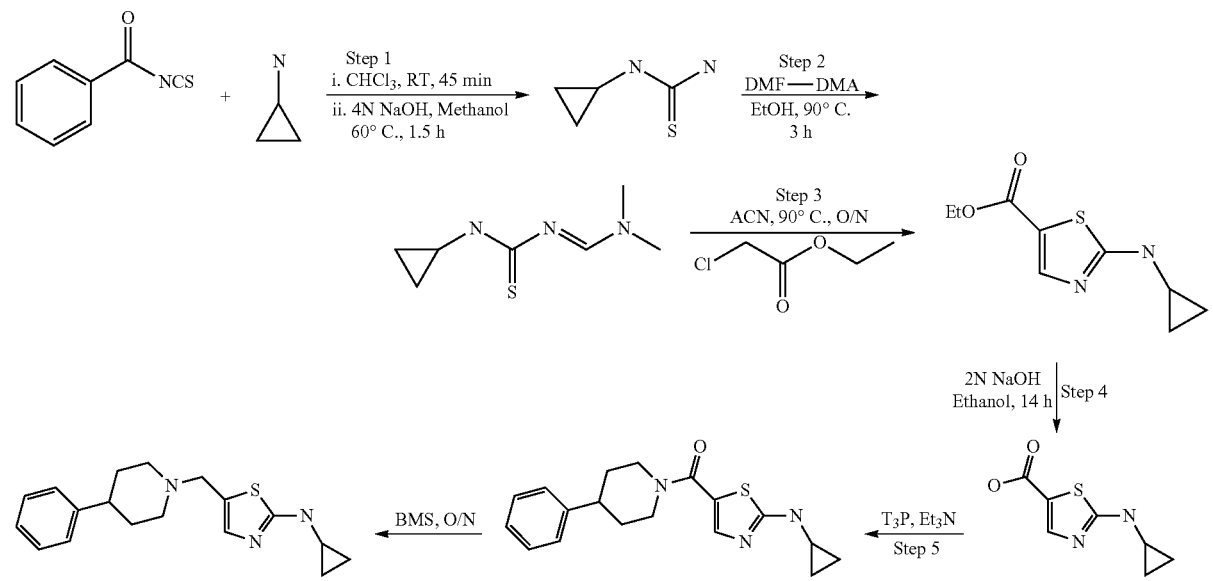

Step 1: To an ice-cold, stirred solution of benzoyl isothiocyanate (1 eq., 17.5 mmol) in dry chloroform (20 mL), was added cyclopropylamine (1 eq., 17.5 mmol). The reaction mixture was allowed to stir at RT for 45 min. After completion of the reaction, the reaction mixture was concentrated under reduced pressure. The residue, crude 1-benzoyl-3-cyclopropyl-thiourea, was used in the next reaction without purification. To an ice-cold, stirred solution of 1-benzoyl-3-cyclopropyl-thiourea (1 eq., 17.2 mmol) in methanol (35 mL) was added NaOH (4N, 1 eq.). The reaction mixture was allowed to stir at 60° C. for 1.5 h. After completion of the reaction, the reaction mixture was concentrated under reduced pressure, and ice cold water was added. The solid was collected by filtration to afford 1-cyclopropylthiourea as a white solid, which was used in the next step without further purification. Yield: 74% (1.16 g).

$^1$H NMR: (400 MHz, CD$_3$OD): δ 2.47 (bs, 1H), 0.81-0.76 (m, 2H), 0.60-0.58 (m, 2H).

Step 2: To a stirred solution of 1-cyclopropylthiourea (1 eq, 9.2 mmol) in ethanol (25 mL), was added DMF-DMA (1.5 eq, 14.9 mmol). The reaction mixture was then heated to 90° C. with stirring for 3 h. After completion of the reaction, the reaction mixture was concentrated under reduced pressure, and the residue obtained was triturated with ethyl acetate to afford 1-cyclopropyl-3-[1-dimethyl-amino-methylidene]-thiourea as a white solid, which was used in the next step without further purification. Yield: 78% (1.61 g).

$^1$H NMR (400 MHz, DMSO-d$_6$): δ 8.6 (s, 1H), 3.21-3.16 (m, 1H), 3.1 (s, 3H), 3.0 (s, 3H), 0.68-0.63 (m, 2H), 0.58-0.56 (m, 2H).

Step 3: To a stirred solution of 1-cyclopropyl-3-[1-dimethylamino-methylidene]-thiourea (1 eq.) in CH$_3$CN (15 mL), was added ethyl chloroacetate (1.1 eq). The reaction mixture as allowed to stir at 90° C. for 14 h. After completion of the reaction, the reaction mixture was concentrated under reduced pressure. The residue was triturated with saturated, aqueous NaHCO$_3$. The solid was collected by filtration to afford 2-cyclopropylamino-thiazole-5-carboxylic acid ethyl ester as a brown solid, which was used in the next step without further purification. Yield: 55% (0.85 g). LC/MS: (Method A) 213.0 (M+H).

Step 4: To a stirred solution of 2-cyclopropylamino-thiazole-5-carboxylic acid ethyl ester (1 g, 1 eq.) in ethanol (15 mL) at 0° C. was added NaOH (2N, 1.1 eq.). The reaction mixture was then allowed to stir at RT for 14 h. After completion of the reaction, the reaction mixture was concentrated under reduced pressure and neutralized by the addition of aqueous HCl (1 N). The solid was collected by filtration to afford 2-(cyclopropylamino)thiazole-5-carboxylic acid as a white solid that was used in the next step without purification. Yield: 98% (0.85 g). LC/MS: (Method B) 183.0 (M–H).

Step 5: To a stirred solution of 2-(cyclopropylamino) thiazole-5-carboxylic acid (800 mg, 1 eq.) in DCM (15 mL) at 0° C. was added Et$_3$N (870 mg, 1.1 eq.), 4-phenylpiperidine (760 mg, 1.1 eq.) and T$_3$P (2.76 g, 2 eq.). The reaction mixture was allowed to stir at RT for 4 h. After completion of the reaction, the reaction mixture was concentrated under reduced pressure. The residue was subjected to flash chromatography to afford (2-(cyclopropylamino)thiazol-5-yl)(4-phenylpiperidin-1-yl)methanone as a white solid. Yield: 45% (0.64 g). LC/MS: (Method A) 328.0 (M–H).

Step 6: To a stirred solution of (2-(cyclopropylamino) thiazol-5-yl)(4-phenylpiperidin-1-yl)methanone (100 mg, 1 eq.) in THF (15 mL) at 0° C. was added borane-methyl sulfide complex in THF (2 M, 0.75 mL, 2 eq.). The reaction mixture was allowed to stir at 60° C. for 4 h, treated with methanol (5 mL), and then heated with stirring to 60° C. for another 1 h. After the completion of the reaction, the reaction mixture was concentrated under reduced pressure. The residue was subjected to flash chromatography to afford N-cyclopropyl-5-((4-phenylpiperidin-1-yl)methyl)thiazol-2-amine as an off-white solid. Yield: 28% (34.4 mg). LC/MS: (Method B) 314.3 (M+H). HPLC: (Method A) RT.: 2.49 min, 98.1%, (Max), 98.6% (254 nm).

$^1$H NMR (400 MHz, DMSO-d$_6$): δ 7.30-7.16 (m, 5H), 6.87-7.05 (m, 1H), 3.70-3.68 (m, 2H), 3.11-3.09 (m, 4H), 2.30-2.25 (m, 2H), 1.84-1.80 (m, 2H), 1.68-1.64 (m, 2H), 0.71-0.65 (m, 2H), 0.50-0.46 (m, 2H).

EXAMPLE 5A: PREPARATION OF N-METHYL-5-((4-PHENYLPIPERIDIN-1-YL)METHYL)THI-AZOL-2-AMINE (INTERMEDIATE)

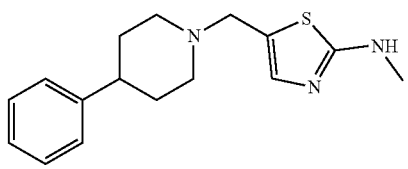 [SMILES: CNc1ncc(CN2CCC(c3ccccc3)CC2)s1]

Subsequent to Example 1, step 3, to a stirred solution of tert-butyl (5-((4-phenylpiperidin-1-yl)methyl)thiazol-2-yl) carbamate (200 mg, 1 eq.) in THF (10 mL) at 0° C. was added LiAlH$_4$ (2.0 M solution in THF, 0.8 mL, 1.5 eq). The reaction mixture was then heated to 65° C. for 90 min. After completion of the reaction, the reaction mixture was concentrated under reduced pressure, water was added, and the product extracted with DCM. The organic phase was separated, dried over sodium sulfate, filtered and concentrated under reduced pressure. The residue was subjected to flash chromatography to afford methyl-5-((4-phenylpiperidin-1-yl)methyl)thiazol-2-amine as an off-white solid. Yield: 80% (120 mg). LC/MS: (Method B) 288.3 (M+H). HPLC: (Method A) RT.: 2.23 min, 99.9%, (Max), 99.6% (254 nm).

$^1$H NMR (400 MHz, DMSO-d$_6$): δ 7.31-7.21 (m, 4H), 7.18-7.14 (m, 1H), 6.8 (s, 1H), 3.5 (s, 2H), 2.9 (d, J=8.0 Hz, 2H), 2.76-2.75 (m, 3H), 2.45-2.42 (m, 1H), 2.02-1.96 (m, 2H), 1.73-1.70 (m, 2H), 1.64-1.57 (m, 2H).

EXAMPLE 5B: PREPARATION OF N-ETHYL-5-((4-PHENYLPIPERIDIN-1-YL)METHYL)OX-AZOL-2-AMINE (INTERMEDIATE)

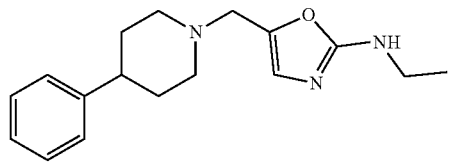 [SMILES: CCNc1ncc(CN2CCC(c3ccccc3)CC2)o1]

Step 1: To a solution of ethyl 2-aminooxazole-5-carboxylate (200 mg, 1 eq.) in dry DMF (2 mL) was added BOC-anhydride (418 mg, 1.2 eq.), DIPEA (0.6 mL, 3 eq.) and finally DMAP (78 mg, 0.5 eq.). The reaction mixture was allowed to stir at RT overnight. After completion of the reaction, the reaction mixture was concentrated under reduced pressure, and water was added. The product was extracted with DCM. The organic phase was concentrated under reduced pressure and the residue was subjected to flash chromatography to afford ethyl 2-((tert-butoxycarbonyl)amino)oxazole-5-carboxylate as an off-white solid. Yield: 79% (1.3 g). LC/MS: (Method A) 257.0 (M+H).

$^1$H NMR (400 MHz, DMSO-$d_6$): 11.3 (s, 1H), 7.8 (s, 1H), 4.29-4.27 (m, 2H), 1.5 (s, 9H), 1.3 (t, J=8.0 Hz, 3H).

Step 2: To a solution of ethyl 2-((tert-butoxycarbonyl) amino)oxazole-5-carboxylate (500 mg, 1 eq) in THF/MeOH/H$_2$O (3:1:1, 15 mL) was added LiOH (165 mg, 2 eq.) and the reaction mixture was allowed to stir at RT for 4 h. After completion of the reaction, the reaction mixture was concentrated under reduced pressure, and water was added. The mixture was neutralized by the addition of aqueous HCl (1 N). The off-white solid was collected by filtration and dried to afford 2-((tert-butoxycarbonyl)amino)oxazole-5-carboxylic acid, which was used in the next step without purification. Yield: 76% (880 mg).

$^1$H NMR (400 MHz, DMSO-$d_6$): δ 11.2 (s, 1H), 7.7 (s, 1H), 1.5 (s, 9H).

Step 3: To a solution of 2-((tert-butoxycarbonyl)amino) oxazole-5-carboxylic acid (320 mg, 1 eq.) in DCM (15 mL) at 0° C. was added Et$_3$N (0.6 mL, 3 eq.) and 4-phenylpiperidine (248 mg, 1.54 mmol, 1.1 eq.). After 15 min of cooling to 0° C., the reaction mixture was treated with T$_3$P (900 mg, 2 eq.). The reaction mixture was allowed to stir at RT for 14 h. After completion of the reaction, the reaction mixture was concentrated under reduced pressure and water was added. The product was extracted with DCM. The organic phase was dried over sodium sulfate, filtered, and concentrated under reduced pressure. The residue was subjected to flash chromatography to afford tert-butyl (5-(4-phenylpiperidine-1-carbonyl)oxazol-2-yl)carbamate as an off-white solid. Yield: 82% (430 mg). LC/MS: (Method B) 372.0 (M+H).

$^1$H NMR (400 MHz, DMSO-$d_6$): δ 11.0 (s, 1H), 7.5 (s, 1H), 7.31-7.18 (m, 5H), 4.4 (d, J=12.0 Hz, 2H), 3.01-2.83 (m, 2H), 1.84-1.81 (m, 2H), 1.60-1.58 (m, 2H), 1.4 (s, 9H).

Step 4: To a solution of tert-butyl (5-(4-phenylpiperidine-1-carbonyl)oxazol-2-yl)carbamate (400 mg, 1 eq.) in dry THF (15 mL) at 0° C. was added LAH in THF (1 M, 1.6 mL, 1.5 eq.). The reaction mixture was then allowed to stir at RT for 30 min. After completion of the reaction, the reaction mixture was quenched by the addition of aqueous NaOH (1 N) and extracted with dichloromethane. The organic phase was dried over sodium sulfate, filtered, and concentrated under reduced pressure. The residue was subjected to flash chromatography to afford tert-butyl (5-((4-phenylpiperidin-1-yl)methyl)oxazol-2-yl)carbamate as an off-white solid. Yield: 40% (150 mg). LC/MS: (Method B) 358.0 (M+H).

$^1$H NMR (400 MHz, DMSO-$d_6$): δ 10.4 (s, 1H), 7.28-7.16 (m, 5H), 6.9 (s, 1H), 3.5 (s, 2H), 2.92-2.89 (m, 2H), 2.45-2.43 (m, 1H), 2.08-2.03 (m, 2H), 1.73-1.60 (m, 4H), 1.6 (s, 9H).

Step 5: To a solution of tert-butyl (5-((4-phenylpiperidin-1-yl)methyl)oxazol-2-yl)carbamate (50 mg, 1 eq) in dry DMF (5 mL) at 0° C. was added NaH (20 mg, 1.5 eq) and ethyl iodide (0.02 mL, 1.5 eq). The reaction mixture was allowed to stir at RT for 2 h. After completion of the reaction, the reaction was quenched by the addition of ice cold water and the product was extracted with DCM. The organic phase was dried over sodium sulfate, filtered, and concentrated under reduced pressure. The residue was subjected to flash chromatography to afford tert-butyl ethyl(5-((4-phenylpiperidin-1-yl)methyl)oxazol-2-yl)carbamate as an off-white solid. Yield: 56% (30 mg). LC/MS: (Method B) 386.2 (M+H).

Step 6: To a solution tert-butyl ethyl(5-((4-phenylpiperidin-1-yl)methyl)oxazol-2-yl)carbamate (30 mg, 1 eq.) in dry 1,4-dioxane (1 mL) at 0° C. was added dioxane/HCl (1 mL). The reaction mixture was then allowed to stir at RT for 12 h. After completion of the reaction, the reaction mixture was concentrated under reduced pressure to afford the hydrochloride salt of N-ethyl-5-((4-phenylpiperidin-1-yl)methyl) oxazol-2-amine as an off-white solid. Yield: 80% (18.3 mg). LC/MS: (Method A) 286.3 (M+H). HPLC: (Method A) RT.: 5.41 min, 99.6%, (Max), 99.1% (254 nm).

$^1$H NMR (400 MHz, DMSO-$d_6$): δ 10.9 (s, 1H), 8.6 (s, 1H), 7.35-7.30 (m, 2H), 7.26-7.20 (m, 3H), 4.5 (d, J=8.0 Hz, 2H), 3.50-3.47 (m, 2H), 3.30-3.27 (m, 2H), 3.08-3.01 (m, 2H), 2.81-2.75 (m, 1H), 2.01-2.05 (m, 4H), 1.2 (t, J=4.0 Hz, 3H).

EXAMPLE 5-1: PREPARATION OF N-(5-((4-PHENYLPIPERIDIN-1-YL)METHYL)THIAZOL-2-YL)ACETAMIDE

Subsequent to Example 1, to a solution of 5-((4-phenylpiperidin-1-yl)methyl)thiazol-2-amine hydrochloride (2.2 g, 0.007 mol) in DCM (30 mL) at 0° C. was added pyridine (2.86 mL, 0.0355 mol), followed by acetyl chloride (0.8 mL, 0.0113 mol) dropwise over 5 min. The reaction mixture was stirred at RT for 1 h. The reaction progress was monitored by TLC. After completion of the reaction, the reaction mixture was concentrated under reduced pressure and neutralized with 10% NaHCO$_3$ in water. The product was extracted with ethyl acetate (200 mL). The organic phase was washed consecutively with water and brine, dried over sodium sulfate, and concentrated under reduced pressure. The residue was subjected to flash chromatography (60-120 mesh silica) using petroleum ether/ethyl acetate as eluent to afford N-(5-((4-phenylpiperidin-1-yl)methyl)thiazol-2-yl) acetamide (1.2 g, 53.8%) as a pale yellow solid. TLC (petroleum ether/ethyl acetate, 5:5, Rf=0.2). LC/MS: (Method A) 316 (M+H). HPLC: (Method A) RT.: 2.7 min, 97%.

$^1$H NMR (DMSO-$d_6$, 400 MHz) δ 11.94 (bs, 1H), 7.28-7.21 (m, 5H), 7.18-7.14 (m, 1H), 3.64 (s, 2H), 2.94-2.91 (m, 2H), 2.49-2.42 (m, 4H), 2.10-1.97 (m, 2H), 1.73-1.70 (m, 4H).

EXAMPLE 5-4: PREPARATION OF N-[5-(4-PHENYL-PIPERIDIN-1-YLMETHYL)-THIAZOL-2-YL]-ACRYLAMIDE

Subsequent to Example 1, to a stirred solution of 5-((4-phenylpiperidin-1-yl)methyl)thiazol-2-amine hydrochloride (100 mg, 1 eq.) in dichloromethane (5 mL) at −20° C., were added acrolyl chloride (29 mg, 1 eq.), and Et$_3$N (96 mg, 3 eq.). The reaction was stirred at −20° C. for 1 h. After completion of the reaction, the reaction mixture was concentrated under reduced pressure, water was added, and the product was extracted with DCM. The organic phase was dried over sodium sulfate, filtered, and concentrated under reduced pressure.

The residue was subjected to preparative HPLC to afford the trifluoroacetate salt of N-[5-(4-phenyl-piperidin-1-ylmethyl)-thiazol-2-yl]-acrylamide as an off-white solid. Yield: 14% (16 mg). LC/MS: (Method A) 328.2 (M+H). HPLC: (Method A) RT.: 2.96 min, 96.2%, (Max), 92.5% (254 nm).

$^1$H NMR (400 MHz, DMSO-$d_6$): δ 12.6 (s, 1H), 9.5 (s, 1H), 7.7 (s, 1H), 7.67-7.20 (m, 5H), 6.57-6.50 (m, 1H), 6.44-6.39 (m, 1H), 5.9 (dd, J=4.0, 8.0 Hz, 1H), 4.6 (dd, J=8.0 Hz, 2H), 3.5 (dd, J=12.0 Hz, 2H), 3.07-3.01 (m, 2H), 2.82-2.76 (m, 1H), 2.01-2.15 (m, 2H), 1.85-1.92 (m, 2H).

EXAMPLE 5-5: PREPARATION OF N-ETHYL-5-((4-PHENYLPIPERIDIN-1-YL)METHYL)THIAZOL-2-AMINE

Step 1: Subsequent to Example 1, step 3, to a stirred solution of tert-butyl (5-((4-phenylpiperidin-1-yl)methyl)thiazol-2-yl)carbamate (200 mg, 1 eq.) in DMF (5 mL) was added NaH (80 mg, 1.5 eq.). The reaction mixture was then treated with ethyliodide (0.08 mL, 1.5 eq.) and to 65° C. for 90 min. After completion of the reaction, the reaction mixture was concentrated under reduced pressure, water was added, and the product was extracted with DCM. The organic phase was separated, dried over sodium sulfate, filtered and concentrated under reduced pressure. The residue was subjected to flash chromatography to afford tert-butyl ethyl(5-((4-phenylpiperidin-1-yl)methyl)thiazol-2-yl) carbamate as an off-white solid. Yield: 45% (100 mg). LC/MS: (Method A) 402.2 (M+H).

Step 2: To a stirred solution of tert-butyl ethyl(5-((4-phenylpiperidin-1-yl)methyl)thiazol-2-yl)carbamate (50 mg) in dry dioxane (2 mL) was added HCl in dioxane (5 mL) and the reaction mixture was stirred at RT for 12 h. After the completion of reaction, the reaction mixture was concentrated under reduced pressure to afford N-ethyl-5-((4-phenylpiperidin-1-yl)methyl)thiazol-2-amine as an off-white solid. Yield: 22% (7.3 mg). LC/MS: (Method B) 302.2 (M+H). HPLC: (Method B) RT.: 5.89 min, 99.5%, (Max), 99.1% (254 nm).

$^1$H NMR (400 MHz, DMSO-d$_6$): δ 7.4 (t, J=12.0 Hz, 1H), 7.28-7.16 (m, 5H), 6.8 (s, 1H), 3.5 (s, 2H), 3.32-3.14 (m, 2H), 2.9 (t, J=12.0 Hz, 2H), 2.46-2.45 (m, 1H), 2.0 (t, J=4.0 Hz, 2H), 1.7 (t, J=12.0 Hz, 2H), 1.63-1.57 (m, 2H), 1.1 (t, J=12.0 Hz, 3H).

EXAMPLE 5-6: PREPARATION OF 5-((4-PHENYLPIPERIDIN-1-YL)METHYL)-N-PROPYLTHIAZOL-2-AMINE 5-((4-phenylpiperidin-1-yl)methyl)-N-propylthiazol-2-amine was prepared in a manner similar to that described for N-ethyl-5-((4-phenylpiperidin-1-yl)methyl)thiazol-2-amine (example 5-5), starting from tert-butyl (5-((4-phenylpiperidin-1-yl)methyl)thiazol-2-yl)carbamate and 1-iodopropane. Yield: 14% (8 mg, off-white solid). LC/MS: (Method B) 316.2 (M+H). HPLC: (Method A) RT.: 2.59 min, 99.6%, (Max), 99.2% (254 nm).

$^1$H NMR (400 MHz, DMSO-d$_6$): δ 7.4 (d, J=4.0 Hz, 1H), 7.28-7.14 (m, 5H), 6.8 (s, 1H), 3.5 (s, 2H), 3.13-3.08 (m, 2H), 2.9 (t, J=12.0 Hz, 2H), 2.45-2.42 (m, 2H), 2.01-1.96 (m, 2H), 1.73-1.70 (m, 2H), 1.64-1.48 (m, 4H), 0.9 (t, J=12.0 Hz, 3H).

EXAMPLE 5-9: PREPARATION OF N-METHYL-N-(5-((4-PHENYLPIPERIDIN-1-YL)METHYL)THIAZOL-2-YL)ACETAMIDE

Subsequent to Example 5a, to a stirred solution of N-methyl-5-((4-phenylpiperidin-1-yl)methyl)thiazol-2-amine (50 mg, 1 eq.) in pyridine (3 mL) at 0° C. was added acetyl chloride (0.05 mL, 6 eq.) and DMAP (catalytic). The reaction mixture was then allowed to stir at RT for 12 h. After completion of the reaction, the reaction mixture was concentrated under reduced pressure, water was added, and the product extracted with DCM. The organic phase was dried over Na$_2$SO$_4$, filtered, and concentrated under reduced pressure. The residue was subjected to preparative HPLC to afford the trifluoroacetate salt of N-methyl-N-(5-((4-phenylpiperidin-1-yl)methyl)thiazol-2-yl)acetamide as an off-white solid. Yield: 13% (10 mg). LC/MS: (Method A) 330.2 (M+H). HPLC: (Method A) RT.: 2.91 min, 98.9%, (Max), 95.0% (254 nm).

$^1$H NMR (400 MHz, DMSO-d$_6$): δ 7.32-7.21 (m, 4H), 7.17-7.14 (m, 1H), 3.7 (s, 2H), 3.6 (s, 3H), 2.9 (d, J=12.0 Hz, 2H), 2.49-2.45 (m, 1H), 2.4 (s, 3H), 2.06-2.01 (m, 2H), 1.73-1.60 (m, 4H).

EXAMPLE 5-10: PREPARATION OF 1-METHYL-3-(5-((4-PHENYLPIPERIDIN-1-YL)METHYL)THIAZOL-2-YL)UREA

Subsequent to Example 1, to a stirred solution of 5-((4-phenylpiperidin-1-yl)methyl)thiazol-2-amine hydrochloride (400 mg, 1 eq.) in dry THF (5 mL) at 0° C. was added Et$_3$N (261 mg, 2.0 eq.) and phosgene (0.35 eq.). The reaction mixture was then allowed to stir at RT for 30 min. The reaction mixture was again cooled to 0° C., and then treated with CH$_3$NH$_2$ in THF (2M, 1.2 eq.). The reaction mixture was allowed to stir at RT for 2 h. After completion of the reaction, the reaction mixture was concentrated under reduced pressure. Water was added and the product was extracted with DCM. The organic phase was dried over sodium sulfate, filtered, and concentrated under reduced pressure. The residue was subjected to preparative HPLC to afford the trifluoroacetate salt of 1-methyl-3-(5-((4-phenylpiperidin-1-yl)methyl)thiazol-2-yl)urea as a pale yellow solid. Yield: 5% (16 mg). LC/MS: (Method A) 331.0 (M+H). HPLC: (Method A) RT.: 2.87 min, 95.2%, (Max), 95.6% (254 nm).

$^1$H NMR (400 MHz, DMSO-d$_6$): δ 8.2 (s, 1H), 7.28-7.22 (m, 4H), 7.18-7.14 (m, 1H), 7.1 (s, 1H), 6.4 (d, J=4.0 Hz, 1H), 3.6 (s, 2H), 2.94-2.91 (m, 2H), 2.67-2.66 (m, 3H), 2.46-2.43 (m, 1H), 2.05-2.02 (m, 2H), 1.73-1.57 (m, 4H).

EXAMPLE 5-13: PREPARATION OF N-[5-(4-PHENYL-PIPERIDIN-1-YLMETHYL)-OXAZOL-2-YL]-ACETAMIDE

Step 1: Subsequent to Example 5b, step 4, to a solution of tert-butyl (5-((4-phenylpiperidin-1-yl)methyl)oxazol-2-yl)carbamate (80 mg, 1 eq.) in dry DCM (10 mL) at 0° C. was added DMAP (12 mg, 0.5 eq.) and acetyl chloride (0.02 mL, 1.5 eq.). The reaction mixture was allowed to stir at RT for 12 h. After completion of the reaction, the reaction was quenched by the addition of ice cold water and extracted with DCM. The organic phase was dried over sodium sulfate, filtered, and concentrated under reduced pressure. The residue was subjected to flash chromatography to afford tert-butyl acetyl(5-((4-phenylpiperidin-1-yl)methyl)oxazol-2-yl)carbamate as an off-white solid. Yield: 48% (80 mg). LC/MS: (Method A) 400.2 (M+H).

Step 2: To a solution of tert-butyl acetyl(5-((4-phenylpiperidin-1-yl)methyl)oxazol-2-yl)carbamate (1 eq) in dry 1,4-dioxane (5 mL) at 0° C. was added dioxane/HCl (1 mL). The reaction mixture was then allowed to stir at RT for 2 h. After completion of the reaction, the reaction mixture was concentrated under reduced pressure. The residue was subjected to preparative HPLC to afford the trifluoroacetate salt of N-(5-((4-phenylpiperidin-1-yl)methyl)oxazol-2-yl)acetamide as an off-white solid. Yield: 19% (12.2 mg). LC/MS: (Method A) 300.3 (M+H). HPLC: (Method A) RT.: 2.36 min, 97.5%, (Max), 98.7% (254 nm).

$^1$H NMR (400 MHz, DMSO-d$_6$): δ 11.1 (s, 1H), 7.28-7.14 (m, 5H), 6.9 (s, 1H), 3.5 (s, 2H), 2.9 (d, J=8.0 Hz, 2H), 2.41-2.40 (m, 1H), 2.09-1.99 (m, 5H), 1.73-1.57 (m, 4H).

EXAMPLE 6-17: PREPARATION OF 1-[5-(4-PHENYL-PIPERIDIN-1-YLMETHYL)-THIAZOL-2-YL]-PROPAN-2-ONE

Subsequent to Example 1-7, to a stirred solution of 2-methyl-5-((4-phenylpiperidin-1-yl)methyl)thiazole (200 mg, 0.73 mmol) in dry THF at −78° C. was added n-BuLi (1.6 M in hexane, 0.5 mL, 0.807 mmol). The reaction mixture was then stirred for 15 min. EtOAc (0.12 mL, 1.7 eq.) was then added and allowed to stir at −78° C. for 3 h. After completion of the reaction, the reaction mixture was quenched with saturated, aqueous $NH_4Cl$, extracted with DCM (10 mL), dried, and evaporated under reduced pressure. The crude product was purified by column chromatography to afford a pale yellow solid. Yield: 35% (75 mg). LC/MS: (Method A) 315.2 (M+H). HPLC: (Method A) RT.: 2.66 min, 93.7%, (Max), 90.7% (254 nm).

$^1$H NMR (400 MHz, DMSO-$d_6$): δ 7.54 (s, 1H), 7.28-7.14 (m, 5H), 4.21 (s, 2H), 3.70 (s, 2H), 2.94-2.91 (m, 2H), 2.46-2.45 (m, 1H), 2.19 (s, 3H), 2.08-2.03 (m, 2H), 1.73-1.65 (m, 4H).

EXAMPLE 6-18: PREPARATION OF 1-[5-(4-PHENYL-PIPERIDIN-1-YLMETHYL)-THIAZOL-2-YL]-BUTAN-2-ONE

Subsequent to Example 1-7, to a stirred solution of 2-methyl-5-((4-phenylpiperidin-1-yl)methyl)thiazole (150 mg, 0.5 mmol) in dry THF at −78° C. was added n-BuLi (1.6 M in hexane, 0.5 mL, 0.807 mmol) and stirred for 15 min. Methyl propionate (0.12 mL, 1.1 mmol) was then added and the reaction mixture was allowed to stir at −78° C. for 3 h. After completion of the reaction, the reaction was quenched by the addition of saturated aqueous $NH_4Cl$, extracted with DCM (10 mL), dried, and evaporated under reduced pressure. The crude product was purified by column chromatography to afford a pale yellow solid. Yield: 44% (57 mg). LC/MS: (Method A) 329.0 (M+H). HPLC: (Method A) RT.: 2.96 min, 98.7%, (Max), 97.7% (254 nm).

$^1$H NMR (400 MHz, DMSO-$d_6$): δ 7.54 (s, 1H), 7.28-7.16 (m, 5H), 4.19 (s, 2H), 3.70 (s, 2H), 2.94-2.91 (m, 2H), 2.59-2.43 (m, 3H), 2.08-2.02 (m, 2H), 1.73-1.65 (m, 4H), 1.84 (t, J=4.0 Hz, 3H).

EXAMPLE 7-2: PREPARATION OF [5-(4-PHENYL-PIPERIDIN-1-YLMETHYL)-THIAZOL-2-YL]-CARBAMIC ACID METHYL ESTER

[5-(4-Phenyl-piperidin-1-ylmethyl)-thiazol-2-yl]-carbamic acid methyl ester was prepared in a similar manner as described in Example 5-1, added by the particularities of Scheme 7.

EXAMPLE 7-11: PREPARATION OF N-[5-(4-PHENYL-PIPERIDIN-1-YLMETHYL)-THIAZOL-2-YL]-METHANESULFONAMIDE

To a stirred solution of 5-((4-phenylpiperidin-1-yl)methyl)thiazol-2-amine hydrochloride (20 mg, 1 eq.) in pyridine (2 mL) at 0° C. was added methane sulfonyl chloride (10 mg, 1.1 eq.) and DMAP (catalytic). The reaction mixture was then allowed to stir at RT for 3 h. After completion of the reaction, the reaction mixture was concentrated under reduced pressure and water was added. The product was extracted with DCM. The organic phase dried over sodium sulfate, filtered and concentrated under reduced pressure. The residue was subjected to flash chromatography to afford N-[5-(4-phenyl-piperidin-1-ylmethyl)-thiazol-2-yl]-methanesulfonamide as an off-white solid. Yield: 80% (19.4 mg). LC/MS: (Method A) 352.2 (M+H). HPLC: (Method A) RT.: 2.55 min, 94.2%, (Max), 92.0% (254 nm).

$^1$H NMR (400 MHz, DMSO-$d_6$): δ 12.2 (s, 1H), 7.29-7.14 (m, 6H), 3.5 (s, 2H), 2.96-2.87 (m, 5H), 2.09-2.04 (m, 2H), 1.75-1.62 (m, 4H).

EXAMPLE 8: PREPARATION OF N-(5-(1-(4-PHENYLPIPERIDIN-1-YL)ETHYL)THIAZOL-2-YL)ACETAMIDE (COMPOUND NO. 40)

Step 1: To a stirred solution of N-(5-formyl-thiazol-2-yl)-acetamide (1 g, 0.58 mmol) in dry THF (20 mL) at −78° C. was added MeMgBr (11.7 mL, 11.7 mmol). The reaction mixture was allowed to stir at RT for 5 h. After completion of reaction, the reaction was quenched by the addition of saturated, aqueous $NH_4Cl$ solution, and then the mixture was extracted with DCM. The organic layer was separated and dried over $Na_2SO_4$, filtered and concentrated under reduced pressure to afford the crude product, N-[5-(1-Hydroxy-ethyl)-thiazol-2-yl]-acetamide, which was used in the next step without further purification.

$^1$H NMR: (400 MHz, DMSO-$d_6$): δ 11.90 (s, 1H), 7.20 (s, 1H), 5.47 (d, J=6.2 Hz, 1H), 4.92-4.86 (m, 1H), 2.10 (s, 3H), 1.40 (d, J=4.5 Hz, 3H).

Step 2: To a stirred solution of N-[5-(1-hydroxy-ethyl)-thiazol-2-yl]-acetamide (0.27 g, 1.34 mmol) in dry THF (10 mL) was added $PPh_3$ (0.52 g, 1.20 mmol) and DIAD (0.4 mL, 2.01 mmol). The reaction mixture was allowed to stir at RT for 12 h. After completion of reaction, the reaction mixture was quenched by the addition of $H_2O$ solution and extracted with DCM. The organic layer was separated, dried over Na2SO4, filtered and concentrated under reduced pressure. The residue was subjected to column chromatography to afford N-(5-(1-(4-phenylpiperidin-1-yl)ethyl)thiazol-2-yl)acetamide as a colorless, gummy liquid. Yield: 54% (22 mg). LC/MS: (Method A) 330.2 (M+H). HPLC: Method A) RT.: 2.83 min, 98.5%, (Max), 98.8% (254 nm).

$^1$H NMR (400 MHz, DMSO-$d_6$): δ 11.91 (s, 1H), 7.29-7.14 (m, 6H), 3.97-3.92 (m, 1H), 2.96-2.81 (m, 2H), 2.50-2.49 (m, 1H), 2.20-2.10 (m, 5H), 1.76-1.60 (m, 4H), 1.32-1.29 (m, 3H).

EXAMPLE 9: SCHEME 9 (PROCEDURE C)—GENERAL PROCEDURE FOR AMINE ADDITION TO 5-(CHLOROMETHYL)THIAZOL-2-YL INTERMEDIATES

To a stirred solution of amine (0.5 to 1.2 eq.) in dry acetonitrile (5 to 10 mL), (5-(chloromethyl)thiazol-2-yl) intermediate (1 to 2 eq.) and TEA or DIPEA (2 to 4 eq.) were added at rt. The resulting solution was heated at 80° C. for 6 h. The reaction mixture was concentrated under vacuum and the resulting residue was diluted with DCM (20 to 50 mL). The DCM layer was washed with brine solution (5 to 10 mL), water (5 to 10 mL), dried over anhydrous $Na_2SO_4$ and concentrated under vacuum. The crude product was purified by column chromatography, by crystallization or precipitation to afford the pure product.

EXAMPLE 9A: PREPARATION OF N-(5-(CHLOROMETHYL)THIAZOL-2-YL) ACETAMIDE (INTERMEDIATE)

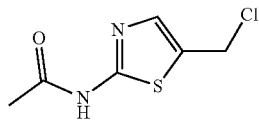

Step 1: To a stirred solution of ethyl-2-amino thiazole-5-carboxylate (10.0 g, 58.1 mmol), pyridine (9.47 mL, 116.27 mmol) and DMAP (200 mg, 1.6 mmol) in DCM (100 mL), acetic anhydride (8.89 g, 87.20 mmol) was added at 0° C. and refluxed for 2 h. The reaction mixture was concentrated under reduced pressure and HCl (1.5 N in water, 50 mL) was added. The mixture was stirred for 10 min. The resulting precipitate was filtered and washed with water (250 mL) and hexane (50 mL) to give ethyl 2-acetamidothiazole-5-carboxylate as an off-white solid. Yield: 98% (12.1 g). LC/MS: (Method C) 215.0 (M+H), RT. 2.77 min, 97.11% (Max).

$^1$H NMR (300 MHz, DMSO-d$_6$): δ 8.10 (s, 1H), 4.24 (q, J=6.2 Hz, 2H), 2.17 (s, 3H), 1.26 (t, J=6.2 Hz, 3H).

Step 2: To a stirred solution of ethyl 2-acetamidothiazole-5-carboxylate (4.0 g 18.6 mmol) in dry toluene (110 mL), lithium triethylborohydride (36.0 mL, 37.3 mmol, 1 M solution in THF) was added slowly at 0° C. The reaction mixture was stirred at rt for 2 h. The completion of the reaction was monitored by TLC. Reaction mixture was quenched with MeOH (2.0 mL). Water (20 mL) was added and the solution was stirred for 10 min. Two layers were separated and aqueous layer was washed with hexane (3×25 mL). The aqueous layer was acidified with AcOH (4 mL). The resulting precipitate was recovered by filtration, washed with water (10 mL) and hexane (20 mL) to give N-(5-(hydroxymethyl)thiazol-2-yl)acetamide as a white solid. Yield: 84% (2.7 g). LCMS: (Method C) 173.0 (M+H), RT. 2.02 min, 99.89% (Max).

$^1$H NMR (400 MHz, DMSO-d$_6$): δ 11.86 (s, 1H), 7.23 (br.s, 1H), 5.32 (s, 1H), 4.54 (s, 2H), 2.09 (s, 3H).

Step 3: To a stirred solution of N-(5-(hydroxymethyl) thiazol-2-yl)acetamide (10.0 g, 58.1 mmol) in dry DCM (27 mL), thionyl chloride (12.9 mL, 174.4 mmol) was added slowly at 0° C. and refluxed for 3 h. The reaction mixture was concentrated under reduced pressure. The resulting residue was co-distilled with DCM (2×50 mL) and Et$_2$O (50 mL) to give N-(5-(chloromethyl)thiazol-2-yl)acetamide as pale yellow solid. Yield: 92% (10.2 g). LCMS: (Method C) 187.0 (M+H), RT. 1.77 min, 90.36% (Max) (analytical sample was prepared in MeOH, yielding formation of methoxy adduct seen in the MS).

$^1$H NMR (400 MHz, DMSO-d$_6$): δ 12.18 (s, 1H), 7.50 (s, 1H), 5.02 (s, 2H), 2.14 (s, 3H).

EXAMPLE 9-46: PREPARATION OF N-(5-((4-(4-CHLOROBENZYL)PIPERIDIN-1-YL)METHYL) THIAZOL-2-YL)ACETAMIDE

N-(5-((4-(4-chlorobenzyl)piperidin-1-yl)methyl)thiazol-2-yl)acetamide was synthesized following general procedure C, using N-(5-(chloromethyl)thiazol-2-yl)acetamide (139 mg, 0.73 mmol), 4-[(4-chlorophenyl) piperidine hydrochloride (150 mg, 0.61 mmol, HDH Pharma), DIPEA (315 mg, 2.44 mmol) and ACN (10 mL). The crude was purified by Prep HPLC (Method C) to give the expected compound as off white solid. Yield: 9% (20 mg). LC/MS: (Method C) 364.0 (M+H). HPLC: (Method C) RT. 3.40 min, 95.9% (Max), 97.1% (254 nm).

$^1$H NMR (400 MHz, DMSO-d$_6$): δ 11.93 (s, 1H), 7.31 (d, J=8.4 Hz, 2H), 7.19 (t, J=8.4 Hz, 2H), 7.1 (s, 1H), 3.57 (s, 2H), 2.81-2.78 (m, 2H), 2.58-2.51 (m, 2H), 2.11 (s, 3H), 1.88-1.83 (m, 2H), 1.51-1.45 (m, 3H), 1.24-1.15 (m, 2H).

EXAMPLE 9-48: PREPARATION OF N-(5-((4-(4-FLUOROBENZYL)PIPERIDIN-1-YL)METHYL) THIAZOL-2-YL)ACETAMIDE

The title compound was synthesized following general procedure C, using N-(5-(chloromethyl)thiazol-2-yl)acetamide (300 mg, 1.57 mmol), 4-[(4-fluorophenyl) methylpiperidine (152 mg, 0.786 mmol, ISDI Inc. Chemicals), TEA (636 mg, 6.29 mmol) and ACN (4.5 mL). The crude product was purified by flash chromatography to give the title compound as yellow solid. Yield: 15% (84 mg). LC/MS: (Method C) 348.0 (M+H), HPLC: (Method C) RT. 3.07 min, 97.6% (Max), 95.6% (254 nm).

$^1$H NMR (400 MHz, DMSO-d$_6$): δ 11.93 (s, 1H), 7.21-7.16 (m, 3H), 7.01-7.05 (m, 2H), 3.56 (s, 2H), 2.81-2.78 (m, 2H), 2.50-2.47 (m, 2H), 2.10 (s, 3H), 1.88-1.82 (m, 2H), 1.52-1.44 (m, 3H), 1.19-1.15 (m, 2H).

EXAMPLE 9-55: PREPARATION OF N-(5-((4-(4-METHOXYBENZYL)PIPERIDIN-1-YL) METHYL)THIAZOL-2-YL)ACETAMIDE

The title compound was synthesized by following general procedure C, using N-(5-(chloromethyl)thiazol-2-yl)acetamide (240 mg, 1.24 mmol), 4-(4-methoxybenzyl)piperidine hydrochloride (300 mg, 1.24 mmol, Gencore Biopharma), DIPEA (518 mg, 3.73 mmol) and ACN (10 mL). The crude product was purified by flash chromatography to give the title compound as off white solid. Yield: 5% (22 mg). LC/MS: (Method C) 360.2 (M+H), HPLC: (Method C) RT. 2.93 min, 97.6% (Max), 96.5% (254 nm).

$^1$H NMR (400 MHz, DMSO-d$_6$): δ 11.92 (s, 1H), 7.21 (s, 1H), 7.05 (d, J=8.0 Hz, 2H), 6.82 (d, J=8.0 Hz, 2H), 3.71 (s, 3H), 3.56 (s, 2H), 2.81-2078 (m, 2H), 2.42 (d, J=7.2 Hz, 2H), 2.11 (s, 3H), 1.88-1.82 (m, 2H), 1.52-1.40 (m, 3H), 1.15-1.13 (m, 2H).

EXAMPLE 9B: PREPARATION OF 4-(5-(CHLOROMETHYL)THIAZOL-2-YL)PIPERAZIN-2-ONE (INTERMEDIATE)

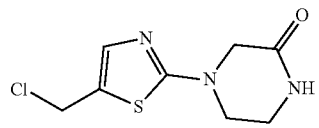 [SMILES: O=C1CN(c2ncc(CCl)s2)CCN1]

Step 1: To a stirred solution of ethyl-2-amino thiazole-5-carboxylate (10.0 g, 46.45 mmol, Combi block) in 48% HBr (75 mL), sodium nitrite (4.80 g, 69.68 mmol) dissolved in water (50 mL) was added drop wise at 0° C. and the reaction mixture was stirred at 0° C. for 15 min. Then copper(I) bromide (6.66 g, 46.45 mmol) in 48% HBr (75 mL) was added drop wise at 0° C. and the resulting reaction mixture was stirred at rt for 4 h. The reaction mixture was diluted with DCM (200 mL) and washed with water (50 mL), brine (50 mL), dried over Na$_2$SO$_4$ and concentrated under reduced pressure. The resulting crude was purified by flash chromatography (100% CHCl$_3$) to give ethyl 2-bromothiazole-5-carboxylate as a yellow liquid. Yield: 50% (5.5 g). LCMS: (Method A) 235.9 (M+H), RT. 3.85 min, 98.6% (Max).

$^1$H NMR (400 MHz, DMSO-d$_6$): δ 8.16 (s, 1H), 4.38 (q, J=7.1 Hz, 2H), 1.39 (t, J=7.1 Hz, 3H).

Step 2: To a stirred solution of ethyl 2-bromothiazole-5-carboxylate (0.75 g, 3.17 mmol) in dry DMF (6 mL), 2-oxapiperazine (0.318 g, 3.17 mmol) and triethyl amine (0.642 g, 6.3 mmol) were added at rt and the reaction mixture was stirred at 90° C. overnight. The reaction mixture was concentrated and the resulted crude was dissolved in 5% MeOH-DCM. The organic layer was washed with water, brine, dried over anhydrous Na$_2$SO$_4$ and concentrated to afford ethyl 2-(3-oxopiperazin-1-yl)thiazole-5-carboxylate as a off-white solid. Yield: 75% (0.61 g). LCMS: (Method A) 256.0 (M+H), RT. 2.38 min, 99.4% (Max).

$^1$H NMR (300 MHz, DMSO-d$_6$): δ 8.26 (s, 1H), 7.88 (s, 1H), 4.24-4.17 (m, 2H), 4.00 (s, 2H), 3.70-3.67 (m, 2H), 3.35-3.30 (m, 2H), 1.23 (t, J=7.0 Hz, 3H).

Step 3: To a stirred solution of ethyl 2-(3-oxopiperazin-1-yl)thiazole-5-carboxylate (0.5 g 1.95 mmol) in dry THF (10 mL), lithium triethylborohydride (3.9 mL, 3.91 mmol, 1 M solution in THF) was added slowly at 0° C. The react ion mixture was stirred at rt for 2 h. The completion of the reaction was monitored by TLC. Reaction mixture was cooled to 0° C. and quenched using methanol (10 mL) and concentrated under reduced pressure. The resulting crude product was purified by flash chromatography to give 4-(5-(hydroxymethyl)thiazol-2-yl)piperazin-2-one as off-white solid. Yield: 50% (210 mg). LCMS: (Method A) 214.0 (M+H), RT. 0.39 min, 92.9% (Max).

$^1$H NMR (300 MHz, DMSO-d$_6$): δ 8.13 (s, 1H), 7.00 (s, 1H), 5.26-5.22 (m, 1H), 4.42 (d, J=5.6 Hz, 2H), 3.87 (s, 2H), 3.58-3.54 (m, 2H).

Step 4: To a stirred solution of 4-(5-(hydroxymethyl) thiazol-2-yl)piperazin-2-one (180 g, 0.84 mmol) in dry DCM (1.8 mL), thionyl chloride (0.12 mL, 1.68 mmol) was added slowly at 0° C. and refluxed for 3 h. The reaction mixture was concentrated under reduced pressure. The resulting residue was co-distilled with DCM (2×10 mL) to give 4-(5-(chloromethyl)thiazol-2-yl)piperazin-2-one as yellow gum and used in the next step without further purification. Yield: 92% (0.18 g). LCMS: (Method A) 228.0 (M+H, MeOH adduct), RT. 0.85 min, 84.7% (Max).

EXAMPLE 9-59: PREPARATION OF 4-(5-((4-(1-(BENZO[D][1,3]DIOXOL-5-YL)ETHYL)PIPER-AZIN-1-YL)METHYL)THIAZOL-2-YL)PIPER-AZIN-2-ONE

The title compound was synthesized by following general procedure C, with 4-(5-(chloromethyl)thiazol-2-yl)piperazin-2-one (0.18 g, 1.17 mmol), 1-(1-(benzo[d][1,3]dioxol-5-yl)ethyl)piperazine hydrochloride (0.139 g, 0.62 mmol), TEA (0.235 g, 2.33 mmol) and ACN (3.6 mL). The crude was purified by flash column chromatography to obtain the title compound as off-white solid. Yield: 24% (87.49 mg). LC/MS: (Method C) 430.0 (M+H), HPLC: (Method C) RT 1.86 min, 97.1% (Max), 98.2% (254 nm).

$^1$H NMR (400 MHz, CD$_3$OD): δ 7.06 (s, 1H), 6.92 (s, 1H), 6.83 (s, 2H), 5.97 (s, 2H), 4.06 (s, 2H), 3.71-3.68 (m, 5H), 3.48-3.46 (m, 3H), 2.85-2.52 (m, 7H), 1.50 (s, 3H).

EXAMPLE 9-61: PREPARATION OF N-(5-((4-PHENOXYPIPERIDIN-1-YL)METHYL)THI-AZOL-2-YL)ACETAMIDE

The title compound was synthesized by following general procedure C, using N-(5-(chloromethyl)thiazol-2-yl)acetamide (500 mg, 2.9 mmol), 4-phenoxypiperidine (250 mg, 1.45 mmol, Gencore Biopharma), TEA (1.17 g, 11.62 mmol) and ACN (8 mL). The crude was purified by column chromatography to give the title compound as yellow solid. Yield: 5% (43 mg). LC/MS: (Method A) 332.0 (M+H), HPLC: (Method A) RT. 2.77 min, 96.8% (Max), 95.1% (254 nm).

$^1$HNMR (400 MHz, DMSO-d$_6$): δ 11.95 (s, 1H), 7.27-7.23 (m, 3H), 6.93-6.87 (m, 3H), 4.38-4.35 (m, 1H), 3.64 (s, 2H), 2.69-2.66 (m, 2H), 2.31-2.23 (m, 2H), 2.10 (s, 3H), 1.93-1.90 (m, 2H), 1.63 (m, 2H).

EXAMPLE 9-62: PREPARATION OF N-(5-((4-PHENETHYLPIPERIDIN-1-YL)METHYL)THI-AZOL-2-YL)ACETAMIDE

The title compound was synthesized by following general procedure C, using N-(5-(chloromethyl)thiazol-2-yl)acetamide (500 mg, 2.9 mmol), 4-phenethylpiperidine (270 mg, 1.45 mmol, Fchemicals), TEA (1.17 g, 11.62 mmol) and ACN (8 mL). The crude was purified by titration to give the title compound as brown solid. Yield: 12% (12 mg). LC/MS: (Method C) 344.2 (M+H), HPLC: (Method C) RT. 3.45 min, 98.9% (Max), 96.7% (254 nm).

$^1$H NMR (400 MHz, DMSO-d$_6$): δ 11.92 (s, 1H), 7.27-7.21 (m, 3H), 7.18-7.12 (m, 3H), 3.57 (s, 2H), 2.80 (d, J=10.8 Hz, 2H), 2.56-2.51 (m, 2H), 2.10 (s, 3H), 1.89-1.84 (m, 2H), 1.66 (d, J=9.6 Hz, 2H), 1.50-1.45 (m, 2H), 1.18-1.12 (m, 3H).

EXAMPLE 10B: PREPARATION OF 4-(BENZO [D][1,3]DIOXOL-5-YLMETHYL)PIPERIDINE HYDROCHLORIDE (INTERMEDIATE)

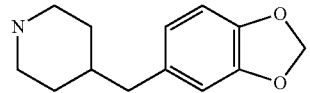 [SMILES: c1cc2c(cc1CC1CCNCC1)OCO2]

Step 1: To a stirred solution of 5-(bromomethyl)benzo[d] [1,3]dioxole (1 g, 4.65 mmol) in toluene (10 mL), triphenyl phosphine (1.2 g, 4.65 mmol) was added. The reaction mixture was refluxed for 2 h. The completion of the reaction was monitored by TLC. Then the reaction mixture was concentrated under vacuum and triturated with diethyl ether. The solid obtained was filtered, washed with diethyl ether, dried and taken for next step without any further purification. (Benzo[d][1,3]dioxol-5-ylmethyl)bromotriphenylphosphane was isolated as white solid. Yield: 82% (1.8 g). LCMS: (Method C) 397.0 (M-Br), RT. 4.21 min, 97.2% (Max).

$^1$H NMR (400 MHz, DMSO-d$_6$): δ 7.94-7.90 (m, 3H), 7.79-7.74 (m, 6H), 7.70-7.64 (m, 6H), 6.81-6.79 (m, 1H), 6.47-6.44 (m, 2H), 5.98 (s, 2H), 5.07-5.03 (m, 2H).

Step 2: To a stirred solution of (benzo[d][1,3]dioxol-5-ylmethyl)bromotriphenyl-phosphane (1.0 g, 4.65 mmol) in THF (10 mL), potassium tert-butoxide (423 mg, 3.77 mmol) was added at 0° C. The reaction mixture was stirred at rt for 2 h. 1-Boc piperidin-4-one (375 mg, 1.88 mmol) in THF (10 mL) was added at 0° C. The reaction mixture was stirred at rt for 2 h. The completion of the reaction was monitored by TLC. Then the reaction mixture was concentrated under vacuum and the crude mixture was dissolved in ethyl acetate, washed with water, dried over sodium sulfate and evaporated. It was purified by flash column chromatography to get tert-butyl 4-(benzo[d][1,3]dioxol-5-ylmethylene)piperidine-1-carboxylate as a pale brown solid. Yield: 58%. LCMS: (Method C) 262.0 (M-t-Bu+H), RT. 5.58 min, 95.9% (Max).

$^1$H NMR (400 MHz, DMSO-$d_6$): δ 6.88 (d, J=7.9 Hz, 1H), 6.79 (s, 1H), 6.69 (dd, J=1.2, 8.0 Hz, 1H), 6.28 (s, 1H), 6.00 (s, 2H), 3.39 (t, J=5.8 Hz, 2H), 3.33-3.31 (m, 2H), 2.37 (t, J=5.6 Hz, 2H), 2.24 (t, J=5.5 Hz, 2H), 1.41 (s, 9H).

Step 3: To a stirred solution of tert-butyl 4-(benzo[d][1,3]dioxol-5-ylmethylene)piperidine-1-carboxylate (350 mg, 1.10 mmol) in methanol (10 mL), 10% Pd/C (100 mg) was added. The reaction mixture was stirred under hydrogen pressure (2 kg/cm$^3$) at rt for 2 h. It was then filtered through celite, concentrated under vacuum and the crude mixture was taken for next step without any further purification. Tert-butyl 4-(benzo[d][1,3]dioxol-5-ylmethyl)piperidine-1-carboxylate was isolated as off-white solid. Yield: 80% (280 mg). LCMS: (Method C) 264.0 (M-t-Bu+H), RT. 5.61 min, 95.7% (Max).

$^1$H NMR (400 MHz, DMSO-$d_6$): δ 6.80-6.74 (m, 2H), 6.60-6.57 (m, 1H), 5.94 (s, 2H), 3.90-3.86 (m, 2H), 2.71-2.49 (m, 2H), 2.41-2.38 (m, 3H), 1.52-1.48 (m, 2H), 1.36 (s, 9H), 0.98-0.94 (m, 2H).

Step 4: Tert-butyl 4-(benzo[d][1,3]dioxol-5-ylmethyl)piperidine-1-carboxylate (280 mg, 319.4 mmol) was dissolved in HCl solution in dioxane (1 mL, 4 M). The reaction mixture was stirred at rt for 1 h. After completion of the reaction, it was concentrated under reduced pressure to afford the hydrochloride salt of 4-(benzo[d][1,3]dioxol-5-ylmethyl)piperidine hydrochloride as a white solid. Yield: 99% (220 mg).

$^1$H NMR (400 MHz, DMSO-$d_6$): δ 6.82-6.76 (m, 2H), 6.63-6.58 (m, 1H), 5.97 (s, 2H), 3.94-3.89 (m, 2H), 2.73-2.51 (m, 2H), 2.41-2.38 (m, 3H), 1.52-1.48 (m, 2H), 0.98-0.94 (m, 2H).

EXAMPLE 10-47: PREPARATION OF N-(5-((4-(BENZO[D][1,3]DIOXOL-5-YLMETHYL)PIPERIDIN-1-YL)METHYL)THIAZOL-2-YL)ACETAMIDE

The title compound was synthesized following general procedure C, using N-(5-(chloromethyl)thiazol-2-yl)acetamide (149 mg, 0.78 mmol), 4-(benzo[d][1,3]dioxol-5-ylmethyl)piperidine hydrochloride (220 mg, 0.78 mmol), DIPEA (302 mg, 2.34 mmol) and DMF (10 mL). The crude product was purified by flash chromatography to give the title compound as pale brown solid. Yield: 7% (20 mg). LCMS: (Method C) 374.0 (M+H). HPLC: (Method C) RT. 2.91 min, 95.9% (Max), 97.1% (254 nm).

$^1$H NMR (400 MHz, DMSO-$d_6$): δ 11.93 (s, 1H), 7.21 (s, 1H), 6.79 (d, J=8.0 Hz, 1H), 6.74 (s, 1H), 6.59 (d, J=7.6 Hz, 1H), 5.95 (s, 2H), 3.56 (s, 2H), 2.81-2.78 (m, 2H), 2.41-2.40 (m, 2H), 2.11 (s, 3H), 1.85-1.77 (m, 2H), 1.53-1.41 (m, 3H), 1.18-1.10 (m, 2H).

EXAMPLE 10D: PREPARATION OF 4-(4-(TRIFLUOROMETHYL)BENZYL)PIPERIDINE HYDROCHLORIDE (INTERMEDIATE)

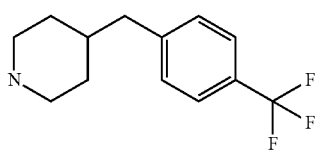 [SMILES: FC(F)(F)c1ccc(CC2CCNCC2)cc1]

Step 1: To 1-(bromomethyl)-4-(trifluoromethyl)benzene (4.0 g, 16.7 mmol), triethyl phosphite (3.7 mL, 22.0 mmol) was added at rt and the mixture was refluxed at 150° C. overnight. The reaction mixture was cooled and evaporated under vacuum. The crude product was taken for next step without further purification. Triethoxy(4-(trifluoromethyl)benzyl)phosphonium bromide was isolated as colorless liquid. Yield: 91% (6.1 g). LCMS: (Method C) 297.0 (M+H), RT. 4.35 min, 96.92% (Max).

$^1$H NMR (400 MHz, DMSO-$d_6$): δ 7.66 (d, J=12.0 Hz, 2H), 7.48 (d, J=8.0 Hz, 2H), 3.97-3.94 (m, 6H), 2.49-2.48 (m, 2H), 1.23-1.21 (m, 9H).

Step 2: To a stirred solution of triethoxy(4-(trifluoromethyl)benzyl)phosphonium bromide (6.1 g, 15.0 mmol), 15-crown-5 ether (0.27 g, 1.2 mmol) in dry THF (35 mL), NaH (60%, 0.59 g, 14.4 mmol) was added at 0° C. and stirred for 1 h. 1-Boc piperdin-4-one (2.5 g, 12.6 mmol) in THF (25 mL) was then added at the same temperature and the mixture was stirred at rt overnight. Reaction mixture was quenched with ice water and extracted with EtOAc (120 mL). The organic layer was washed with 10% NaHCO$_3$ (20 mL), water (20 mL), brine (15 mL) and dried over Na$_2$SO$_4$ and concentrated. The crude product was purified by silica gel column chromatography to get tert-butyl 4-(4-(trifluoromethyl) benzylidene)piperidine-1-carboxylate as a white solid. Yield: 84% (4.3 g). LCMS: (Method C) 242.0 (M+H), RT. 6.24 min, 98.79% (Max).

$^1$H NMR (400 MHz, DMSO-$d_6$): δ 7.66 (d, J=8.0 Hz, 2H), 7.42 (d, J=8.0 Hz, 2H), 6.43 (s, 1H), 3.43-3.39 (m, 2H), 3.35-3.31 (m, 2H), 2.40-2.36 (m, 2H), 2.31-2.28 (m, 2H), 1.22 (s, 9H).

Step 3: To a stirred solution of tert-butyl 4-(4-(trifluoromethyl) benzylidene)piperidine-1-carboxylate (3.8 g, 11.1 mmol) in dry MeOH (100 mL), Pd/C (0.380 g, 10%) was added under nitrogen. The reaction mixture was stirred under hydrogen pressure (2 kg/cm$^3$) at rt for 2 h. The reaction mixture was then filtered through celite and concentrated to give tert-butyl 4-(4-(trifluoromethyl)benzyl)piperidine-1-carboxylate as a white solid. Yield: 84% (3.2 g). LCMS: (Method C) 244.0 (M+H), RT. 6.25 min, 99.66% (Max).

$^1$H NMR (400 MHz, DMSO-$d_6$): δ 7.61 (d, J=8.0 Hz, 2H), 7.38 (d, J=8.0 Hz, 2H), 4.09-4.05 (m, 1H), 3.89-3.86 (m, 2H), 3.20-3.14 (m, 2H), 2.59-2.57 (m, 4H), 1.51-1.47 (m, 2H), 1.36 (s, 9H).

Step 4: To a stirred solution of tert-butyl 4-(4-(trifluoromethyl)benzyl)piperidine-1-carboxylate (3.2 g, 9.3 mmol) in 1,4-dioxane (6 mL), HCl solution in dioxane (30 mL, 4 M) was added at rt and stirred for 2 h. The reaction mixture was concentrated. The resulting crude product was washed with diethyl ether and used as such without further purification in the synthesis of EXAMPLE 10-49. 4-(4-(trifluoromethyl)benzyl)piperidine hydrochloride was isolated as off-white solid. Yield: 85% (2 g). LCMS: (Method C) 244.0 (M+H), RT. 3.41 min, 99.20% (Max).

$^1$H NMR (400 MHz, DMSO-$d_6$): δ 7.64 (d, J=8.0 Hz, 2H), 7.41 (d, J=8.0 Hz, 2H), 3.36 (m, 2H), 2.77-2.73 (m, 3H), 2.61 (d, J=12.0 Hz, 2H), 1.84-1.81 (m, 1H), 1.68-1.63 (m, 2H), 1.39-1.35 (m, 2H).

EXAMPLE 10-49: PREPARATION OF N-(5-((4-(4-(TRIFLUOROMETHYL)BENZYL)PIPERIDIN-1-YL)METHYL)THIAZOL-2-YL)ACETAMIDE

The title compound was synthesized by following general procedure C, using N-(5-(chloromethyl)thiazol-2-yl)acetamide (490 mg, 2.57 mmol), 4-(4-(trifluoromethyl)benzyl)

piperidine hydrochloride (600 mg, 2.15 mmol), DIPEA (867 mg, 6.89 mmol) and ACN (10 mL). The crude was purified by flash chromatography to give the title compound as brown solid. Yield: 1% (8 mg). LC/MS: (Method C) 398.0 (M+H), HPLC: (Method C) RT. 3.71 min, 97.6% (Max), 96.9% (254 nm).

$^1$H NMR (400 MHz, DMSO-d$_6$): δ 11.93 (s, 1H), 7.62 (d, J=8.0 Hz, 2H), 7.39 (d, J=8.0 Hz, 2H), 7.21 (s, 1H), 3.57 (s, 2H), 2.81-2.78 (m, 2H), 2.59 (d, J=6.4 Hz, 2H), 2.11 (s, 3H), 1.88-1.83 (m, 2H), 1.52-1.49 (m, 3H), 1.23-1.18 (m, 2H).

EXAMPLE 10E: PREPARATION OF 4-(3-FLUOROBENZYL)PIPERIDINE HYDROCHLORIDE (INTERMEDIATE)

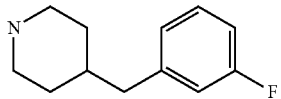 [SMILES: Fc1cccc(CC2CCNCC2)c1]

Step 1: To 1-(bromomethyl)-3-fluorobenzene (2.3 g, 11.6 mmol), triethyl phosphite (2.7 mL, 15.3 mmol) was added at rt and the mixture was refluxed at 150° C. overnight. The reaction mixture was cooled to rt and evaporated under vacuum. The crude product was taken for next step without further purification. Triethoxy (3-fluorobenzyl)phosphonium bromide was isolated as colorless liquid. Yield: 76% (3.2 g). LCMS: (Method C) 247.0 (M-Et-Br+H), RT. 3.67 min, 97.58% (Max).

$^1$H NMR (400 MHz, DMSO-d$_6$): δ 7.35-7.34 (m, 1H), 7.10-7.09 (m, 3H), 3.96-3.95 (m, 6H), 3.31-3.24 (m, 2H), 1.23-1.20 (m, 9H).

Step 2: To a stirred solution of triethoxy (3-fluorobenzyl) phosphonium bromide (3.2 g, 9.03 mmol) and 15-crown-5 ether (0.16 g, 0.7 mmol) in dry THF (25 mL), NaH (60%, 0.33 g, 8.1 mmol) was added at 0° C. and stirred for 1 h. A solution of 1-boc piperdin-4-one (1.5 g, 7.71 mmol) in THF (15 mL) was then added and the mixture was stirred at rt overnight. Reaction mixture was quenched with ice water, extracted with ethyl acetate (100 mL). The organic layer was washed with 10% NaHCO$_3$ (20 mL), water and brine. The organic layer was dried over Na$_2$SO$_4$ and concentrated. The crude product was purified by silica gel column chromatography to give tert-butyl 4-(3-fluorobenzylidene)piperidine-1-carboxylate as colorless liquid. Yield: 55% (1.5 g). LCMS: (Method C) 192.2 (M-Boc+H), RT. 5.79 min, 98.67% (Max).

$^1$H NMR (400 MHz, DMSO-d$_6$): δ 7.38-7.36 (m, 1H), 7.07-7.02 (m, 3H), 6.3 (s, 1H), 3.42-3.40 (m, 2H), 3.34 (d, J=8.0 Hz, 2H), 2.40-2.39 (s, 3H), 2.40-2.39 (s, 3H). 2.40-2.37 (s, 2H). 2.30-2.27 (s, 2H), 1.41 (s, 9H).

Step 3: To a stirred solution of tert-butyl 4-(3-fluorobenzylidene)piperidine-1-carboxylate (1.5 g, 11.1 mmol) in dry MeOH (75 mL), Pd/C (0.150 g, 10%) was added under nitrogen. The reaction mixture was stirred under hydrogen pressure (2 kg/cm$^3$) at rt for 2 h. It was filtered through celite, concentrated, affording tert-butyl 4-(3-fluorobenzyl)piperidine-1-carboxylate as colorless liquid. Yield: 73% (1.1 g). LCMS: (Method C) 194.2 (M-Boc+H), RT. 5.82 min, 98.76% (Max).

$^1$H NMR (400 MHz, DMSO-d$_6$): δ 7.33-7.25 (m, 1H), 7.01-6.96 (m, 3H), 3.90-3.58 (m, 2H), 2.61-2.51 (m, 4H), 1.76-1.65 (m, 3H), 1.30 (s, 9H) 0.90-0.81 (m, 2H).

Step 4: To a stirred solution of tert-butyl 4-(3-fluorobenzyl)piperidine-1-carboxylate (1.1 g, 3.7 mmol) in 1,4-dioxane (6 mL), HCl solution in dioxane (10 mL, 4M) added at rt and the mixture was stirred for 2 h. It was concentrated. The crude product was washed with diethyl ether (5 mL) and used as such without further purification for the synthesis of EXAMPLE 10-50. 4-(3-fluorobenzyl)piperidine hydrochloride was isolated as off white solid. Yield: 90% (0.9 g). LCMS: (Method C) 194.0 (M+H), RT. 2.77 min, 90% (Max).

$^1$H NMR (400 MHz, DMSO-d$_6$): δ 7.35-7.28 (m, 1H), 7.04-6.98 (m, 3H), 3.21-3.16 (m, 2H), 2.79-2.71 (m, 2H), 2.51 (d, J=9.4 Hz, 2H), 1.81-1.75 (m, 1H), 1.68-1.63 (m, 2H) 1.30-1.25 (m, 2H).

EXAMPLE 10-50: PREPARATION OF N-(5-((4-(3-FLUOROBENZYL)PIPERIDIN-1-YL)METHYL)THIAZOL-2-YL)ACETAMIDE

The title compound was synthesized by following general procedure C, using N-(5-(chloromethyl)thiazol-2-yl)acetamide (300 mg, 1.57 mmol), 4-(3-fluorobenzyl)piperidine hydrochloride (350 mg, 1.53 mmol), DIPEA (740 mg, 4.6 mmol) and ACN (10 mL). The crude was purified by flash chromatography to give the title compound as brown solid. Yield: 13% (67 mg). LC/MS: (Method C) 348.2 (M+H), HPLC: (Method C) RT. 3.09 min, 98.5% (Max), 96.1% (254 nm).

$^1$H NMR (400 MHz, DMSO-d$_6$): δ 11.93 (s, 1H), 7.33-7.27 (m, 1H), 7.22 (s, 1H), 7.01-6.97 (m, 3H), 3.57 (s, 2H), 2.81-2.78 (m, 2H), 2.51-2.50 (m, 2H), 2.11 (s, 3H), 1.89-1.84 (m, 2H), 1.52-1.49 (m, 3H), 1.21-1.13 (m, 2H).

EXAMPLE 10F: PREPARATION OF 4-BENZYL-2-METHYLPIPERIDINE HYDROCHLORIDE (INTERMEDIATE)

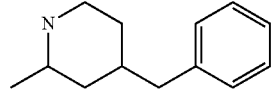

Step 1: To a stirred solution of benzyltriphenylphosphonium bromide (8.1 g, 18.7 mmol) in dry THF (20 mL), was added potassium tert-butoxide (2.0 g, 17.8 mmol) at rt. The resulting mixture was stirred 1 h. Tert-butyl-2-methyl-4-oxopiperidine-1-carboxylate (2.0 g, 9.3 mmol) was then added at the same temperature and the reaction mixture was stirred for 3 h. Solvents were evaporated. Water (20 mL) was added to the resulting crude product and was extracted with DCM (80 mL). The organic layer was dried over Na$_2$SO$_4$ and concentrated. The crude product was purified by silica gel column chromatography (5% EtOAc in hexane) to get tert-butyl 4-benzylidene-2-methylpiperidine-1-carboxylate as a colorless gummy liquid. Yield: 59% (1.4 g). LCMS: (Method C) 232 (M-t-Bu+H), RT. 6.05 min, 95.8% (Max).

$^1$H NMR (400 MHz, DMSO-d$_6$): δ 7.36-7.31 (m, 2H), 7.31-7.19 (m, 3H), 6.50-6.35 (m, 1H), 4.36-4.32 (m, 1H), 3.95-3.82 (m, 1H), 2.93 (d, J=11.8 Hz, 1H), 2.73-2.69 (m, 1H), 2.50-2.14 (m, 3H), 1.35 (s, 9H), 1.01 (d, J=8.0 Hz, 3H).

Step 2: To a stirred solution of tert-butyl 4-benzylidene-2-methylpiperidine-1-carboxylate (1.4 g, 4.87 mmol) in dry MeOH (10 mL), was added Pd/C (200 mg, 10%, Aldrich) under nitrogen. The reaction mixture was stirred under hydrogen pressure (2 kg/cm$^3$) at rt for 2 h. the reaction mixture was concentrated and dried under vacuum to afford tert-butyl 4-benzyl-2-methylpiperidine-1-carboxylate as a brown liquid. Yield: 80% (1.2 g). LCMS: (Method C) 234 (M-t-Bu+H), RT. 6.07 min, 96.68% (Max).

$^1$H NMR (400 MHz, DMSO-d$_6$): δ 7.26-7.24 (m, 2H), 7.27-7.23 (d, 3H), 3.68-3.51 (m, 1H), 3.51-3.49 (d, 1H), 3.33-3.11 (m, 1H), 2.58-2.55 (m, 1H), 2.47-2.44 (m, 1H), 1.76-1.55 (m, 4H), 1.35 (s, 9H), 1.12 (s, 3H), 0.98-1.01 (m, 1H).

Step 3: To a stirred solution of tert-butyl 4-benzyl-2-methylpiperidine-1-carboxylate (1.2 g, 4.15 mmol) in 1,4-dioxane (10 mL), HCl solution in dioxane (20 mL, 4 M) was added at rt and stirred for 2 h. The reaction mixture was concentrated. The crude product was washed with diethyl ether (5 mL) and was used as such for next step without further purification for the synthesis of EXAMPLE 10-51. 4-Benzyl-2-methylpiperidine hydrochloride was isolated as pale blue solid. Yield: 98% (0.85 g). LCMS: (Method C) 190.02 (M+H), RT. 2.79 min, 95.04% (Max).

EXAMPLE 10-51: PREPARATION OF N-(5-((4-BENZYL-2-METHYLPIPERIDIN-1-YL)METHYL)THIAZOL-2-YL)ACETAMIDE

The title compound was synthesized by following general procedure C, using N-(5-(chloromethyl)thiazol-2-yl)acetamide (300 mg, 1.57 mmol), 4-benzyl-2-methylpiperidine hydrochloride (350 mg, 1.56 mmol), DIPEA (740 mg, 4.6 mmol) and ACN (10 mL). The crude was purified by column chromatography to give the title compound as brown solid. Yield: 7% (32 mg). LC/MS: (Method C) 344.2 (M+H), HPLC: (Method C) RT. 3.11 min, 98.9% (Max), 97.2% (254 nm).

$^1$H NMR (400 MHz, DMSO-d$_6$): δ 11.93 (s, 1H), 7.28-7.22 (m, 3H), 7.18-7.13 (m, 3H), 3.95 (d, J=14.8 Hz, 1H), 3.55 (d, J=14.0 Hz, 1H), 2.77-2.74 (m, 1H), 2.50-2.44 (m, 2H), 2.11 (br. s, 5H), 1.97-1.91 (m, 1H), 1.49-1.39 (m, 3H), 1.08-1.06 (m, 4H).

EXAMPLE 10G: PREPARATION OF 4-BENZYL-3-FLUOROPIPERIDINE HYDROCHLORIDE (INTERMEDIATE)

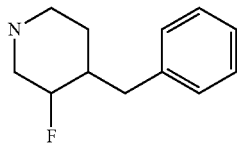 [SMILES: FC1CNCCC1Cc1ccccc1]

Step 1: To a stirred solution of 1-Boc piperidine 4-one (20.0 g, 0.10 mol, spectrochem) in dry DMF (50 mL) was added triethyl amine (33.5 mL, 0.24 mol) followed by trimethyl silyl chloride (15.2 g, 0.12 mol, chempure) reaction mass was sealed tightly and heated at 80° C. for 20 h. Reaction mass evaporated, dissolved in ethyl acetate, washed with water, dried over sodium sulfate and evaporated. The crude product was taken for next step without further purification. Tert-butyl 4-((tert-butylsilyl)oxy)-3,6-dihydropyridine-1 (2H)-carboxylate was isolated as brown liquid. Yield: 92% (25.0 g).

$^1$H NMR (400 MHz, DMSO-d$_6$): δ 3.98-3.95 (m, 1H), 3.72 (t, J=8.16 Hz, 2H), 2.96-2.89 (m, 1H), 1.51-1.47 (m, 2H), 1.47 (s, 9H), 0.16 (s, 9H).

Step 2: To a stirred solution of tert-butyl 4-((tert-butylsilyl)oxy)-3,6-dihydropyridine-1 (2H)-carboxylate (25.0 g, 0.09 mol) in dry acetonitrile (200 mL) was added 1-(chloromethyl)-4-fluoro-1,4-diazoniabicyclo[2.2.2]octane ditetrafluoroborate (select fluor) (35.8 g, 0.101 mol). Reaction mass stirred at rt for 1 h. Reaction mass diluted with ethyl acetate washed with water, dried over sodium sulfate and evaporated. The crude product was purified by silica gel flash column chromatography to get tert-butyl 3-fluoro-4-oxopiperidine-1-carboxylate as an off-white solid. Yield: 73% (8.1 g). LCMS: (Method C) 118.2 (M-Boc+H), RT. 2.53 min, 96.5% (ELSD).

$^1$H NMR (400 MHz, DMSO-d$_6$): δ 4.92-4.89 (m, 1H), 4.76-4.73 (m, 1H), 4.21-4.17 (m, 1H), 3.30-3.20 (m, 2H), 2.60-2.45 (m, 2H), 1.47 (s, 9H).

Step 3: To a stirred solution of benzyltriphenylphosphonium bromide (10.0 g, 18.3 mmol) in dry THF (20 mL), was added potassium tert-butoxide (2.0 g, 9.21 mmol) at rt and for 1 h. Then tert-butyl 3-fluoro-4-oxopiperidine-1-carboxylate (1.8 g, 18.3 mmol) was added at the same temperature and the reaction mixture was stirred for 3 h. The reaction mixture was concentrated. To the resulting crude mixture, water was added and extracted with DCM (80 mL). The organic layer was dried over Na$_2$SO$_4$ and concentrated. The crude product was purified by silica gel column chromatography (5% EtOAc in hexane) to get tert-butyl 4-benzylidene-3-fluoropiperidine-1-carboxylate as a yellow solid. Yield: 57% (1.6 g).

$^1$H NMR (400 MHz, DMSO-d$_6$): δ 7. 39-7.32 (m, 2H), 7.30-7.24 (m, 3H), 6.68 (s, 1H), 5.36 (d, J=46 Hz, 1H), 4.43-4.07 (m, 2H), 3.11-2.60 (m, 4H), 1.50 (s, 9H).

Step 4: To a stirred solution of tert-butyl 4-benzylidene-3-fluoropiperidine-1-carboxylate (1.6 g, 5.4 mmol) in dry MeOH (10 mL), was added Pd/C (200 mg, 10%, Aldrich) under nitrogen. The reaction mixture was stirred under hydrogen pressure (2 kg/cm$^3$) at rt for 2 h. The reaction mixture was filtered and concentrated. The resulting crude mixture was purified by flash column chromatography (2 to 5% EtOAc in petroleum ether) to give two isomers. Total yield: 33%.

First eluting isomer: 14% (0.55 g, colorless liquid). $^1$H NMR (400 MHz, DMSO-d$_6$) b 7.31-7.28 (m, 2H), 7.23-7.14 (m, 3H), 4.08 (d, J=13.2 Hz, 1H), 2.68-2.61 (m, 2H), 2.55 (d, J=6.9 Hz, 2H), 1.68-1.57 (m, 3H), 1.46 (s, 9H), 1.27-1.15 (m, 2H).

Second eluting isomer: 19% (0.29 g, colorless liquid). $^1$H NMR (400 MHz, DMSO-d$_6$) Isomer 2: δ 7.32-7.29 (m, 2H), 7.23-7.13 (m, 3H), 4.45 (d, J=46.8 Hz, 1H), 2.90-2.80 (m, 2H), 2.65-2.63 (m, 2H), 2.54-2.50 (m, 2H), 1.37 (s, 9H), 1.37-1.36 (m, 2H). The second eluting isomer was used in the next step.

Step 5: To a stirred solution of tert-butyl 4-benzyl-3-fluoropiperidine-1-carboxylate (second eluting isomer) (0.29 g, 1.5 mmol) in 1,4-dioxane (10 mL), HCl solution in dioxane (10 mL, 4 M) was added at rt and stirred for 2 h. The reaction mixture was concentrated. The resulting crude product was washed with diethyl ether (5 mL) and used as such, as single isomer, in the synthesis of EXAMPLE 10-52. 4-Benzyl-3-fluoropiperidine hydrochloride was isolated as white solid. Yield: 98% (0.18 g). LCMS: (Method C) 194.2 (M+H), RT. 2.5-2.6 min, 95.3% (Max).

$^1$H NMR (400 MHz, DMSO-d$_6$): δ 9.42 (s, 1H), 8.50 (s, 1H), 7.33-7.14 (m, 5H), 4.77-4.61 (s, 1H), 3.54-3.28 (m, 4H), 3.17-2.99 (m, 5H), 2.56-2.42 (m, 2H), 1.57-1.15 (m, 2H).

EXAMPLE 10-52: PREPARATION OF N-(5-((-4-BENZYL-3-FLUOROPIPERIDIN-1-YL)METHYL)THIAZOL-2-YL)ACETAMIDE

The title compound was synthesized by following general procedure C, using N-(5-(chloromethyl)thiazol-2-yl)acetamide (190 mg, 0.98 mmol), 4-benzyl-3-fluoropiperidine hydrochloride as single isomer (150 mg, 0.65 mmol), DIPEA (125 mg, 1.98 mmol) and ACN (10 mL). The crude was purified by flash column chromatography followed by MD Autoprep (Method B) to give the title compound as brown solid as single isomer. Yield: 2% (15 mg). LCMS: (Method C) 348.0 (M+H) HPLC: (Method C) RT. 2.89 min, 99.4% (Max), 98.2% (254 nm).

$^1$H NMR (400 MHz, DMSO-$d_6$): δ 11.95 (s, 1H), 7.31-7.27 (m, 2H), 7.24 (s, 1H), 7.20-7.19 (m, 3H), 4.46 (d, J=47.6 Hz, 1H), 3.63 (s, 2H), 3.06-3.03 (m, 1H), 2.81 (d, J=10.8 Hz, 1H), 2.70-2.65 (m, 1H), 2.56-2.46 (m, 2H), 2.11 (s, 3H), 1.99-1.93 (m, 1H), 1.56-1.23 (m, 3H).

EXAMPLE 10H: PREPARATION OF 4-BENZYL-3-METHYLPIPERIDINE HYDROCHLORIDE (INTERMEDIATE)

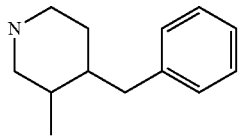

Step 1: To a stirred solution of benzyltriphenylphosphonium bromide in dry THF (20 mL), potassium tert-butoxide (2.0 g, 17.8 mmol) was added at rt and the resulting mixture was stirred for 1 h. Then tert-butyl 3-methyl-4-oxopiperidine-1-carboxylate (2.0 g, 9.3 mmol) was added at rt and the reaction mixture was stirred at rt for 3 h. The reaction mixture was concentrated. To the resulting crude mixture, water (20 mL) was added and extracted with DCM (80 mL). The organic layer was dried over $Na_2SO_4$ and concentrated. The resulting residue was purified by silicagel column chromatography to get tert-butyl 4-benzylidene-3-methylpiperidine-1-carboxylate as a pale yellow liquid. Yield: 63% (1.7 g). LCMS: (Method C) 232.0 (M-t-Bu+H), RT. 6.03 min, 95.27% (Max).

$^1$H NMR (400 MHz, DMSO-$d_6$): δ 7.34-7.29 (m, 2H), 7.21-7.17 (m, 3H), 6.32 (s, 1H), 3.37-3.31 (m, 2H), 2.38-2.25 (m, 5H), 1.45 (s, 9H), 1.08 (d, J=9.2 Hz, 3H).

Step 2: To a stirred solution of tert-butyl 4-benzylidene-3-methylpiperidine-1-carboxylate (1.7 g, 5.9 mmol) in dry MeOH (10 mL), Pd/C (0.180 g, 10%) was added. The reaction mixture was stirred under hydrogen pressure (2 kg/cm$^3$) at rt for 2 h. The reaction mixture was filtered and concentrated. The resulting crude product was used as such for next step. Tert-butyl 4-benzyl-3-methylpiperidine-1-carboxylate was isolated as brown solid. Yield: 82% (1.4 g). LCMS: (Method C) 234.0 (M-t-Bu+H), RT. 6.01 min, 60.01% (Max).

$^1$H NMR (400 MHz, DMSO-$d_6$): δ 7.28-7.23 (m, 2H), 7.18-7.12 (m, 3H), 2.97-2.93 (m, 2H), 2.48-2.47 (m, 2H), 1.88-1.83 (m, 2H), 1.40 (s, 3H), 1.34-1.32 (m, 4H), 0.9 (d, J=9.2 Hz, 3H).

Step 3: To a stirred solution of tert-butyl 4-benzyl-3-methylpiperidine-1-carboxylate (1.4 g, 4.8 mmol) in 1,4-dioxane (80 mL), HCl solution in dioxane (20 mL, 4 M) added at rt and stirred for 2 h. The reaction mixture was concentrated. The resulting crude product was washed with diethyl ether (5 mL) and was used as such in EXAMPLE 10-53 synthesis without further purification. 4-benzyl-3-methylpiperidine hydrochloride was isolated as off-white solid. Yield: 98% (0.85 g). LCMS: (Method C) 234.0 (M+H), RT. 2.85 min, 63.36% (Max).

$^1$H NMR (400 MHz, DMSO-$d_6$): δ 7.30-7.27 (m, 2H), 7.25-7.14 (m, 3H), 3.02-2.82 (m, 4H), 2.56-2.54 (m, 2H), 1.89-1.88 (m, 2H), 1.60-1.40 (m, 3H), 0.9 (d, J=9.2 Hz, 3H).

EXAMPLE 10-53: PREPARATION OF N-(5-((4-BENZYL-3-METHYLPIPERIDIN-1-YL)METHYL)THIAZOL-2-YL)ACETAMIDE

The title compound was synthesized by following general procedure C, using N-(5-(chloromethyl)thiazol-2-yl)acetamide (400 mg, 2.1 mmol), 4-benzyl-3-methylpiperidine hydrochloride (300 mg, 1.3 mmol), DIPEA (740 mg, 4.6 mmol) and ACN (20 mL). The crude was purified by flash chromatography to give the title compound as white solid. Yield: 5% (21 mg). LC/MS: (Method D) 344.0 (M+H), HPLC: (Method C) RT. 3.27 min, 98.7% (Max), 98.6% (254 nm).

$^1$H NMR (400 MHz, DMSO-$d_6$): δ 12.92 (s, 1H), 7.28-7.24 (m, 2H), 7.21 (s, 1H), 7.18-7.16 (m, 3H), 3.58 (d, J=13.6 Hz, 1H), 3.48 (d, J=14.4 Hz, 1H), 2.76-2.73 (m, 1H), 2.46-2.43 (m, 3H), 2.11 (s, 3H), 2.04-2.02 (m, 1H), 1.94-1.90 (m, 1H), 1.68 (br s, 2H), 1.42-1.37 (m, 1H), 1.31-1.28 (m, 1H), 0.95-0.94 (d, J=4.0 Hz, 3H).

EXAMPLE 10I: PREPARATION OF 4-(4-METHYLBENZYL)PIPERIDINE HYDROCHLORIDE (INTERMEDIATE)

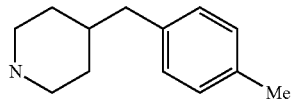 [SMILES: Cc1ccc(CC2CCNCC2)cc1]

Step 1: To 4-(bromomethyl) benzonitrile (2.0 g, 10.2 mmol), triethyl phosphite (2.3 mL, 13.4 mmol) was added at rt and refluxed at 150° C. for overnight. The reaction mixture was cooled and evaporated under vacuum. The crude product was taken for next step without further purification. Yield: 84% (3.1 g, colorless liquid).

$^1$H NMR (400 MHz, DMSO-$d_6$): δ 7.77 (d, J=10.68 Hz, 2H), 7.46 (d, J=10.68 Hz, 2H), 3.99-3.88 (m, 6H), 3.40 (s, 2H), 1.24-1.02 (m, 9H).

Step 2: To a stirred solution of (4-cyanobenzyl)triethoxyphosphonium bromide (3.1 g, 8.56 mmol), 15-crown-5 ether (0.15 g, 0.68 mmol) in dry THF (25 mL), NaH (60%, 0.31 g, 7.7 mmol) was added at 0° C. and stirred for 1 h. Then 1-boc piperidin-4-one (1.43 g, 7.1 mmol) in THF (15 mL) was added and stirred at rt for overnight. Reaction mixture was quenched with ice water extracted with ethyl acetate (80 mL). The organic layer was washed with 10% $NaHCO_3$ (10 mL), water (10 mL) and brine (10 mL). The organic layer was dried over $Na_2SO_4$ and concentrated. The crude product was purified by silica gel column chromatography to get tert-butyl 4-(4-cyanobenzylidene)piperidine-1-carboxylate as a white solid. Yield: 56% (4.3 g, white solid). LCMS: (Method C) 199.2 (M-Boc+H), RT. 5.39 min, 98.42% (Max).

¹H NMR (400 MHz, DMSO-d₆): δ 7.77 (d, J=8.0 Hz, 2H), 7.39 (d, J=12.0 Hz, 2H), 6.42 (s, 1H), 3.38-3.35 (m, 4H), 2.34-2.32 (m, 4H), 1.40 (s, 9H).

Step 3: To a stirred solution of tert-butyl 4-(4-cyanobenzylidene)piperidine-1-carboxylate (1.4 g, 4.69 mmol) in dry MeOH/THF (60 mL, 1:1), was added Pd/C (0.15 g, 10%) under nitrogen. The reaction mixture was stirred under hydrogen pressure (2 kg/cm³) at rt for 1 h. The reaction mixture was filtered through celite, concentrated to afford tert-butyl 4-(4-methylbenzyl)piperidine-1-carboxylate as a off-white solid. Yield: 78% (1.1 g). LCMS: (Method C) 190.2 (M-Boc+H), RT. 6.11 min, 75.33% (Max).

¹H NMR (400 MHz, DMSO-d₆): δ 7.35-7.30 (m, 1H), 7.04-7.03 (m, 3H), 3.86 (d, J=12.0 Hz, 2H), 2.59 (m, 2H), 2.49-2.48 (m, 3H), 2.23 (s, 3H), 1.59-1.56 (m, 3H), 1.367 (s, 9H).

Step 4: To a stirred solution of tert-butyl 4-(4-methylbenzyl)piperidine-1-carboxylate (1.1 g, 3.6 mmol) in 1,4-dioxane (6 mL), HCl solution in dioxane (10 mL, 4 M) was added at rt and stirred for 2 h. The reaction mixture was concentrated. The crude mixture was washed with diethyl ether (10 mL) affording 4-(4-methylbenzyl)piperidine as off-white solid. It was used as such in the synthesis of EXAMPLE 10-54. Yield: 88% (0.75 g). LCMS: (Method C) 190.2 (M+H), RT. 3.00 min, 86.43% (Max).

¹H NMR (400 MHz, DMSO-d₆): δ 8.56 (s, 1H), 7.06-7.04 (m, 4H), 3.20-3.16 (m, 3H), 2.76-2.72 (m, 3H), 2.24 (s, 3H), 1.72-1.63 (m, 4H), 1.35-1.32 (m, 2H).

EXAMPLE 10-54: PREPARATION OF N-(5-((4-(4-METHYLBENZYL)PIPERIDIN-1-YL)METHYL)THIAZOL-2-YL)ACETAMIDE

The title compound was synthesized by following general procedure C, using N-(5-(chloromethyl)thiazol-2-yl)acetamide (290 mg, 1.53 mmol), 4-(4-methylbenzyl)piperidine hydrochloride (300 mg, 1.27 mmol), DIPEA (518 mg, 3.82 mmol) and ACN (10 mL). The crude was purified by flash chromatography to give the title compound as off white solid. Yield: 3% (14 mg). LC/MS: (Method C) 344.2 (M+H), HPLC: (Method C) RT. 3.33 min, 97.1% (Max), 95.7% (254 nm).

¹H NMR (400 MHz, DMSO-d₆): δ 11.92 (s, 1H), 7.21 (s, 1H), 7.06 (d, J=7.6 Hz, 2H), 7.02 (d, J=7.6 Hz, 2H), 3.56 (s, 2H), 2.80-2.78 (m, 2H), 2.44 (d, J=6.4 Hz, 2H), 2.25 (s, 3H), 2.11 (s, 3H), 1.87-1.82 (m, 2H), 1.52-1.42 (m, 3H), 1.19-1.11 (m, 2H).

EXAMPLE 10K: 4-(NAPHTHALEN-2-YLMETHYL)PIPERIDINE HYDROCHLORIDE (INTERMEDIATE)

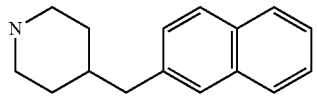 [SMILES: c1ccc2cc(CC3CCNCC3)ccc2c1]

Step 1: To a stirred solution of 2-bromomethylnapthalene (2.5 g, 11.3 mol, Spectrochem) in dry Toluene (25 mL), was added triphenylphosphine (2.66 g, 10.1 mmol, Spectrochem) at rt and refluxed for 16 h. The reaction mixture was cooled to rt, and evaporated under vacuum. The crude product was washed with diethyl ether and dried under vacuum. The crude product was isolated as white solid. It was taken for next step without further purification. Yield: 70% (5 g). LCMS: (Method C) 403.2 (M-Br), RT. 4.66 min, 99.07% (Max).

¹H NMR (400 MHz, DMSO-d₆): δ 7.91-7.89 (m, 4H), 7.88-7.75 (m, 13H), 7.73-7.68 (m, 4H), 7.07-7.05 (m, 1H), 5.37-5.34 (m, 2H).

Step 2: To a stirred solution of napthyltriphenylphosphonium bromide (4.8 g, 10.0 mmol) in dry THF (10 mL), was added potassium tert-butoxide (1.0 g, 10.0 mmol) at rt and the mixture was stirred for 1 h. Then 1-boc piperdin-4-one (1.0 g, 5.02 mmol, GLR scientific) was added and the reaction mixture was stirred for 3 h. It was concentrated. Water (20 mL) was added and was extracted with DCM (50 mL). The organic layer was dried over Na₂SO₄ and concentrated. The crude product was purified by silica gel column chromatography (3% EtOAc in hexane) to get tert-butyl 4-(naphthalen-2-ylmethylene) piperidine-1-carboxylate as a white solid. Yield: 56% (0.91 g). LCMS: (Method C) 268 (M-t-Bu+H), RT. 6.18 min, 95.39% (Max).

¹H NMR (400 MHz, DMSO-d₆): δ 7.84 (t, J=7.8 Hz, 3H), 7.72 (s, 1H), 7.50-7.39 (m, 2H), 7.38-7.35 (m, 1H), 6.51 (m, 1H), 3.45-3.31 (m, 4H), 2.34-2.25 (m, 4H), 1.40 (s, 9H).

Step 3: To a stirred solution of tert-butyl 4-(naphthalen-2-ylmethylene) piperidine-1-carboxylate (0.91 g, 2.8 mmol) in dry MeOH (10 mL), was added Pd/C (0.09 g, 10%, Aldrich) under nitrogen. The reaction mixture was stirred under hydrogen pressure (2 kg/cm³) at rt for 2 h. The reaction mixture was concentrated and dried under vacuum. The crude product was isolated as white solid. It was used in the next step without any further purification. Yield: 55% (0.55 g). LCMS: (Method C) 270.0 (M-t-Bu+H), RT. 6.22 min, 95.4% (Max).

¹H NMR (400 MHz, DMSO-d₆): δ 7.87-7.82 (m, 2H), 7.67 (s, 1H), 7.50-7.43 (m, 2H), 7.43-7.37 (m, 1H), 3.91 (s, 2H), 2.67-2.51-1.57 (m, 3H), 1.58-1.55 (m, 2H), 1.38 (s, 9H), 1.11-1.03 (m, 2H).

Step 4: To a stirred solution of tert-butyl 4-(naphthalen-2-ylmethyl) piperidine-1-carboxylate (0.55 g, 1.6 mmol) in 1,4-dioxane (10 mL), HCl solution in dioxane (20 mL, 4 M) added at rt and the mixture was stirred for 2 h. It was concentrated. The crude product was washed with diethyl ether (5 mL) and was isolated as an off white solid. Crude 4-(naphthalen-2-ylmethyl)piperidine hydrochloride was used in the synthesis of EXAMPLE 10-56 without any further purification. Yield: 90% (0.5 g).

¹H NMR (400 MHz, DMSO-d₆): δ 8.74 (s, 1H), 8.48 (s, 1H), 7.83 (d, J=9.0 Hz, 3H), 7.45 (s, 1H), 7.35 (d, J=11.2 Hz, 1H), 7.02-6.82 (m, 1H), 3.22-3.18 (m, 3H), 2.83-2.67 (m, 4H), 1.86 (s, 1H), 1.73-1.68 (m, 2H), 1.42-1.25 (m, 2H).

EXAMPLE 10-56: PREPARATION OF N-(5-((4-(NAPHTHALEN-2-YLMETHYL)PIPERIDIN-1-YL)METHYL)THIAZOL-2-YL)ACETAMIDE

The title compound was synthesized by following general procedure C, using N-(5-(chloromethyl)thiazol-2-yl)acetamide (180 mg, 0.95 mmol), 4-(naphthalen-2-ylmethyl) piperidine hydrochloride (250 mg, 0.95 mmol), DIPEA (365 mg, 2.8 mmol) and DMF (10 mL). The crude was purified by MD autoprep (Method B) to give the title compound as brown solid. Yield: 5% (12 mg). LC/MS: (Method C) 380.2 (M+H), HPLC: (Method C) RT. 3.64 min, 97.9% (Max), 98.5% (254 nm).

¹H NMR (400 MHz, DMSO-d₆): δ 11.90 (s, 1H), 7.86-7.81 (m, 3H), 7.65 (s, 1H), 7.48-7.41 (m, 2H), 7.34 (dd, J=2.8, 8.4 Hz, 1H), 7.21 (s, 1H), 3.57 (s, 2H), 2.82-2.79 (m,

2H), 2.67-2.66 (m, 2H), 2.11 (s, 3H), 1.90-1.84 (m, 2H), 1.57-1.55 (m, 3H), 1.28-1.22 (m, 2H).

EXAMPLE 10L: PREPARATION OF 6-(PIPERIDIN-4-YLMETHYL)QUINOXALINE HYDROCHLORIDE (INTERMEDIATE)

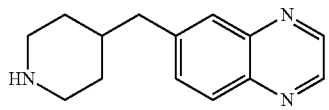 [SMILES: c1cnc2cc(CC3CCNCC3)ccc2n1]

Step 1: To a stirred solution of methyl triphenyl phosphonium bromide (14.3 g, 40.02 mmol) in dry THF (40 mL) under nitrogen, n-BuLi (12.0 mL, 30.15 mmol) was added at −78° C. drop wise and the mixture was stirred for 1 h at the same temperature. Then 1-boc piperdin-4-one (4.0 g, 20.1 mmol) in THF (20 mL) was added and the mixture was stirred at rt for 1 h. The reaction mixture was cooled to 0° C. and quenched with sat. NH$_4$Cl. Product was extracted with ethyl acetate (100 mL). Organic layer was washed with brine (50 mL), was dried over anhydrous sodium sulfate and concentrated. The resulting crude product was purified by column chromatography to afford tert-butyl 4-methylenepiperidine-1-carboxylate as a colorless liquid. Yield: 67% (2.6 g). LCMS: (Method C) 98.2 (M-Boc+H), RT. 4.83 min, 93.41% (Max).

$^1$H NMR (400 MHz, DMSO-d$_6$): δ 4.73 (s, 2H), 3.30 (t, J=12.0 Hz, 4H), 2.08 (t, J=12.0 Hz, 4H), 1.38 (s, 9H).

Step 2: To a degassed sample of tert-butyl 4-methylenepiperidine-1-carboxylate (0.6 g, 3.04 mmol) in dry THF (10 mL) was added 9-BBN (6.1 mL, 3.04 mmol). The resulting mixture was refluxed for 1 h. After cooling to rt, 6-bromo quinoxaline (0.55 g, 2.78 mmol), Pd(dppf)Cl$_2$.CH$_2$Cl$_2$ (0.15 g, 0.18 mmol), DMF (10 mL), water (1 mL) and K$_2$CO$_3$ (0.6 g, 4.5 mmol) were added at rt. The resulting mixture was heated at 60° C. for 3 h. The reaction mixture was then cooled to rt, diluted with water (20 mL). The pH was adjusted to 11 with 10% aqueous NaOH and the mixture was extracted with ethyl acetate. The organic layer was dried over anhydrous Na$_2$SO$_4$ and concentrated to get the crude product as colorless liquid. Tert-butyl 4-(quinoxalin-6-ylmethyl)piperidine-1-carboxylate was used in the next step without further purification. Yield: 24% (0.23 g).

$^1$H NMR (400 MHz, DMSO-d$_6$): δ 8.89-8.86 (m, 2H), 8.04-8.01 (m, 3H), 2.73-2.67 (m, 2H), 2.25 (m, 9H), 1.13 (s, 9H).

Step 3: To a stirred solution of tert-butyl 4-(quinoxalin-6-ylmethyl)piperidine-1-carboxylate (0.3 g, 0.7 mmol) in 1,4-dioxane (5 mL), HCl solution in dioxane (10 mL, 4 M) added at rt and the resulting mixture was stirred for 2 h. The reaction mixture was concentrated. The resulting crude product was washed with diethyl ether (5 mL), affording 6-(piperidin-4-ylmethyl)quinoxaline hydrochloride as grey solid. It was used in the synthesis of EXAMPLE 10-63 without any further purification. Yield: 77% (0.2 g). LCMS: (Method C) 228.2 (M+H), RT. 1 min, 96.98% (Max).

$^1$H NMR (400 MHz, DMSO-d$_6$): δ 8.90 (d, J=12.0 Hz, 2H), 8.02-7.90 (m, 3H), 3.24-3.20 (m, 2H), 2.82-2.80 (m, 4H), 2.25 (m, 4H).

EXAMPLE 10-63: PREPARATION OF N-(5-((4-(QUINOXALIN-6-YLMETHYL)PIPERIDIN-1-YL)METHYL)THIAZOL-2-YL)ACETAMIDE

The title compound was synthesized by following general procedure C, using 6-(piperidin-4-ylmethyl)quinoxaline hydrochloride (0.1 g, 0.38 mmol), (10 mL), DIPEA (0.3 mL, 1.14 mmol), N-(5-(chloromethyl)thiazol-2-yl)acetamide (0.11 g, 0.57 mmol) in dry acetonitrile. The crude product was purified by flash column chromatography to afford the title compound as a brown solid. Yield: 16.8% (75 mg). LCMS: (Method C) 382.2 (M+H). HPLC: (Method C) RT. 2.21 min, 99.69% (Max), 99.01% (254 nm).

$^1$H NMR (400 MHz, DMSO-d$_6$): δ 11.98 (s, 1H), 8.02 (d, J=8.0 Hz, 2H), 7.88 (s, 1H), 7.72 (d, J=8.0 Hz, 1H), 7.23 (s, 1H), 3.58 (br.s, 2H), 2.79 (d, J=5.6 Hz, 3H), 2.12 (s, 3H), 2.09 (s, 1H), 1.99-1.88 (m, 2H), 1.58 (m, 3H), 1.26-1.23 (m, 2H).

EXAMPLE 10M: PREPARATION OF 4-(3,5-DIFLUOROBENZYL) PIPERIDINE HYDROCHLORIDE (INTERMEDIATE)

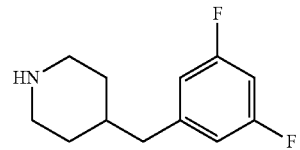 [SMILES: Fc1cc(F)cc(CC2CCNCC2)c1]

Step 1: To 3,5-difluoro benzyl bromide (3 g, 14.4 mmol), triethyl phosphite (3.4 mL, 19.1 mmol) was added at rt and refluxed at 150° C. overnight. The reaction mixture was cooled and evaporated under vacuum. The crude product was isolated as colorless liquid and was taken for next step without further purification. Yield: 95% (5.2 g).

$^1$H NMR (400 MHz, DMSO-d$_6$): δ 7.14-7.07 (m, 1H), 7.00-6.98 (m, 2H), 4.03-3.90 (m, 6H), 3.34-3.14 (m, 2H), 1.26-1.22 (m, 9H).

Step 2: To a stirred solution of (3,5-difluorobenzyl)triethoxyphosphonium bromide (5.2 g, 13.9 mmol) 15-crown-5 ether (0.24 mL, 1.1 mmol) in dry THF (35 mL), NaH (60%, 0.5 g, 12.5 mmol) was added at 0° C. and stirred for 1 h. Then 1-boc piperdin-4-one (2.3 g, 11.7 mmol) in THF (25 mL) was added and stirred at rt overnight. Reaction mixture was quenched with ice water and extracted with ethyl acetate (100 mL) and washed with 10% NaHCO$_3$, water and brine. The organic layer was dried over Na$_2$SO$_4$ and concentrated. The crude product was purified by silica gel column chromatography to get tert-butyl 4-(3,5-difluorobenzylidene)piperidine-1-carboxylate as a colorless liquid. Yield: 57% (2 g). LCMS: (Method C) 254.0 (M-t-Bu+H), RT. 5.65 min, 99.6% (Max).

$^1$H NMR (400 MHz, DMSO-d$_6$): δ 7.11-7.06 (m, 1H), 6.94 (d, J=6.8 Hz, 1H), 6.35 (s, 1H), 3.42-3.32 (m, 4H), 2.40 (t, J=3.4 Hz, 2H), 2.39 (t, J=5.6 Hz, 2H), 1.41 (s, 9H).

Step 3: To a stirred solution of tert-butyl 4-(3,5-difluorobenzylidene)piperidine-1-carboxylate (2 g, 6.4 mmol) in dry MeOH (80 mL), Pd/C (0.20 g, 10%) was added under nitrogen. The reaction mixture was stirred under hydrogen pressure (2 kg/cm$^3$) at rt for 2 h. It was then filtered through celite, concentrated and used as such for next step. Yield: 95% (0.9 g, white solid). LCMS: (Method C) 256.0 (M-t-Bu+H), RT. 5.60 min, 99.73% (Max).

$^1$H NMR (400 MHz, DMSO-d$_6$): δ 7.04-6.98 (m, 1H), 6.94-6.91 (m, 2H), 3.89 (d, J=10.6 Hz, 2H). 2.65 (t, J=1.8 Hz, 2H). 2.50 (d, J=5.3 Hz, 2H), 1.72-1.65 (m, 1H), 1.51-1.47 (m, 2H), 1.36 (s, 9H), 1.05-0.95 (m, 2H).

Step 4: To a stirred solution of tert-butyl 4-(3,5-difluorobenzyl)piperidine-1-carboxylate (1.9 g, 6.1 mmol) in 1,4-dioxane (6 mL), HCl solution in dioxane (20 mL, 4 M) was added at rt and stirred for 2 h. The reaction mixture was concentrated. The resulting crude product was washed with diethyl ether (5 mL), affording 4-(3,5-difluorobenzyl) piperidine hydrochloride as off-white solid. It was used in the synthesis of EXAMPLE 10-64 without any further purification. Yield: 93% (1.4 g). LCMS: (Method C) 212.0 (M+H), RT. 2.84 min, 99.69% (Max).

EXAMPLE 10-64: PREPARATION OF N-(5-((4-(3,5-DIFLUOROBENZYL)PIPERIDIN-1-YL)METHYL)THIAZOL-2-YL)ACETAMIDE

The title compound was synthesized by following general procedure C, using N-(5-(chloromethyl)thiazol-2-yl)acetamide (0.35 g, 1.82 mmol), 4-(3,5-difluorobenzyl) piperidine hydrochloride (0.3 g, 1.21 mmol), DIPEA (0.7 mL, 3.6 mmol) in dry ACN (20 mL). The crude was purified by flash column chromatography to afford the title compound as a brown solid. Yield: 16.8% (75 mg). LCMS: (Method C) 366.0 (M+H). HPLC: (Method C) RT 3.27 min, 98.9% (Max), 96.7% (254 nm).
$^1$H NMR (400 MHz, DMSO-d$_6$): δ 11.93 (s, 1H), 7.21 (s, 1H), 7.03-6.98 (m, 1H), 6.91 (d, J=6.4 Hz, 2H), 3.57 (s, 2H), 2.81-2.78 (m, 2H), 2.53 (s, 2H), 2.11 (s, 3H), 1.89-1.84 (m, 2H), 1.51-1.48 (m, 3H), 1.23-1.13 (m, 2H).

EXAMPLE 10N: PREPARATION OF 4-(NAPHTHALEN-1-YLMETHYL) PIPERIDINE HYDROCHLORIDE (INTERMEDIATE)

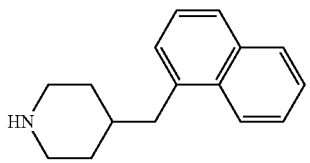

Step 1: To a stirred solution of 1-bromomethylnapthalene (1.97 g, 8.9 mol, Combiblocks) in dry toluene (25 mL), triphenyl phosphine (2.1 g, 8.02 mmol, Spectrochem) was added at rt and refluxed for 16 h. Then the reaction mixture was cooled to rt and evaporated under vacuum. The resulting crude product was washed with diethyl ether and used as such for next step without further purification. Yield: 87% (3.5 g, white solid). LCMS: (Method A) 403.2 (M-Br), RT. 4.43 min, 97.5% (Max).

Step 2: To a stirred solution of (naphthalen-1-ylmethyl) triphenylphosphonium bromide (3.5 g, 7.24 mmol) in dry THF (10 mL), potassium tert-butoxide (0.813 g, 7.24 mmol) was added at rt and stirred for 1 h. Then 1-boc-piperdin-4-one (0.722 g, 3.62 mmol, GLR scientific) was added at the same temperature and stirred for another 3 h. The reaction mixture was quenched with water (20 mL) and extracted with DCM (50 mL). The organic layer was dried over Na$_2$SO$_4$ and concentrated. The resulting crude product was purified by silica gel column chromatography (3% EtOAc in hexane) to get tert-butyl 4-(naphthalen-1-ylmethylene) piperidine-1-carboxylate as off-white solid. Yield: 34% (0.4 g). LCMS: (Method A) 268.1 (M-t-Bu+H), RT. 5.85 min, 45.9% (Max).

Step 3: To a stirred solution of tert-butyl 4-(naphthalen-1-ylmethylene) piperidine-1-carboxylate (0.4 g, 1.23 mmol) in dry MeOH (20 mL), Pd/C (0.04 g, 10%, Aldrich) was added under nitrogen. The reaction mixture was stirred under hydrogen pressure (2 kg/cm$^3$) at rt for 2 h. The reaction mixture was filtered through celite and concentrated vacuum. The resulting crude product as such was taken for the next step without further purification. Yield: 87% (0.35 g, colorless liquid). LCMS: (Method A) 270.0 (M-t-Bu+H), RT. 5.78 min, 58.0% (Max).

Step 4: To a stirred solution of tert-butyl 4-(naphthalen-1-ylmethyl) piperidine-1-carboxylate (0.35 g, 1.07 mmol) in 1,4-dioxane (10 mL), HCl dioxane (10 mL, 4M) was added at rt and stirred for 2 h. The reaction mixture was concentrated under vacuum. To resulting crude product was co-distilled with diethyl ether (5 mL) and used as such for the next step. Yield: 89% (0.25 g, white solid).LCMS: (Method A) 226.2 (M+H), RT. 3.22 min, 88.8% (Max).

EXAMPLE 10-65: PREPARATION OF N-(2-((4-(NAPHTHALEN-1-YLMETHYL)PIPERIDIN-1-YL)METHYL)THIAZOL-5-YL)ACETAMIDE

The title compound was synthesized by following general procedure C, using N-(5-(chloromethyl)thiazol-2-yl)acetamide (79 mg, 0.42 mmol), 4-(naphthalen-1-ylmethyl) piperidine hydrochloride (110 mg, 0.42 mmol), DIPEA (0.163 mg, 1.26 mmol) and ACN (5 mL). The crude was purified by MD-Auto prep. Method B as off-white solid. Yield: 2.1% (5.7 mg). LCMS: (Method A) 380.0 (M+H), RT. 3.62 min, 98.8% (Max), 98.3 (220 nm). HPLC: (Method A) RT. 3.58 min, 99.22% (Max), 99.18% (220 nm).
$^1$H NMR (400 MHz, DMSO-d$_6$): δ 12.6 (s, 1H), 7.92-7.86 (m, 2H), 7.74 (d, J=3.6 Hz, 2H), 7.53-7.49 (m, 2H), 7.40 (t, J=7.2 Hz, 1H), 4.33 (s, 2H), 3.51-3.46 (m, 2H), 3.10-3.03 (m, 1H), 2.70-2.56 (m, 2H), 2.34-2.32 (m, 2H), 2.19-2.16 (m, 2H), 1.89-1.85 (m, 2H), 1.59-1.50 (m, 2H), 1.26-1.20 (m, 2H).

EXAMPLE 11A: PREPARATION OF 1-(1-(BENZO[D][1,3]DIOXOL-5-YL)ETHYL)PIPERAZINE HYDROCHLORIDE (INTERMEDIATE)

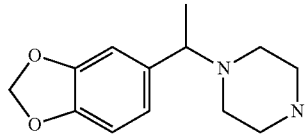 [SMILES: CC(c1ccc2c(c1)OCO2)N1CCNCC1]

Step 1: To a stirred solution of 3,4-methylenedioxy acetophenone (10.0 g, 60.91 mmol, Alfa aesar) in dry MeOH (200 mL), NaBH$_4$ (2.7 g, 71.3 mmol, Loba chemie) was added slowly at 0° C. The reaction mixture was stirred at room temperature for 1 h. Then the reaction mixture was concentrated under vacuum and diluted with DCM. The DCM layer was washed with water, brine and, dried over anhydrous Na$_2$SO$_4$. The solvent was removed under reduced pressure and resulting crude alcohol was used as such in the next step. Yield: 99% (10.0 g, colorless liquid). LCMS: (Method D) 149.0 (M–H$_2$O+H), RT. 2.513 min, 98.6% (Max), 97.7% (254 nm).
$^1$H NMR (400 MHz, CDCl$_3$): δ 6.89 (s, 1H), 6.89-6.75 (m, 2H), 5.95 (s, 2H), 4.81 (t, J=8.0 Hz, 1H), 1.46 (d, J=8.0 Hz, 3H).

Step 2: To a stirred solution of 1-(benzo[d][1,3]dioxol-5-yl)ethan-1-ol (10.0, 60.2 mmol) in dry DCM (27 mL), thionyl chloride (23.4 g, 180.72 mmol) was added slowly at 0° C. and the resulting mixture was refluxed for 3 h. It was then concentrated under reduced pressure. The resulting residue was co-distilled with DCM to give 5-(1-chloroethyl)benzo[d][1,3]dioxole as a brown liquid. Yield: 72% (6.3 g). LCMS: (Method D) 149.0 (M−HCl+H), RT. 3.705 min, 80.15% (Max).

$^1$H NMR (400 MHz, DMSO-$d_6$): δ 7.06 (d, J=4.0 Hz, 1H), 6.93 (d, J=8.0 Hz, 1H), 6.86 (d, J=8.0 Hz, 1H), 6.01 (s, 2H), 2.49 (q, J=8.9 Hz, 1H), 1.74 (d, J=8.9 Hz, 3H).

Step 3: To a stirred solution of 1-Boc-piperazine (6.5 g, 34.0 mmol) in dry ACN (100 mL), 5-(1-chloroethyl)benzo[d][1,3]dioxole (6.39, 34.7 mmol) and DIPEA (13.45 g, 104.0 mmol) was added at rt and was heated at 80° C. overnight. The reaction mixture was concentrated under vacuum and the resulting residue was diluted with EtOAc. The organic layer was washed with water, brine solution, dried over anhydrous Na$_2$SO$_4$ and concentrated under vacuum. The crude product was purified by silicagel column chromatography to afford tert-butyl 4-(1-(benzo[d][1,3]dioxol-5-yl)ethyl)piperazine-1-carboxylate as a colorless gummy liquid. Yield: 20% (2.0 g). LCMS: (Method C) 335.2 (M+H), RT. 3.10 min, 93.15% (Max), 96.06% (254 nm).

$^1$H NMR (400 MHz, DMSO-$d_6$): δ 6.85-6.82 (m, 2H), 6.74-6.71 (m, 1H), 5.98 (d, J=1.6 Hz, 2H), 3.37-3.36 (m, 1H), 3.27 (m, 4H), 2.28-2.21 (m, 4H), 1.37 (s, 9H), 1.25 (d, J=6.8 Hz, 3H).

Step 4: To a stirred solution of tert-butyl 4-(1-(benzo[d][1,3]dioxol-5-yl)ethyl)piperazine-1-carboxylate (2.0 g, 5.9 mmol) in dry dioxane (10 mL), HCl solution in dioxane (20 mL, 4 M) was added and the reaction mixture was stirred at rt for 2 h. The reaction mixture was concentrated under vacuum and the crude was purified by recrystallization with diethyl ether to afford 1-(1-(benzo[d][1,3]dioxol-5-yl)ethyl)piperazine hydrochloride as a off-white solid. Yield: 82% (1.2 g). LCMS: (Method D) 235.0 (M+H), RT. 4.2 min, 98.56% (Max), 97.3% (220 nm).

$^1$H NMR (400 MHz, DMSO-$d_6$): δ 12.09 (m, 1H), 9.43 (m, 1H), 9.20 (m, 1H), 7.30 (s, 1H), 7.07-7.02 (m, 2H), 6.08 (s, 2H), 4.55 (m, 1H), 3.82 (m, 1H), 3.50-3.39 (m, 3H), 3.17-2.96 (m, 2H), 1.68 (s, 3H).

EXAMPLE 11-58: PREPARATION OF N-(5-((4-(1-(BENZO[D][1,3]DIOXOL-5-YL)ETHYL)PIPERAZIN-1-YL)METHYL)THIAZOL-2-YL)ACETAMIDE

The title compound was synthesized by following general procedure C, using N-(5-(chloromethyl)thiazol-2-yl)acetamide (0.28 g, 1.48 mmol), 1-(1-(benzo[d][1,3]dioxol-5-yl)ethyl)piperazine hydrochloride (0.4 g, 1.48 mmol), DIPEA (0.57 g, 4.44 mmol) and ACN (5 mL). The crude was purified by flash column chromatography to give the title compound as brown solid. Yield: 2% (3.71 mg). LC/MS: (Method C) 389.0 (M+H), HPLC: (Method C) RT. 2.09 min, 92.6% (Max), 91.1% (254 nm).

$^1$H NMR (400 MHz, DMSO-$d_6$): δ 11.94 (s, 1H), 6.83-6.81 (m, 3H), 6.71 (d, J=8.4 Hz, 1H), 5.98 (s, 2H), 3.58 (s, 2H), 3.35-34 (m, 1H), 2.33-2.32 (m, 7H), 2.10 (s, 3H), 1.23 (d, J=2.8 Hz, 3H).

EXAMPLE 11-57 AND 11-60: PREPARATION OF (S)—N-(5-((4-(1-(BENZO[D][1,3]DIOXOL-5-YL)ETHYL)PIPERAZIN-1-YL)METHYL)THIAZOL-2-YL)ACETAMIDE AND (R)—N-(5-((4-(1-(BENZO[D][1,3]DIOXOL-5-YL)ETHYL)PIPERAZIN-1-YL)METHYL)THIAZOL-2-YL)ACETAMIDE

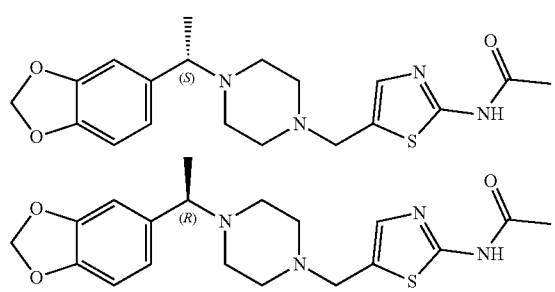

Two enantiomers of EXAMPLE 58 were separated by chiral HPLC (Chiralcell OJ-H column (250×4.6 mm, 5 μm); eluted with 0.1% DEA in hexane:IPA 90:10; flow rate 1.0 mL/min). The first eluting compound was concentrated to give EXAMPLE 60 as white solid. Yield: 3% (16 mg). LC/MS: (Method C) 389.0 (M+H), HPLC: (Method C) RT. 2.12 min, 98.9% (Max), 99.2% (254 nm). HPLC chiral purity: (Method C) RT. 16.97 min, 100.0% (Max).

$^1$H NMR (400 MHz, DMSO-$d_6$): δ 11.95 (s, 1H), 7.23 (s, 1H), 6.83 (s, 1H), (d, J=8.4 Hz, 1H), 6.71 (d, J=8.0 Hz, 1H), 5.97 (d, J=1.2 Hz, 2H), 3.57 (s, 2H), 3.31-3.28 (m, 1H), 2.33-2.32 (m, 8H), 2.10 (s, 3H), 1.22 (d, J=8.0 Hz, 3H).

The second eluting compound was concentrated to give EXAMPLE 57 as white solid. Yield: 2% (13 mg). LC/MS: (Method C) 389.0 (M+H). HPLC: (Method C) RT. 2.12 min, 99.7% (Max), 99.7% (254 nm). HPLC chiral purity: (Method C) RT. 29.60 min, 100.0% (Max).

$^1$H NMR (400 MHz, DMSO-$d_6$): δ 11.91 (s, 1H), 7.21 (s, 1H), 6.81 (s, 1H), (d, J=8.4 Hz, 1H), 6.70 (d, J=8.0 Hz, 1H), 5.96 (d, J=1.2 Hz, 2H), 3.56 (s, 2H), 3.30-3.29 (m, 1H), 2.32-2.31 (m, 8H), 2.09 (s, 3H), 1.22 (d, J=8.0 Hz, 3H).

The hOGA enzyme inhibition (IC50) of both title compounds was between 1 and 10 μM ("++").

EXAMPLE 12: HUMAN O-GLCNACASE ENZYME INHIBITION ASSAY

A TTP LabTech Mosquito liquid handler instrument pipetted 100 nL of the appropriate concentration of a solution of inhibitor in 100% DMSO (for a dose response curve calculation) into each well of a 384-well plate (Aurora Biotechnologies, Part #30311). The following reaction components were added to a final volume of 10 μL in McIlvaine's Buffer (pH 6.5): 20 nM His-Tagged hOGA and 10 μM Fluorescein mono-beta-D-(2-deoxy-2-N-acetyl) glucopyranoside (FL-GlcNAc; Marker Gene Technologies Inc, Part # M1485). The plate was incubated for 60 min at room temperature and then the reaction was terminated by the addition of 10 μL of stop buffer (200 mM glycine, pH 10.75). The plate was read on an Envision platform in a fluorescent format using the top mirror with 485 nm+dampener as the excitation filter setting and 520 nm as the emission filter setting. The amount of fluorescence measured was plotted against the concentration of inhibitor to produce a sigmoidal dose response curve, from which an $IC_{50}$ was calculated.

EXAMPLE 13: CELLULAR O-GLCNACYLATION ASSAY

B35 rat neuroblastoma cells (ATCC; CRL-2754) were plated in 96 well poly-D-lysine treated plates (BD Falcon; 354640) at a density of 10,000 cells per well in a total volume of 90 μl complete medium. The following day cells were treated with appropriate concentration of a solution of inhibitor for 16 h at 37° C. in 5% $CO_2$. Cells were fixed in 100 μl 4% paraformaldehyde for 15 min at room temperature, followed by three washes in PBS buffer. The cells were then permeabilized with 0.1% Triton X-100 for 60 min at room temperature. After three washes in PBS the cells were blocked with 10% goat serum containing 1% BSA in PBS buffer for two hours at room temperature. The cells were then incubated with a monoclonal rabbit antibody specific for tau O-GlcNAcylated at serine 400 (Epitomics) at a 1:1000 dilution overnight at 4° C. The primary antibody was washed off and the cells were incubated with a goat anti-rabbit AlexaFluor488-conjugated secondary antibody (Molecular Probes; A11034), and Hoechst 33342 nuclear dye at a concentration of 1 μg/ml were added. Cells were read on the Acumen Explorer eX3 plate reader. To calculate an $EC_{50}$ the total peak intensity was plotted against the concentration of inhibitor to produce a sigmoidal dose response curve.

EXAMPLE 14: PHARMACEUTICAL PREPARATIONS (A) Injection vials: A solution of 100 g of an active ingredient according to the invention and 5 g of disodium hydrogen phosphate in 3 l of bi-distilled water was adjusted to pH 6.5 using 2 N hydrochloric acid, sterile filtered, transferred into injection vials, lyophilized and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bi-distilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated tablets: Tablets were pressed analogously to EXAMPLE E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bi-distilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

EXAMPLE 15: INCREASED O-GLCNACYLATION REDUCES PATHOLOGICAL TAU WITHOUT AFFECTING ITS NORMAL PHOSPHORYLATION IN A MOUSE MODEL OF TAUOPATHY

Figures

FIG. 1: Effects of acute or subchronic ThiametG on O-GlcNAcylation and phosphorylation in Tg4510 mice. A, Total O-GlcNAcylation levels were increased in mouse hemi forebrain 4 h after a single administration of ThiametG or 4 h after 14 daily repeated treatments with ThiametG. B, Immunoprecipitated tau (HT7 antibody) was strongly O-GlcNAcylated at S400 in animals treated for 14 days as compared to vehicle controls. C, Tau O-GlcNAcylation protein levels were slightly increased in mouse hemi forebrain 4 h after a single treatment of ThiametG (%) and significantly increased 4 h after the last of 14 daily treatments with ThiametG. D, Tau phosphorylation was decreased at epitopes S202/205, S262, and S396 4 hrs after single administration of ThiametG, but returned to normal levels following 14 daily treatments with ThiametG. Tau phosphorylation at S356 was significantly reduced following a single and repeated (14 day) administration of ThiametG (1 way ANOVA *p<0.05). Western blot data (N=13-15/group) are expressed as mean±s.e.m. percentage of vehicle-treated controls. 1 way ANOVA; *P<0.05 as compared to control.

Figure 2:
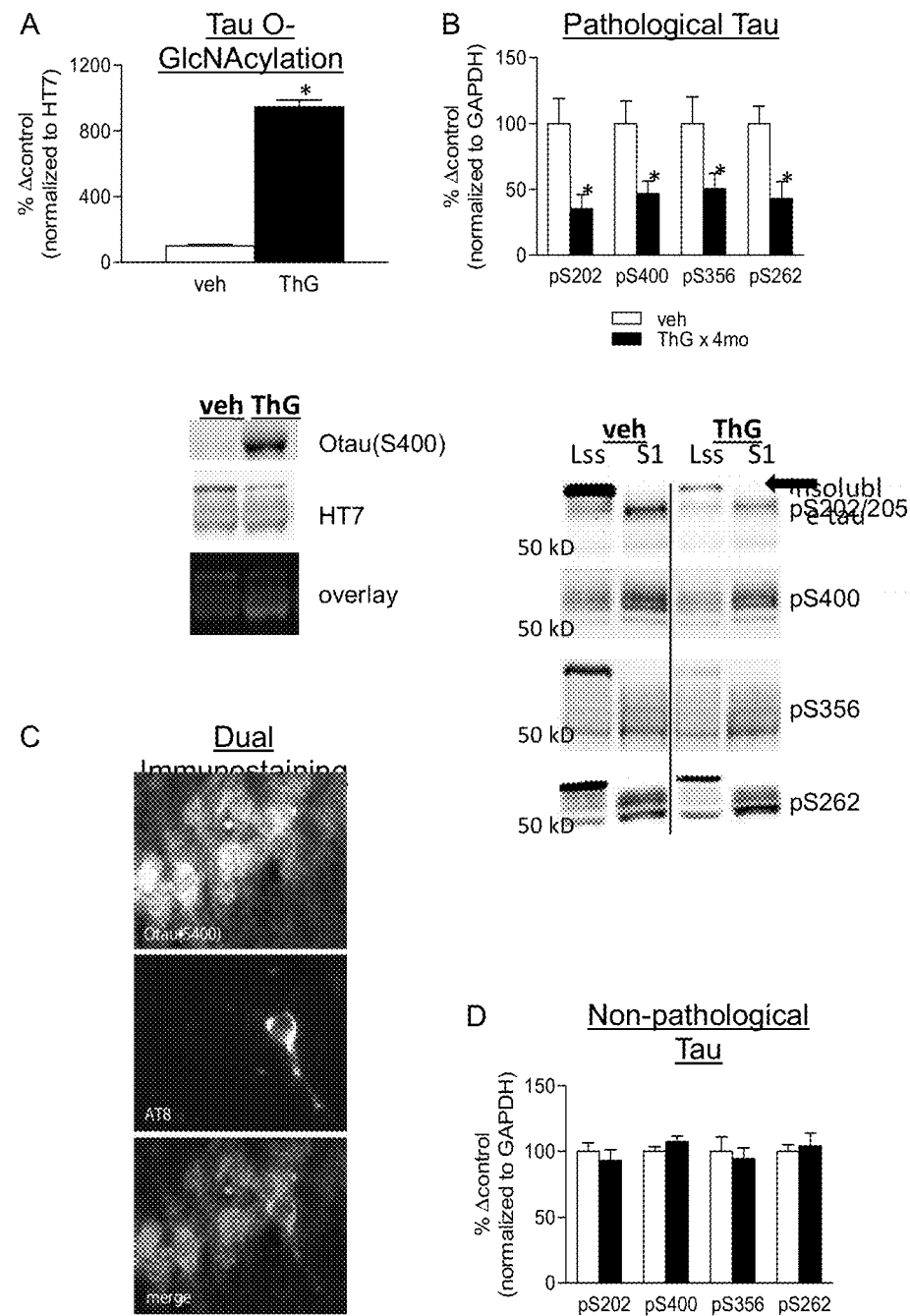

FIG. 2: Effects of chronic ThiametG treatment on tau O-GlcNAcylaton and pathological tau in Tg4510 mice. A, Tau O-GlcNAcylation levels remain elevated in mouse hemi forebrain following 4 months administration of ThiametG. B, Hyperphosphorylated pathological tau (64 kD) is dramatically reduced at epitopes pS202/205, pS400, pS356, and pS262 following 4 months administration of ThiametG. C, Localized expression of O-GlcNAc tau (Otau(S400) antibody; top panel) and AT8 (middle panel), which recognizes hyperphosphorylated aggregated tau was detected in the CA1 region of the hippocampus in Tg4510 mice. Dual-immunostaining was performed to demonstrate no colocalization of O-GlcNAc tau with pathological tau (bottom panel, 63× image). D, Tau phosphorylation status of the 50-60 kD tau species was unchanged following 4 months repeated administration with ThiametG. Western blot data (N=13-15/group) are expressed as mean±s.e.m. percentage of vehicle-treated controls. 1 way ANOVA; *P<0.05 as compared to control.

Figure 3:
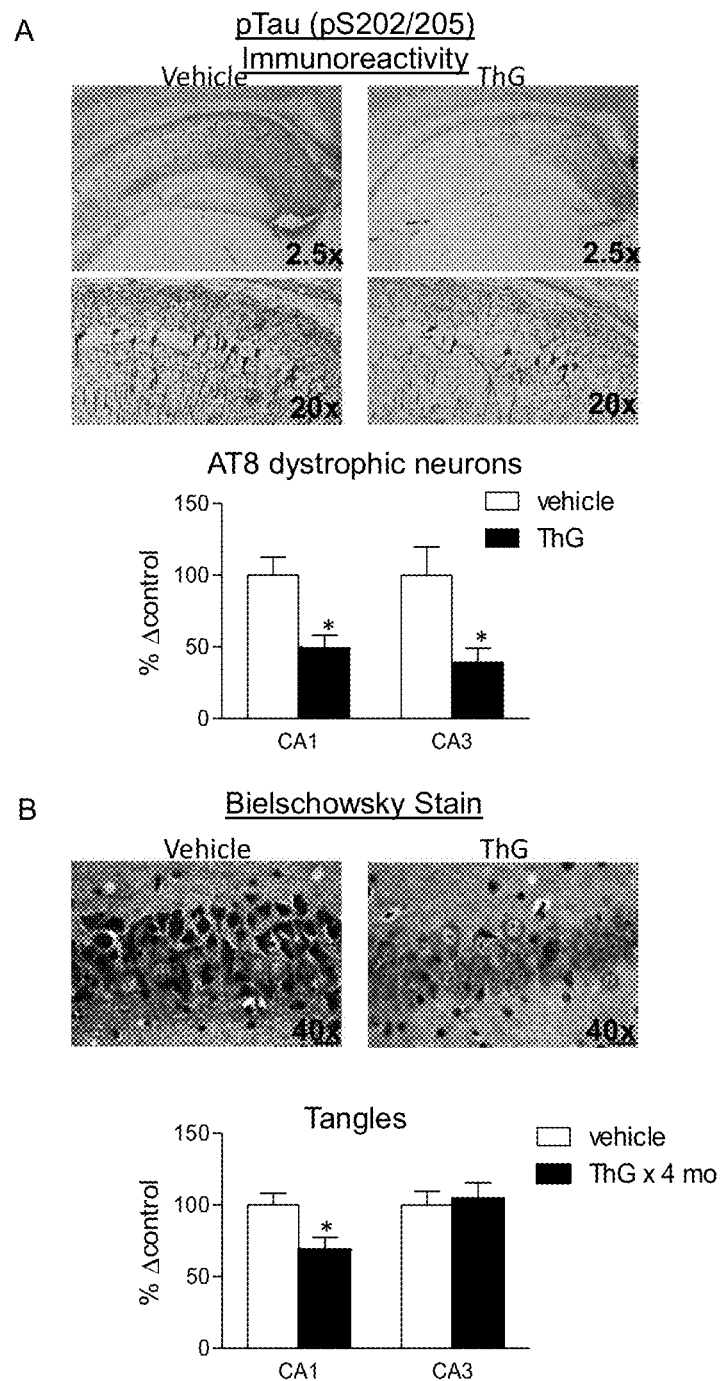

FIG. 3: Effects of chronic ThiametG treatment on tau dystrophic neurons and tangles in the hippocampus. A, AT8 positive neurons are significantly reduced in the CA1 and CA3 region of the hippocampus following 4 months administration of ThiametG. B, Agyrophilic fibers (as measured via Bielschowsky stain) are significantly reduced in the CA1 region of the hippocampus, but not the CA3 region following 4 months administration of ThiametG. IHC and Bielschowsky quantification (N=13-15/group) are expressed as mean±s.e.m. percentage of vehicle-treated controls.

MATERIALS & METHODS

Animals: Tg(tauP301L)4510 mice were generated as previously described (Santacruz et al., 2005, Science 309: 476-481). Animals were bred and housed at the McLaughlin Research Institute (Great Falls, Mont.). All experiments were approved by the MRI Institutional Animal Care and Use Committee (IACUC). The acute (1 day treatment) and subchronic (14 day treatment) effects of ThiametG were evaluated in male and female 3 month old Tg4510 mice. The chronic (4 month) effects of ThiametG were evaluated in male and female Tg4510 mice beginning at 2 months of age. ThiametG was dissolved in water and administered po, at a concentration of 500 mg/kg/day.

O-GlcNAc tau specific antibody (Otau(S400)): To generate a rabbit monoclonal antibody specific for tau O-GlcNAcylated at serine 400 rabbits were immunized with a peptide (cVYKSPVV-(O-GlcNAc)S-GDTSPRH) corresponding to amino acids 393 to 407 on 2N4R human tau. Lymphocytes from rabbits with high titer antisera were isolated and hybridomas generated. IgG antibodies were purified from supernatant of positive hybridoma subclones. The specificity of the antibody was confirmed on Western blots with samples of recombinant O-GlcNAcylated tau and lysates from HEK293 cells coexpressing OGT and human 2N4Rtau (data not shown).

Tau immunoprecipitation: To immunoprecipitate tau protein from brain lysates a Crosslink Immunoprecipitation kit (Pierce 26147) was used. The A/G resin was crosslinked to 10 μg of the HT7 tau antibody (Thermo Scientific MN1000) or control mouse IgG (Santa Cruz Biotech sc-2025) via the manufacturer's protocol. 250 μg of brain lysates prepared as described below was incubated with the resin-coupled tau antibody overnight at 4-C. Samples were eluted with 50 μl of low pH Elution buffer and immediately centrifuged into collection tubes containing 5 μl of 1M Tris, pH 9.5. Immunoprecipitated tau was subjected to Western blotting as described below.

Western Blot: To examine changes in O-GlcNAcylation and phosphorylation, animals were euthanized 4 h after injection in the acute or subchronic studies and 24 h after the last injection in the chronic study. Hemi-forebrains were rapidly dissected and frozen on dry ice. Tissue samples were homogenized in Phosphosafe Buffer (EMD Chemicals), followed by a low-speed centrifugation (15,000 g) to remove cellular debris. The resulting supernatant (low-speed supernatant, Lss) was assayed to determine protein concentrations by Lowry method. O-GlcNAcylation and phosphorylation were determined in 20 μg protein samples subjected to 4-15% SDS-PAGE (Tris-HCl gels, Bio-Rad), followed by a transfer to nitrocellulose membranes (Invitrogen, IBlot system). Membranes were blocked in Licor blocking buffer at room temperature for 1 h and incubated in primary antibody overnight at 4° C. Total protein O-GlcNAcylation was detected using the RL2 antibody (1:500, ThermoScientific), tau O-GlcNAcylation was detected using the Otau (S400) antibody (1:500) and tau phosphorylation was detected using AT8 (1:500, ThermoScientific), pS396, pS262, pS356 (1:500, Abcam) and pS400 (1:5000, GenScript). GAPDH (1:1000, Abcam) or total tau (1:50,000 ThermoScientific) antibodies served as internal loading controls. Membranes were incubated with species-specific fluorophore-conjugated secondary (1:10,000; Licor) antibodies for 1 h at room temperature and detected using the Licor Odyssey.

Tau fractionation: To analyze 50-60 kD versus 64 kD tau, the Lss fraction containing both 50-60 kD and 64 kD tau species was centrifuged at high speed (110,000 g for 15 min). The supernatant (S1 fraction) containing the 50-60 kD tau proteins was removed and assayed to determine protein concentrations. To analyze changes in 50-60 kD and 64 kD tau, the Lss and S1 fractions were subjected to 10% SDS-PAGE (Tris-HCl gels, Bio-Rad) followed by transfer as described above. 64 kD tau appeared as one compact band with an apparent mass of ~64 kD in whole brain lysate (Lss fraction), but was absent in the supernatant (S1 fraction) after high speed centrifugation, which separates 50-60 kD from 64 kD tau (FIG. 2B). 50-60 kD tau appears as several bands with an apparent mass ranging from ~50-60 kD.

Immunohistochemistry: To examine changes in tangle pathology, a hemibrain was dissected and immersion fixed in 10% neutral buffered formalin for 24-48 h and subsequently embedded in paraffin blocks. 10 micron serial coronal sections were mounted onto Superfrost Plus slides, and stained using Bond Intense R kit. To detect dystrophic AT8 neurons, mounted slides were pretreated with antigen retrieval solutions for 10 min followed by washes with BOND wash buffer. Sections were subsequently quenched with hydrogen peroxide in Bond Intense R kit, blocked with M.O.M. blocking buffer (M.O.M Immunodetection Kits, Vector Laboratories), and then incubated with pS202/205 primary antibody (1:500; ThermoScientific). Sections were then incubated sequentially with biotinylated donkey anti-mouse secondary antibody (1:200; Jackson Immunoresearch), Streptavidin-HRP, and 3,3'-diaminobenzidine (both BOND Intense R kit). To detect agyrophilic tangles, sections were deparafinized, rehydrated in distilled water and treated with formaldehyde (4%) overnight at 37° C. Sections were washed in tap water, incubated in a 20% silver nitrate solution for 15 min in the dark, washed, incubated with ammoniated silver solution for 10 min in the dark, washed in ammonia water, and treated with developer. Sections were subsequently washed in ammonia water, distilled water, thiosulfate sodium, dehydrated and mounted.

Immunofluorescence: To examine the colocalization between O-GlcNAcylated tau and AT8, sections were blocked with 5% Normal Goat Serum (Jackson Immunoresearch) for 1 h, followed by a sequential incubation with Otau(S400); (1:100, 1 h) and AT8 (1:500, 1 h). After washing, sections were incubated with secondary FITC conjugated goat anti-rabbit and Texas Red conjugated goat anti-mouse (Invitrogen) antibodies in PBS for 1 h. After washing, slides were coverslipped with Prolong Gold antifade reagent (Invitrogen).

Statistical Analysis: Protein O-GlcNAcylation and phosphorylation changes were analyzed by one-factor ANOVA, followed by Dunnets post hoc comparisons or by t-test for those studies with only two treatment groups. Immunohistochemistry was analyzed by t-test.

Results (i) Acute and Subchronic OGA Inhibition Increases Tau O-GlcNAcylation and Transiently Reduces Tau Phosphorylation.

To investigate the effects of increased O-GlcNAcylation on tau phosphorylation, the Tg4510 mouse model was chosen because it closely mimics human tauopathy and represents an important model for the study of tau-related neurodegenerative diseases. Tg4510 mice received either a single or repeated injection of the OGA inhibitor ThiametG or vehicle. ThiametG is a potent inhibitor of OGA with an IC50 of ~5 nM. OGA catalyzes the removal of O-GlcNAc residues from proteins and thus inhibition of OGA results in a relative increase of O-GlcNAc modification on proteins. A significant increase in total protein O-GlcNAcylation in the CNS was observed following either a single injection of ThiametG ($F_{(2,43)}$=20.98; $p<0.01$ as compared to vehicle-treated; FIG. 1A) or 14 days of administration ($F_{(2, 43)}$=12.57; $p<0.01$). The increase in total protein O-GlcNAcylation following 14 days of ThiametG was significantly higher than that following a single injection ($p<0.05$).

To specifically investigate the effects of ThiametG treatment on tau O-GlcNAcylation, a rabbit monoclonal antibody specific to O-GlcNAcylation of tau at serine 400 (Otau(S400)) was generated. S400 can be modified by O-GlcNAcylation (Yuzawa et al., 2010, Amino Acids 40: 857-868) and is located between S396 and S404, which are phosphorylation sites known to be implicated in tau pathology. To confirm that Otau(S400) indeed recognized O-GlcNAcylated tau, tau was immunoprecipitated with a pan-specific tau antibody (HT7) from brains of Tg4510 mice that had been subchronically treated with ThiametG and probed with the Otau(S400) antibody. The Otau(S400) antibody strongly recognized immunoprecipitated tau in the ThiametG treated animals, but only to a much lesser extent in the vehicle-treated animals (FIG. 1B). Interestingly, O-GlcNAcylated tau was detected at the lower molecular mass bands of tau, indicating that only a subset of tau was O-GlcNAcylated. Only a small increase in tau O-GlcNAcylation was detected following a single injection of ThiametG. However, repeated injection of ThiametG produced a 9-fold increase in tau O-GlcNAcylation ($F_{(2, 42)}$=22.04; $p<0.05$ as compared to vehicle-treated; FIG. 1C). This confirms that tau is a substrate for O-GlcNAcylation and that OGA inhibition robustly increases O-GlcNAc on tau at serine 400 in a mouse model of tau pathology.

A single injection of ThiametG reduced tau phosphorylation at epitopes S202/205 ($F_{(2, 43)}$=43.49; $p<0.05$), S262 ($F_{(2, 43)}$=27.36; $p<0.05$), S356 $F_{(2, 43)}$=33.31; $p<0.05$ and S396 ($F_{(2, 43)}$=22.48; $p<0.05$; FIG. 1D). Acute ThiametG treatment did not alter tau phosphorylation at S400, suggesting that O-GlcNAcylation does not regulate tau phosphorylation at this epitope. Interestingly, repeated treatment with ThiametG did not produce a greater reduction in tau phosphorylation at the investigated epitopes. In the case of S202/205, S262 and S396 phosphorylation returned towards basal levels following 14 days of ThiametG, whereas phosphorylation at S356 was still significantly reduced ($F_{(2, 43)}$=26.72; $p<0.05$), but showed a trend towards increased phosphorylation.

(ii) Chronic Inhibition of OGA Reduces Tau Pathology.

To examine the chronic effects of ThiametG on tau pathology, Tg4510 animals received 4 months of treatment with ThiametG beginning at 2 months of age. Mice were intentionally selected at this age to start the treatment paradigm before any signs of pathological tau accumulation and neurodegeneration. Twenty-four hours after the last injection brain tissue was collected for tau protein analysis via western blot as well as histological analysis for tangles. The levels of total protein O-GlcNAcylation following 4 months of ThiametG were similar (185%) to that produced after the 14-day treatment (data not shown). Furthermore, tau O-GlcNAcylation remained elevated 9-fold following 4 months of dosing, comparable to the level of tau O-GlcNAcylation after 14 days of ThiametG treatment, indicating that tau O-GlcNAcylation reached a steady state already after 2 weeks of OGA inhibition ($T_{27}$=18.95; $p<0.0001$; FIG. 2A). Notably, O-GlcNAcylation appeared on tau at the lower molecular mass bands and was absent from the 64 kD band representing pathological tau, suggesting that only non-pathological tau is O-GlcNAcylated. To corroborate that pathological tau is not O-GlcNAcylated, dual-labeling immunofluorescence experiments were performed on brain slices of ThiametG treated Tg4510 mice with the Otau (S400) antibody (FIG. 2C, top panel) and the AT8 antibody (FIG. 2C, middle panel), which recognizes hyperphosphorylated aggregated tau. Individual neurons in the CA1 region of the hippocampus showed strong AT8-immunoreactivity in the soma and neurites (FIG. 2B, middle panel), whereas O-GlcNAc-tau immunoreactivity was mainly localized to neuronal cell bodies (FIG. 2C, top panel). No colocalization of O-GlcNAc-tau with pathological tau was observed (FIG. 2C, bottom panel), which agrees with the biochemical analysis that pathological tau species are not O-GlcNAcylated in Tg4510 brains.

Hyperphosphorylated pathological tau was biochemically identified by differential centrifugation of brain homogenate from Tg4510 mice and detection with phospho-tau specific antibodies. Pathological tau appeared as one compact high molecular mass band at around 64 kD in whole brain homogenate (low speed spin fraction; Lss), but was absent in the supernatant after high speed centrifugation (S1 fraction), which separates normal from pathological tau (FIG. 2B). The S1 fraction contained tau species with an apparent molecular mass ranging from ~50-60 kD. Chronic treatment with ThiametG significantly decreased 64 kD tau as detected with phosphorylation-specific antibodies directed at S202/205 ($T_{27}$=2.984; $p<0.01$), S400 ($T_{27}$=2.769; $p<0.01$), S356 ($T_{27}$=2.132; $p<0.05$) and S262 ($T_{27}$=3.030; $p<0.01$; FIG. 2B) of tau, indicating that a sustained increase in tau O-GlcNAcylation prevents the accumulation of pathological tau.

There was no change in the phosphorylation state of the 50-60 kD tau species (FIG. 2D) at various epitopes implicated in tau aggregation, namely S202/205, S356, and S262. This suggests that a sustained increase in O-GlcNAcylation does not regulate the phosphorylation of the 50-60 kD tau species and thus may prevent pathological tau accumulation independent of the phosphorylation level. This contrasts with the reduction in tau phosphorylation observed after a single injection of ThiametG and is inconsistent with the notion in the art that tau phosphorylation is directly regulated by O-GlcNAcylation through competitive or adjacent site occupancy.

To confirm the effect of OGA inhibition on tau aggregation, tau pathology was assessed histologically in brain slices of ThiametG treated Tg4510 mice. Consistent with the biochemical analysis, chronic treatment with ThiametG significantly reduced pS202/205 (AT8) positive dystrophic neurons in CA1 ($T_{26}$=3.053, $p<0.01$) and CA3 ($T_{25}$=3.046, $p<0.01$) region of the hippocampus (FIG. 3). Furthermore, to demonstrate that AT8 immunoreactive neurons indeed reflect tangle bearing neurons, Bielschowsky staining was performed on brain slices of ThiametG and vehicle treated animals. Consistent with AT8 immunohistochemistry, a significant reduction of tangle pathology in the CA1 region of the hippocampus was found ($T_{(25)}$=2.309; $p<0.05$; FIG. 3B). However, no difference was observed in tangle burden in the CA3 region of the hippocampus. This may be due to differences in sensitivity for early tau aggregates between the methodologies.

Taken together, the results suggest that increasing O-GlcNAc levels on tau attenuates the formation of pathological tau species in the Tg4510 mouse model.

DISCUSSION

It was shown that chronic pharmacological treatment of the Tg4510 tau mouse model with a potent and selective inhibitor of OGA, ThiametG, results in a significant reduction in tau pathology as measured biochemically and pathologically. A highly significant reduction in pathological 64 kD tau was observed in brain homogenates of ThiametG treated animals. This tau species represents a distinct low speed soluble, but high speed sedimentable pool of aggregated tau, most likely consisting of tau dimers and oligomers. These early tau aggregates precede NFT formation and correlate better with neuronal dysfunction and degeneration than that of sarkosyl-insoluble tau or NFT in Tg4510 mouse brain. Similarly, in certain areas of Alzheimer's Disease (AD) brain neuronal loss and NFT pathology are topographically distinct with the number of degenerated neurons far greater than that of NFT bearing neurons, implying that NFT are unlikely to be the primary neurotoxic agent during disease progression. Moreover, abnormal tau structurally similar to the pathological 64 kD tau species in Tg4510 mice is found in human tauopathies, making these aggregated tau intermediates a potential target for therapeutic treatment. With this study, it was clearly demonstrated that the pathological 64 kD species of tau can be reduced through long term inhibition of OGA, making OGA an attractive molecular target for drug discovery. This observation is also in close agreement with the immunohistological findings that showed significantly fewer neurons immunoreactive with the AT8 antibody, a marker for pathological tau aggregates, in animals treated with ThiametG.

Importantly, markedly stronger O-GlcNAcylation of tau was found in response to chronic OGA inhibition, which may account for the more pronounced effect on pathological tau. The difference in tau O-GlcNAcylation may be explained by the use of the Tg4510 tau mouse model in this study, which transgenically expresses tau at a higher level than the JNPL3 mouse model. Additionally, the site-specific O-GlcNAc-tau antibody may have higher affinity for tau O-GlcNAcylated at S400 as the 3925 antibody. Notably, in this study O-GlcNAc modification at S400 was only found on tau that migrated at lower molecular mass on polyacrylamide gels and was absent from AT8 immunopositive neurons, suggesting that only non-pathological tau was O-GlcNAcylated. This agrees with the notion that O-GlcNAcylation maintains tau in a state that renders it less prone to aggregation. Consistently, non-pathological tau immunopurified from brains of AD patients was found to be more O-GlcNAcylated than hyperphosphorylated pathological tau.

Chronic OGA inhibition decreased the abundance of pathological tau aggregates in Tg4510 mouse brain without affecting phosphorylation levels of non-pathological tau. This suggests that O-GlcNAcylation may not directly regulate the phosphorylation of tau, but attenuate tau aggregation through a phosphorylation-independent mechanism. Although it cannot be completely ruled out that other O-GlcNAc dependent mechanisms are responsible for the effect on tau aggregation, it is likely that O-GlcNAcylation of tau directly lessen its oligomerization propensity as has been demonstrated in vitro with truncated forms of O-GlcNAc-modified tau. In this context it is important to note that O-GlcNAcylation at S400 appears to play a predominant role in inhibiting tau oligomerization, which is consistent with the highly significant 9-fold increase in tau O-GlcNAcylation at S400 and the concurrent reduction in tau aggregation in response to chronic OGA inhibition as observed in this study. This protective effect of O-GlcNAcylation on protein aggregation is not singular to tau, as O-GlcNAcylated versions of TAB1 and alpha-synuclein peptides were less prone to oligomerization as compared to their unmodified counterparts. As O-GlcNAcylation prevents different types of amyloidogenic proteins from aggregating, OGA inhibition may provide a therapeutic strategy to a multitude of diseases caused by aberrant protein aggregation beyond AD.

In summary, these data, for the first time, demonstrate that a chronic increase in tau O-GlcNAcylation protects against the formation of hyperphosphorylated tau aggregates, which are closely linked to neurotoxicity observed in AD and other tauopathies. This study strongly supports OGA as a molecular target for a disease-modifying therapy to attenuate the progression of tau pathology in AD and other tauopathies.

The invention claimed is:

1. A compound of sub-formula (IB)

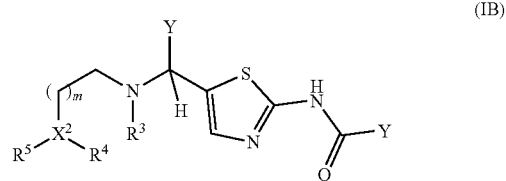

(IB)

wherein $X^2$ denotes CY;

$R^3$, $R^4$ are either independently from one another Y or, if together, denote $-(CY_2)_p-$;

$R^5$ denotes $(CH_2)_q Ar$, Cyc or A;

Y denotes H or A;

A denotes $C_{1-4}$ alkyl;

Cyc denotes cyclohexyl;

Ar denotes phenyl, which can be para- or metasubstituted by A or OY, or which can be fused to a saturated or an aromatic monocyclic heterocycle having 3-4 C atoms and 2 O or N atoms;

Hal denotes F, Cl, Br or I;

m denotes 0, 1 or 2;

p denotes 1 or 2; and q denotes 0 or 1;

and/or a physiologically acceptable salt thereof.

2. The compound according to claim 1, wherein m denotes 1 or 2.

3. The compound according to claim 1 selected from the group of:

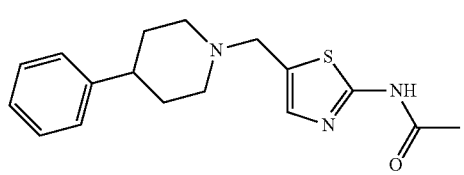

1

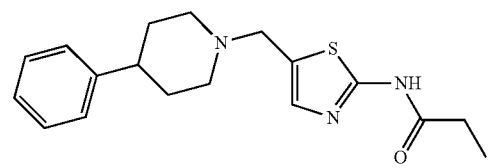
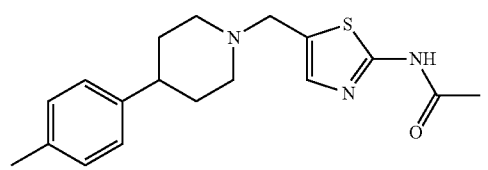
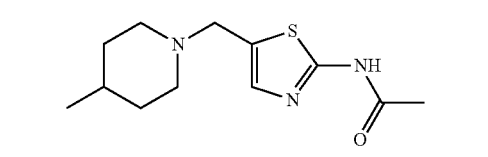
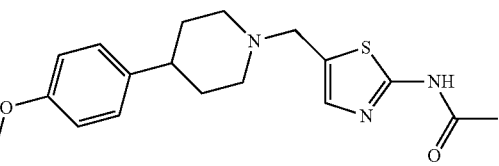
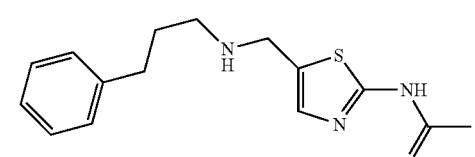
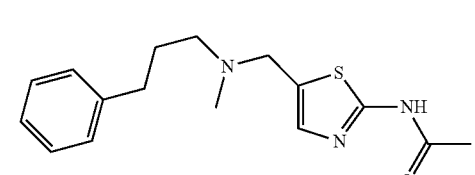
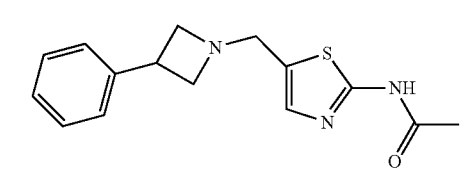
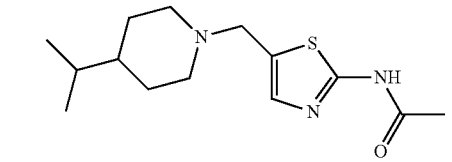
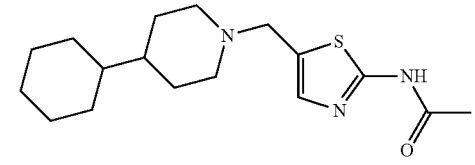
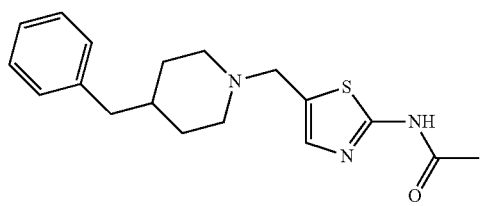
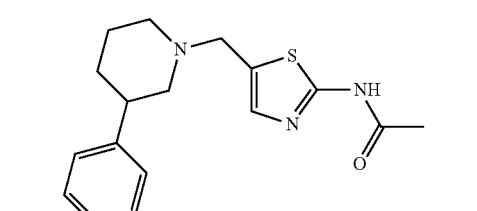
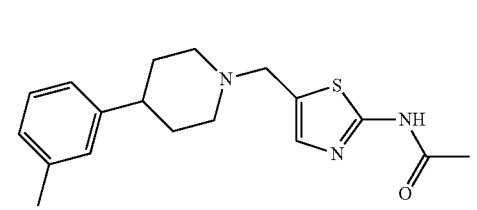
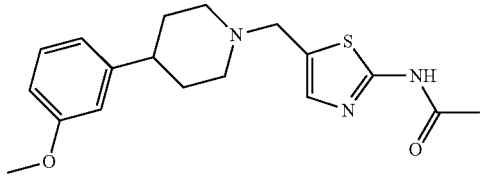
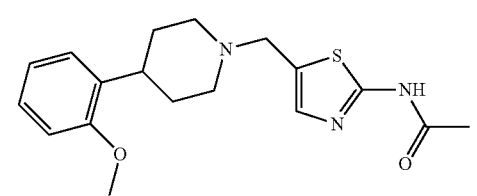
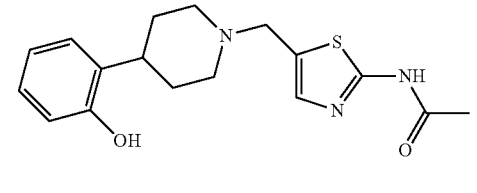
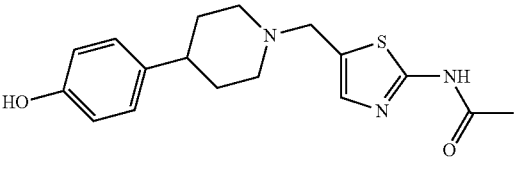
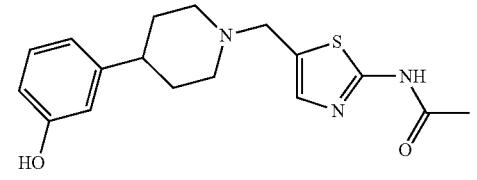

40 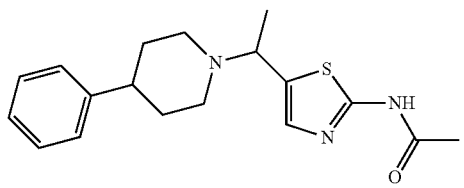

43 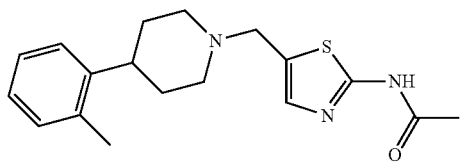

47 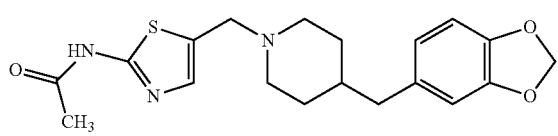

51 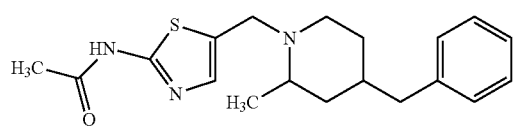

53 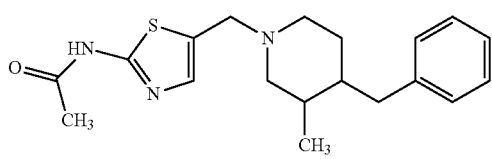

54 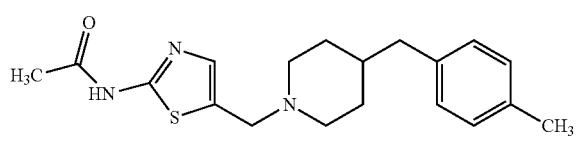

55 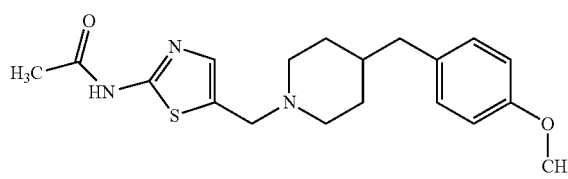

63 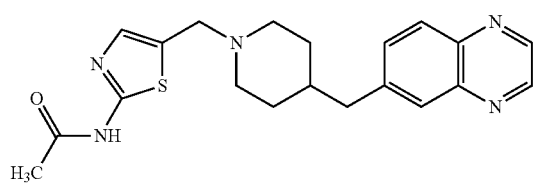

and/or a physiologically acceptable salt thereof.

4. A pharmaceutical composition comprising as active ingredient an effective amount of a compound according to claim 1 and/or a physiologically acceptable salt thereof, wherein the active ingredient is provided together with pharmaceutically tolerable adjuvants and/or excipients in the pharmaceutical composition, optionally in combination with one or more further active ingredients.

5. A method for treating conditions selected from the group consisting of a neurodegenerative disease, diabetes, cancer and stress, wherein a compound according to claim 1 and/or a physiologically acceptable salt thereof is administered to a mammal in need thereof.

6. The method according to claim 5, wherein the condition is a neurodegenerative disease.

7. The method according to claim 5, wherein the condition is selected from the group of Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Richardson's syndrome, Subacute sclerosing panencephalitis, Tangle-only dementia, Huntington's disease and Parkinson's disease.

8. The method according to claim 5, wherein the condition is selected from the group of Alzheimer's disease, Amyotrophic lateral sclerosis (ALS), Corticobasal degeneration (CBP), Frontotemporal dementia with parkinsonism linked to chromosome 17 (FTDP-17), Niemann-Pick disease (type C), Parkinsonism-dementia complex of Guam, Pick's disease (PiD), Progressive supranuclear palsy (PSP) and Parkinson's disease.

9. The method according to claim 5, wherein the condition is Alzheimer's disease.

10. The method according to claim 5, wherein the condition is a tauopathy.

11. A method for inhibiting a glycosidase, wherein a system expressing the glycosidase is contacted with a compound according to claim 1 and/or a physiologically acceptable salt thereof under in-vitro conditions such that the glycosidase is inhibited.

* * * * *